(12) United States Patent
Lee et al.

(10) Patent No.: US 8,142,510 B2
(45) Date of Patent: Mar. 27, 2012

(54) MOBILE BEARING ASSEMBLY HAVING A NON-PLANAR INTERFACE

(75) Inventors: Jordan S. Lee, Warsaw, IN (US); James M. Rhodes, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 120 days.

(21) Appl. No.: 12/049,699

(22) Filed: Mar. 17, 2008

(65) Prior Publication Data

US 2008/0243260 A1  Oct. 2, 2008

Related U.S. Application Data

(60) Provisional application No. 60/909,259, filed on Mar. 30, 2007.

(51) Int. Cl.
 *A61F 2/38* (2006.01)
(52) U.S. Cl. .................. 623/20.33; 623/20.34; 623/20.3
(58) Field of Classification Search .... 623/20.28–20.34, 623/20.24, 20.31, 20.3–20.32, 20.14–20.16, 623/20.21, 20.26–20.27, 21.18
 See application file for complete search history.

(56) References Cited

U.S. PATENT DOCUMENTS

| 3,506,982 | A |   | 4/1970  | Steffee         |           |
|-----------|---|---|---------|-----------------|-----------|
| 3,605,123 | A |   | 9/1971  | Hahn            |           |
| 3,855,638 | A |   | 12/1974 | Pilliar         |           |
| 3,906,550 | A |   | 9/1975  | Rostoker et al. |           |
| 3,953,899 | A |   | 5/1976  | Charnley        |           |
| 4,016,606 | A |   | 4/1977  | Murray et al.   |           |
| 4,205,400 | A |   | 6/1980  | Shen et al.     |           |
| 4,207,627 | A |   | 6/1980  | Cloutier        |           |
| 4,213,816 | A |   | 7/1980  | Morris          |           |
| 4,216,549 | A | * | 8/1980  | Hillberry et al.| 623/20.26 |
| 4,224,696 | A | * | 9/1980  | Murray et al.   | 623/20.29 |
| 4,224,697 | A |   | 9/1980  | Murray et al.   |           |
| 4,340,978 | A | * | 7/1982  | Buechel et al.  | 623/20.29 |

(Continued)

FOREIGN PATENT DOCUMENTS

BE 1008201 2/1996

(Continued)

OTHER PUBLICATIONS

European Search Report for European Patent Application No. 08251212.0-2310, Jul. 21, 2008, 7 pgs.

(Continued)

*Primary Examiner* — David Isabella
*Assistant Examiner* — Marcia Hoffman
(74) *Attorney, Agent, or Firm* — Barnes & Thornburg LLP

(57) ABSTRACT

A mobile tibial assembly includes a tibial tray and a tibial insert. The tibial tray includes a track that is defined in an upper surface, and the track has a bottom wall that is flat in the medial-lateral direction and convex in the anterior-posterior direction. The tibial insert includes a bottom bearing surface configured to contact the upper surface of the tibial tray and a stem including a circular neck connected to the bottom bearing surface. The bottom bearing surface has a surface area that is less than the cross-sectional area of the circular neck. The convex upper surface of the tibial tray contacts the concave bottom bearing surface of the tibial insert and the tibial insert is freely rotatable about a central axis defined by the stem as the tibial insert is moved along the track relative to the tibial tray in the generally anterior-posterior direction.

7 Claims, 37 Drawing Sheets

U.S. PATENT DOCUMENTS

| | | | |
|---|---|---|---|
| 4,454,612 | A | 6/1984 | McDaniel et al. |
| 4,470,158 | A | 9/1984 | Pappas et al. |
| 4,479,271 | A | 10/1984 | Bolesky |
| 4,501,031 | A | 2/1985 | McDaniel et al. |
| 4,568,348 | A | 2/1986 | Johnson et al. |
| 4,589,883 | A | 5/1986 | Kenna |
| 4,636,219 | A | 1/1987 | Pratt et al. |
| 4,718,413 | A | 1/1988 | Johnson |
| 4,719,908 | A | 1/1988 | Averill et al. |
| 4,728,332 | A | 3/1988 | Albrektsson |
| 4,743,261 | A | 5/1988 | Epinette |
| 4,795,468 | A | 1/1989 | Hodorek et al. |
| 4,911,721 | A | 3/1990 | Branemark et al. |
| 4,936,847 | A | 6/1990 | Manginelli |
| 4,944,757 | A | 7/1990 | Martinez et al. |
| 4,950,298 | A | 8/1990 | Gustilo et al. |
| 4,997,445 | A | 3/1991 | Hodorek |
| 5,019,103 | A | 5/1991 | Van Zile et al. |
| 5,047,058 | A | 9/1991 | Roberts et al. |
| 5,108,452 | A | 4/1992 | DeMane et al. |
| 5,152,797 | A | 10/1992 | Luckman et al. |
| 5,201,769 | A | 4/1993 | Schutzer |
| 5,226,915 | A | 7/1993 | Bertin |
| 5,263,987 | A | 11/1993 | Shah |
| 5,282,868 | A | 2/1994 | Bahler |
| 5,330,532 | A | 7/1994 | Ranawat |
| D354,810 | S | 1/1995 | Nazre |
| 5,395,401 | A | 3/1995 | Bahler |
| D357,534 | S | 4/1995 | Hayes |
| D359,557 | S | 6/1995 | Hayes |
| 5,458,637 | A | 10/1995 | Hayes |
| 5,609,639 | A * | 3/1997 | Walker ................. 623/20.29 |
| 5,609,640 | A | 3/1997 | Johnson |
| 5,658,341 | A | 8/1997 | Delfosse |
| 5,702,458 | A | 12/1997 | Burstein et al. |
| 5,702,459 | A | 12/1997 | Hummer et al. |
| 5,716,361 | A | 2/1998 | Masini |
| 5,755,801 | A | 5/1998 | Walker et al. |
| 5,800,560 | A | 9/1998 | Draenert |
| 5,810,827 | A | 9/1998 | Haines et al. |
| 5,824,106 | A | 10/1998 | Fournol |
| 5,855,296 | A | 1/1999 | McCann et al. |
| 5,871,541 | A * | 2/1999 | Gerber ................. 623/20.29 |
| 5,879,354 | A | 3/1999 | Haines et al. |
| 5,888,034 | A | 3/1999 | Greenberg |
| 5,944,722 | A | 8/1999 | Masini |
| 5,947,973 | A | 9/1999 | Masini |
| 5,957,926 | A | 9/1999 | Masini |
| 5,957,979 | A | 9/1999 | Beckman et al. |
| 5,961,523 | A | 10/1999 | Masini |
| 5,971,989 | A | 10/1999 | Masini |
| 6,004,351 | A * | 12/1999 | Tomita et al. ................. 623/2.21 |
| 6,010,534 | A | 1/2000 | O'Neil et al. |
| 6,019,767 | A | 2/2000 | Howell |
| 6,039,764 | A | 3/2000 | Pottenger et al. |
| 6,056,754 | A | 5/2000 | Haines et al. |
| 6,068,633 | A | 5/2000 | Masini |
| 6,077,269 | A | 6/2000 | Masini |
| 6,102,916 | A | 8/2000 | Masini |
| 6,106,529 | A | 8/2000 | Techiera |
| 6,123,728 | A | 9/2000 | Brosnahan et al. |
| 6,139,581 | A * | 10/2000 | Engh et al. ................. 623/20.34 |
| 6,171,340 | B1 | 1/2001 | McDowell |
| 6,187,010 | B1 | 2/2001 | Masini |
| 6,197,064 | B1 | 3/2001 | Haines et al. |
| 6,214,011 | B1 | 4/2001 | Masini |
| 6,254,604 | B1 | 7/2001 | Howell |
| 6,254,605 | B1 | 7/2001 | Howell |
| 6,296,666 | B1 | 10/2001 | Gardner |
| 6,361,564 | B1 | 3/2002 | Marceaux et al. |
| 6,419,707 | B1 | 7/2002 | Leclercq |
| 6,428,577 | B1 | 8/2002 | Evans et al. |
| 6,494,914 | B2 | 12/2002 | Brown et al. |
| 6,503,254 | B2 | 1/2003 | Masini |
| 6,506,215 | B1 | 1/2003 | Letot et al. |
| 6,520,964 | B2 | 2/2003 | Tallarida et al. |
| 6,602,292 | B2 | 8/2003 | Burkinshaw |
| 6,616,696 | B1 | 9/2003 | Merchant |
| 6,660,039 | B1 | 12/2003 | Evans et al. |
| 6,702,821 | B2 | 3/2004 | Bonutti |
| 6,730,128 | B2 * | 5/2004 | Burstein ................. 623/20.27 |
| 6,770,078 | B2 | 8/2004 | Bonutti |
| 6,869,448 | B2 | 3/2005 | Tuke et al. |
| 6,916,341 | B2 | 7/2005 | Rolston |
| 6,946,001 | B2 | 9/2005 | Sanford et al. |
| 7,033,397 | B2 | 4/2006 | Webster et al. |
| 7,101,401 | B2 | 9/2006 | Brack |
| 7,105,027 | B2 | 9/2006 | Lipman et al. |
| 7,115,131 | B2 | 10/2006 | Engh et al. |
| 7,708,741 | B1 * | 5/2010 | Bonutti ................. 606/86 R |
| 7,931,690 | B1 | 4/2011 | Bonutti |
| 2001/0037155 | A1 | 11/2001 | Merchant |
| 2002/0055784 | A1 | 5/2002 | Burstein et al. |
| 2003/0009232 | A1 | 1/2003 | Metzger et al. |
| 2003/0028196 | A1 | 2/2003 | Bonutti |
| 2003/0033018 | A1 | 2/2003 | Merchant |
| 2003/0120346 | A1 | 6/2003 | Mercinek et al. |
| 2003/0158606 | A1 | 8/2003 | Coon et al. |
| 2003/0181984 | A1 | 9/2003 | Abendschein |
| 2003/0187510 | A1 | 10/2003 | Hyde |
| 2003/0195633 | A1 | 10/2003 | Hyde |
| 2004/0006394 | A1 | 1/2004 | Lipman et al. |
| 2004/0039447 | A1 * | 2/2004 | Simon et al. ................. 623/13.11 |
| 2004/0107000 | A1 | 6/2004 | Felt et al. |
| 2004/0143338 | A1 | 7/2004 | Burkinshaw et al. |
| 2004/0153066 | A1 | 8/2004 | Coon et al. |
| 2004/0153164 | A1 | 8/2004 | Sanford et al. |
| 2004/0167630 | A1 | 8/2004 | Rolston |
| 2004/0193280 | A1 * | 9/2004 | Webster et al. ............. 623/20.33 |
| 2004/0254645 | A1 | 12/2004 | Arnin et al. |
| 2005/0015153 | A1 | 1/2005 | Goble et al. |
| 2005/0027365 | A1 | 2/2005 | Burstein et al. |
| 2005/0096747 | A1 | 5/2005 | Tuttle et al. |
| 2005/0119663 | A1 | 6/2005 | Keyer et al. |
| 2005/0119664 | A1 | 6/2005 | Carignan et al. |
| 2005/0143830 | A1 | 6/2005 | Mercinek et al. |
| 2005/0143831 | A1 | 6/2005 | Justin et al. |
| 2005/0143833 | A1 | 6/2005 | Merchant |
| 2005/0149041 | A1 | 7/2005 | McGinley et al. |
| 2005/0171604 | A1 | 8/2005 | Michalow |
| 2005/0171612 | A1 | 8/2005 | Rolston |
| 2005/0177242 | A1 | 8/2005 | Lotke |
| 2005/0197709 | A1 | 9/2005 | Schaefer et al. |
| 2005/0203384 | A1 | 9/2005 | Sati et al. |
| 2005/0234465 | A1 | 10/2005 | McCombs et al. |
| 2005/0240273 | A1 | 10/2005 | Khandkar et al. |
| 2005/0278034 | A1 | 12/2005 | Johnson et al. |
| 2006/0004460 | A1 | 1/2006 | Engh et al. |
| 2006/0009776 | A1 | 1/2006 | Justin et al. |
| 2006/0009854 | A1 | 1/2006 | Justin et al. |
| 2006/0009855 | A1 | 1/2006 | Goble et al. |
| 2006/0030855 | A1 | 2/2006 | Haines |
| 2006/0030945 | A1 | 2/2006 | Wright |
| 2006/0085072 | A1 | 4/2006 | Funk et al. |
| 2006/0089720 | A1 | 4/2006 | Schneier |
| 2006/0122616 | A1 | 6/2006 | Bennett et al. |
| 2006/0129246 | A1 | 6/2006 | Steffensmeier |
| 2006/0190086 | A1 | 8/2006 | Clemow et al. |
| 2006/0195195 | A1 | 8/2006 | Burstein et al. |
| 2006/0195196 | A1 | 8/2006 | Pendleton et al. |
| 2006/0235537 | A1 | 10/2006 | Kuczynski et al. |
| 2006/0265079 | A1 | 11/2006 | D'Alessio |
| 2007/0010890 | A1 | 1/2007 | Collazo |
| 2007/0100459 | A1 | 5/2007 | Rhodes |
| 2007/0100460 | A1 | 5/2007 | Rhodes |
| 2008/0033567 | A1 | 2/2008 | Stchur |
| 2008/0086210 | A1 * | 4/2008 | Fox ................. 623/14.12 |

FOREIGN PATENT DOCUMENTS

| | | |
|---|---|---|
| DE | 10012060 | 9/2001 |
| DE | 10053623 | 5/2002 |
| EP | 0135319 A2 | 3/1985 |
| EP | 0183670 | 6/1986 |
| EP | 0327387 A2 | 8/1989 |
| EP | 0328463 A1 | 8/1989 |
| EP | 0874596 A1 | 11/1998 |
| EP | 0709075 B1 | 8/2001 |

| | | |
|---|---|---|
| EP | 1327424 | 7/2003 |
| EP | 1329205 A1 | 7/2003 |
| EP | 1374782 A2 | 1/2004 |
| EP | 1442726 | 8/2004 |
| EP | 1442728 A2 | 8/2004 |
| EP | 1550418 | 7/2005 |
| EP | 1557144 A1 | 7/2005 |
| EP | 1584309 | 10/2005 |
| EP | 1669034 A1 | 6/2006 |
| EP | 1702590 A2 | 9/2006 |
| EP | 1741412 | 1/2007 |
| FR | 2663536 | 12/1991 |
| FR | 2702369 | 9/1994 |
| FR | 2721820 | 1/1996 |
| FR | 2885516 A1 | 11/2006 |
| GB | 2355935 | 5/2001 |
| JP | 2002272756 | 9/2002 |
| WO | 9110412 A1 | 7/1991 |
| WO | 9524874 A1 | 9/1995 |
| WO | 9716129 A1 | 5/1997 |
| WO | 0013616 A1 | 3/2000 |
| WO | 0170143 A1 | 9/2001 |
| WO | 209623 | 2/2002 |
| WO | 03068119 A2 | 8/2003 |
| WO | 2004001569 A2 | 12/2003 |
| WO | 2005009298 A1 | 2/2005 |
| WO | 2005025451 A2 | 3/2005 |
| WO | 2005037065 A2 | 4/2005 |
| WO | 2005044150 A1 | 5/2005 |
| WO | 2005069957 A2 | 8/2005 |
| WO | 2006074503 A1 | 7/2006 |
| WO | 2006078511 A1 | 7/2006 |
| WO | 2006078528 A2 | 7/2006 |
| WO | 2006078864 A1 | 7/2006 |
| WO | 2006106419 A2 | 10/2006 |
| WO | 2006112911 A2 | 10/2006 |

OTHER PUBLICATIONS

"The Oxford Partial Knee", Biomet Patients and Caregivers-Joint Replacement, www.biomet.com/patients/oxford.cfm, Biomet, Inc. 2008, 3 pages.

"Preservation Uni-compartmental Knee", DePuy Orthopaedics, Inc. 2002, 31 pages.

European Search Report for European Patent Application No. 08251213.8-2310, Jul. 9, 2008, 7 pgs.

European Search Report for European Patent Application No. 08251211.2-2310, Jul. 21, 2008, 7 pgs.

European Search Report for European Patent Application No. 08251209.6-2310, Jul. 9, 2008, 7 pgs.

Extended European Search Report for European Patent Application No. 10189881.5-2310, Feb. 17, 2011, 6 pgs.

Chinese First Office Action, Chinese Patent Application No. 200810128765.8, Aug. 15, 2011, 3 pages.

European Search Report for European Patent Application No. 10189885.6-2310, Mar. 18, 2011, 8 pages.

European Search Report for European Patent Application No. 08251210.4-2310, Jun. 20, 2008, 7 pages.

Chinese First Office Action, Chinese Patent Application No. 200810125845.8, Aug. 24, 2011, 7 pages.

Chinese First Office Action, Chinese Patent Application No. 200810128765.8, Aug. 15, 2011, 5 pages.

* cited by examiner

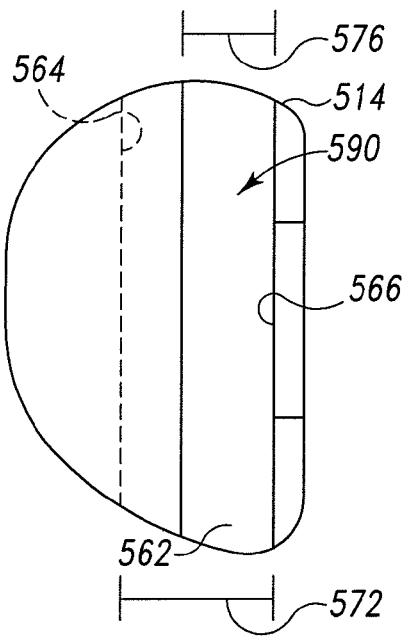
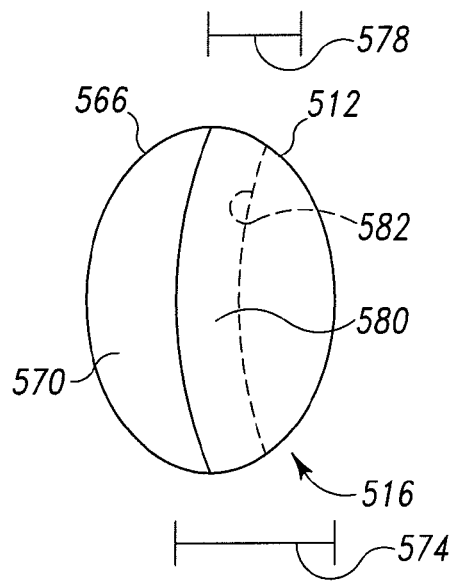
Fig. 30
Fig. 32
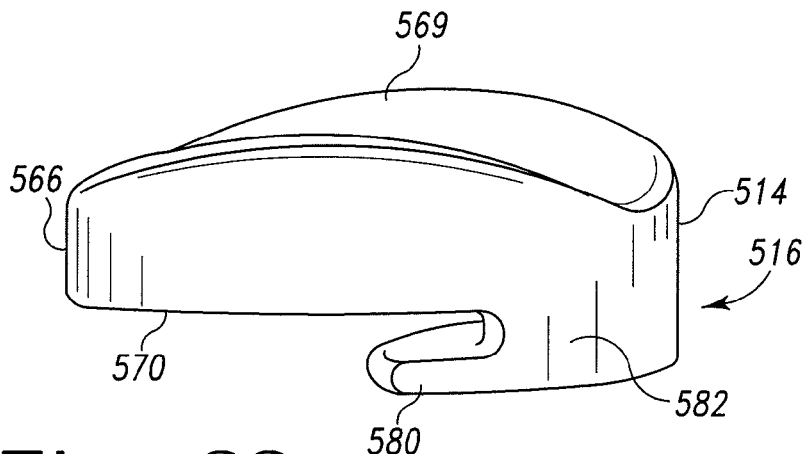
Fig. 33
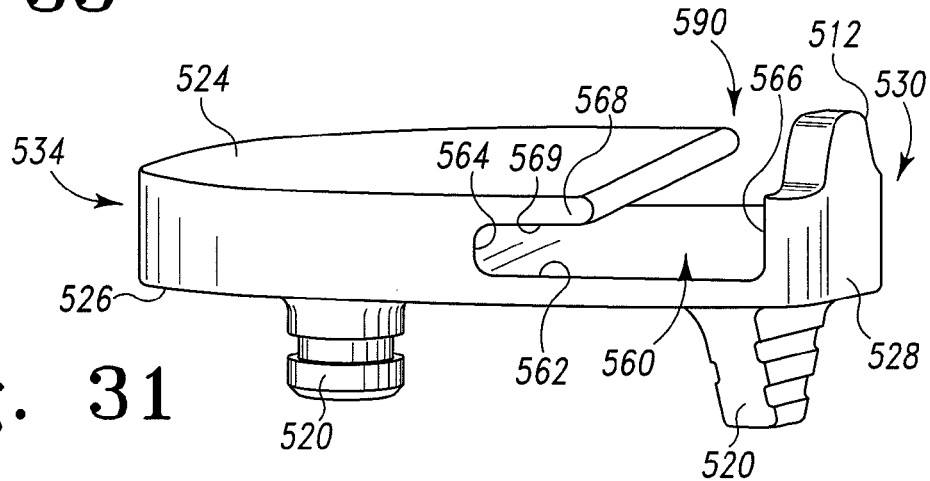
Fig. 31

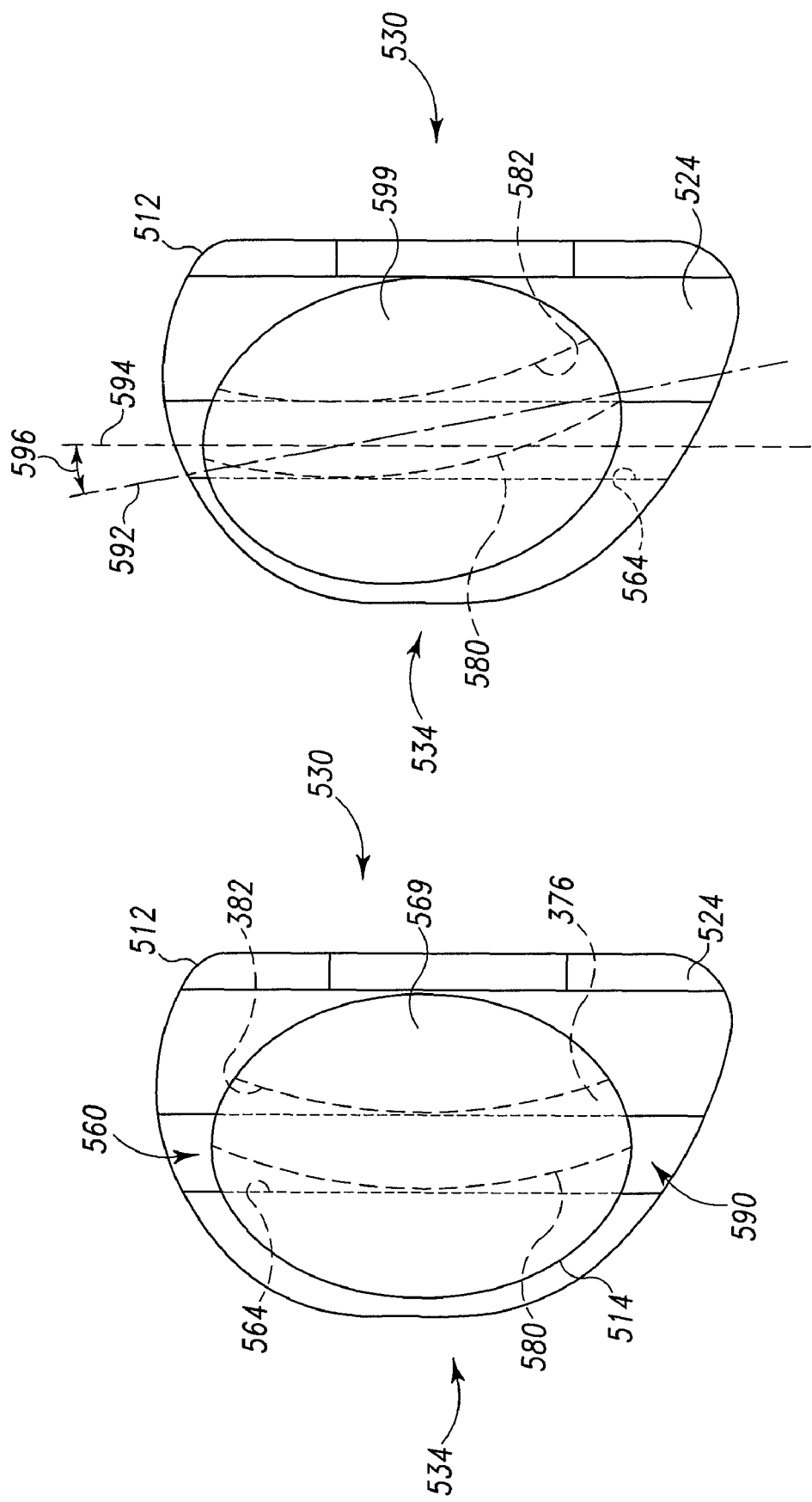

MOBILE BEARING ASSEMBLY HAVING A NON-PLANAR INTERFACE

This patent application claims priority to and the benefit of U.S. Provisional Patent Application Ser. No. 60/909,259 entitled "Mobile Bearing Assembly Having A Non-planar Interface" by Jordan S. Lee et al., which was filed on Mar. 30, 2007, the entirety of which is expressly incorporated herein by reference.

CROSS REFERENCE TO RELATED APPLICATIONS

Cross-reference is made to U.S. Utility patent application Ser. No. 12/049,753 entitled "MOBILE BEARING ASSEMBLY," which was filed on Mar. 17, 2008 by Jordan S. Lee et al., to U.S. Utility patent application Ser. No. 11/694,389 entitled "MOBILE BEARING ASSEMBLY HAVING OFFSET DWELL POINT," which was filed on Mar. 30, 2007 by Jordan S. Lee et al., to U.S. Utility patent application Ser. No. 12/049,750 entitled "MOBILE BEARING ASSEMBLY HAVING A CLOSED TRACK," which was filed on Mar. 17, 2008 by Joseph G. Wyss et al., and to U.S. Utility patent application Ser. No. 12/049,759 entitled "MOBILE BEARING ASSEMBLY HAVING MULTIPLE ARTICULATION INTERFACES," which was filed on Mar. 17, 2008 by Jordan S. Lee et al., the entirety of all of which is expressly incorporated herein by reference.

TECHNICAL FIELD

The present disclosure relates generally to orthopaedic prostheses, and particularly to tibial assemblies including a tibial tray and a tibial insert.

BACKGROUND

During the lifetime of a patient, it may be necessary to perform a joint replacement procedure on the patient as a result of, for example, disease or trauma. For example, many knee replacement surgeries are performed each year. Total knee replacement or arthroplasty may involve replacement of the mid-shaft portion of the femur, proximal, distal, and/or total femur, and proximal tibia. Unicompartmental knee replacement or arthroplasty involves unicondylar resurfacing. Unicompartmental knee arthroplasty provides an alternative to total knee arthroplasty for rehabilitating knees when only one condyle has been damaged as a result of trauma or disease such as noninflammatory degenerate joint disease or its composite diagnosis of osteoarthritis or post-traumatic arthritis. As such, unicompartmental knee arthroplasty may be indicated for use in patients undergoing surgery for a severely painful and/or disabled joint damaged as a result of osteoarthritis, traumatic arthritis, rheumatoid arthritis, or a failed previous implant when only one condyle of the knee (medial or lateral) is affected. Further, unicompartmental knee replacements may be "multi-piece" replacements in which a unicompartmental tibial insert is used to replace each of the medial and lateral condyles of the patient. A single, total femoral component or two partial femoral components may be used to cooperate with the two unicompartmental inserts.

In addition, in some knee replacement procedures, a total knee tibial tray may used with a unicompartmental tibial insert. For example, a total knee tibial tray may be used with a single unicompartmental tibial insert to replace either the medial or lateral condyle of the patient's knee. Alternatively, a total knee tibial tray may be used with two unicompartmental tibial inserts, each replacing one of the medial and lateral condyles of the patient's knee. In such applications, the medial and lateral unicompartmental tibial inserts may have different characteristics and be selected based on the orthopaedic considerations associated with the respective condyle of the patient's knee.

Unicompartmental knee replacements are intended to provide increased patient mobility and reduce pain by replacing the damaged knee joint articulation in patients where there is evidence of sufficient sound bone to seat and support the components. Age and activity level factor into all reconstructive procedures and the state of the arthritis determines the treatment. With the advancement of minimally invasive techniques that support unicompartmental knee reconstruction, a growing number of patients are offered this alternative for relief from the disabling pain of arthritis and for the potential benefits of a rapid recovery.

A tibial assembly of a unicompartmental knee prosthesis typically includes a tibial tray configured to be coupled to the patient's tibia and a polymer tibial bearing or insert adjacent the tibial tray. As discussed above, the tibial tray may be a total or unicompartmental tibial tray. The tibial insert includes an upper bearing surface configured to engage a corresponding articulating condylar surface of a femoral component coupled to the patient's femur. A mobile tibial assembly generally refers to a tibial assembly wherein the tibial insert is movable relative to the tibial tray. In other words, the tibial insert may rotate relative to the tray and/or the tibial insert may move medially, laterally, anteriorly, and/or posteriorly relative to the tibial tray. This motion of the tibial insert relative to the tray may be constrained in any number of ways in order to limit the type of motion of the tibial insert. For example, the tibial insert may be limited to anterior/posterior motion relative to the tibial tray and/or rotation of the tibial insert relative to the tibial tray may be limited to something less than 360 degree rotation. A fixed tibial assembly generally refers to a tibial assembly wherein the tibial insert is not movable relative to the tibial tray and remains in a fixed location thereon. Surgeons may choose between fixed and mobile tibial assemblies depending upon the particular needs of the patient.

Typical mobile tibial assemblies fall into one of two classifications with respect to the insert-to-tray interface: unconstrained and constrained. In an unconstrained mobile tibial assembly, the tibial insert is free to move in all directions relative to the tibial tray. In a constrained mobile tibial assembly, the tibial insert is typically restricted from movement relative to the tibial tray in all but one or more directions and/or movements (e.g., translations and/or rotations).

SUMMARY

According to one aspect, a unicompartmental mobile tibial assembly may include a tibial tray and a tibial insert. The tibial tray may be configured to be coupled to a surgically-prepared surface of the proximal end of a tibia. The tibial tray may include an upper surface and a bottom surface. The bottom surface of the tibial tray may be configured to engage a portion of the surgically-prepared surface of the tibia when coupled thereto. The tibial insert may be configured to be coupled to the tibial tray. The tibial insert may include an upper bearing surface and a bottom bearing surface. The upper bearing surface of the tibial insert may be configured to engage a surgically-prepared surface of the distal end of a femur. The bottom bearing surface of the tibial insert may be configured to engage the upper surface of the tibial tray when the tibial insert is coupled to the tibial tray. The tibial insert may be movable relative to the tibial tray. Any one or more of the upper surface of the tibial tray, the bottom surface of the tibial tray, and/or the bottom surface of the tibial insert may be non-planar.

In some embodiments, the bottom surface of the tibial tray may include a first planar surface portion and a second planar surface portion. The first planar surface portion is oblique relative to the second planar surface portion. Additionally, in some embodiments, the bottom surface of the tibial tray may include a third planar surface portion. The third planar surface portion may be oblique to the second planar surface portion and/or the first planar surface portion.

As discussed above, the upper surface of the tibial tray may be non-planar in some embodiments. For example, the upper surface of the tibial tray may be convex or concave. In some embodiments, the upper surface of the tibial tray may be both longitudinally and latitudinally convex. Additionally or alternatively, as discussed above, the upper surface of the tibial tray may be non-planar in some embodiments. For example, the upper surface of the tibial tray may be concave or convex.

In some embodiments, the upper surface of the tibial tray may be convex and the bottom bearing surface of the tibial insert may be concave such that the convex upper surface of the tibial tray engages the concave bottom bearing surface of the tibial insert as the tibial insert is moved relative to the tibial tray. Alternatively, the upper surface of the tibial tray may be concave and the bottom bearing surface of the tibial insert may be convex such that the concave upper surface of the tibial tray engages the convex bottom bearing surface of the tibial insert as the tibial insert is moved relative to the tibial tray.

In some embodiments, the tibial tray may include a track defined in the upper surface. The track may include a non-planar bottom wall. For example, the bottom wall of the track may be latitudinally concave, longitudinally concave, or latitudinally and longitudinally concave. Additionally, in some embodiments, the tibial insert may include a stem. The stem may extend downwardly from the bottom bearing surface of the tibial insert. The stem may be configured to be received by the track of the tibial tray. In some embodiments, the stem may include a non-planar bottom wall configured to engage the non-planar bottom wall of the track when the stem is received by the track. For example, the non-planar bottom wall of the stem is convex. The stem may have a substantially hemispherical shape, a substantially spherical shape, an elliptical bottom profile when viewed in plan view, a circular bottom profile when viewed in plan view, and/or a polygonal bottom profile when viewed in plan view.

In some embodiments, the track of the tibial tray may include a first side wall, a second side wall, a first protrusion extending from the first side wall a first distance over a portion of the non-planar bottom wall, and a second protrusion extending from the second wall a second distance over a portion of the non-planar bottom wall a second distance greater than the first distance. The first and the second protrusions may define an opening therebetween. In such embodiments, the stem of the tibial insert may include a flange defined at a distal end. The flange may have a bottom surface configured to engage the non-planar bottom wall of the track of the tibial tray when the stem is received thereby. The flange may also have a top surface configured to engage a bottom surface of at least one of the first protrusion and the second protrusion of the track of the tibial tray when the stem is received thereby. Additionally or alternatively, the flange may have a first distal end and a second distal end extending from a central axis of the stem. The second distal end may extend from the from the stem farther than the first distal end. The first protrusion of the track may be configured to engage a portion of the first distal end of the flange and the second protrusion of the track may be configured to engage a portion of the second distal end of the flange. In some embodiments, the first protrusion may extend from the first wall a first distance and the second protrusion extends from the second wall a second distance. The second distance being greater than the first distance.

According to another aspect, a method for implanting a unicompartmental tibial assembly may include securing a tibial tray to a surgically-prepared surface of the proximal end of a tibia. The tibial tray having a non-planar upper surface. The method may also include engaging a non-planar bottom surface of a tibial insert to the non-planar upper surface of the tibial tray. Additionally, in some embodiments, the method may include resecting a portion of the tibia such that the surgically prepared surface of the tibia is non-planar. In such embodiments, the tibial tray may be secured by engaging a non-planar bottom surface of the tibial tray to the non-planar surgically prepared surface of the tibia.

According to yet another aspect, a mobile tibial assembly may include a tibial tray configured to be coupled to a surgically-prepared surface of the proximal end of a tibia and a tibial insert configured to rest on the tibial tray. The tibial tray may include a platform having an upper surface. The tibial tray may also include an anchor extending downwardly from a bottom surface of the platform and a channel formed in the upper surface of the platform. The channel of the tibial tray may be generally parallel to an inboard surface of the platform of the tibial tray and may extend from an anterior side of the platform to a posterior side of the platform. The tibial insert may include a platform and a stem. The stem may extend downwardly from the platform. The stem may also be received within the channel of the tibial tray. The stem may include a medial surface defining a curved line extending from the anterior side of the tibial insert to the posterior side of the tibial insert when viewed in a plan view. The tibial assembly may be a unicompartmental tibial assembly. In some embodiments, the stem of the tibial tray may include a body extending from the anterior side of the tibial insert to the posterior side of the tibial insert and a flange coupled to the body and also extending from the anterior side of the tibial insert to the posterior side of the tibial insert.

In some embodiments, a top surface of the foot is spaced-apart from a bottom surface of the platform of the tibial insert to define a slot therebetween. The illustrative slot is curved when viewed in a plan view and extends from the anterior side of the tibial insert to the posterior side of the tibial insert. Additionally, the platform of the tibial tray may include a lip configured to define an undercut of the channel. The flange of the stem may be received within the undercut of the channel.

According to still another aspect, a mobile tibial assembly may include a tibial tray configured to be coupled to a surgically-prepared surface of the proximal end of a tibia. The assembly may also include a tibial insert configured to rest on the tibial tray. The tibial tray may include a platform having an upper surface. The tibial tray may also include an anchor extending downwardly from a bottom surface of the platform and a channel formed in the upper surface of the platform. The channel may be generally parallel to an inboard surface of the platform of the tibial tray and may extend from an anterior side of the platform to a posterior side of the platform. The tibial insert may include a platform and a stem. The stem may extend downwardly from the platform and be received within the channel of the tibial tray. The stem of the tibial insert may include a narrowed neck extending downwardly from the bottom surface of the platform of the tibial insert and a spherical body coupled to the narrowed neck and configured to be received within the channel. The channel of the tibial tray may be generally circular in shape when in viewed in cross-section.

According to yet a further aspect, a mobile tibial assembly may include a tibial tray configured to be coupled to a surgically-prepared surface of the proximal end of a tibia. The tibial tray may also include a tibial insert configured to rest on the tibial tray. The tibial tray may include a platform having an upper surface. The tibial tray may also include an anchor extending downwardly from a bottom surface of the platform and a channel formed in the upper surface of the platform. The channel of the tibial tray may be generally parallel to an inboard surface of the platform of the tibial tray and may extend from an anterior side of the platform to a posterior side of the platform. The tibial insert may include a platform and a stem. The stem may extend downwardly from the platform and be received within the channel of the tibial tray. In some embodiments, the stem of the tibial insert is dome-shaped.

BRIEF DESCRIPTION OF THE DRAWINGS

The detailed description particularly refers to the following figures, in which:

FIG. 30 is a top plan view of one embodiment of a tibial tray of the tibial assembly of FIG. 29;

FIG. 31 is an end view of the tibial tray of FIG. 30;

FIG. 32 is a bottom plan view of one embodiment of the tibia insert of the tibial assembly of FIG. 30;

FIG. 33 is an end view of the tibial insert of FIG. 32;

FIG. 34 is a top view of the tibial assembly of FIG. 30 in an assembled configuration having the tibial insert in an initial position relative to the tibial tray;

FIG. 35 is a top view of the tibial assembly of FIG. 30 in an assembled configuration having the tibial insert in another position relative to the tibial tray;

DETAILED DESCRIPTION OF THE DRAWINGS

Figure 1:
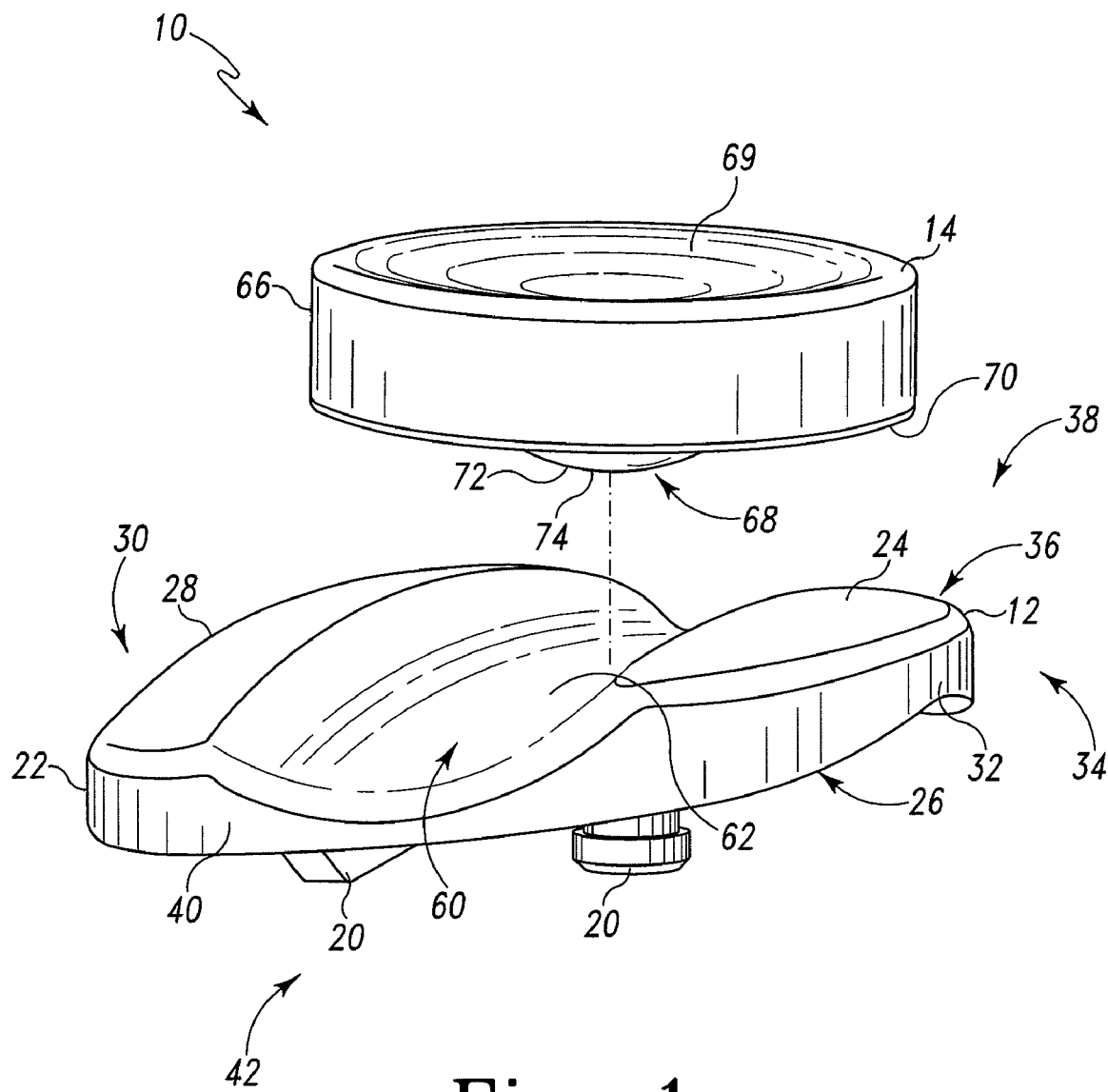
FIG. 1 is an exploded perspective view of an embodiment of a unicompartmental tibial assembly.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

A number of different embodiments of tibial assemblies are described below. Illustratively, the tibial assemblies are illustrated and described as unicompartmental tibial assemblies intended to replace only one of the two bearing surfaces of a patient's tibia. As such, the tibial assemblies may be used by an orthopaedic surgeon or other healthcare provider during the performance of a unicompartmental knee arthroplasty (UKA) procedure. However, it should be appreciated that the tibial assemblies described herein may also be used during the performance of a total knee arthroplasty (TKA) procedure. For example, a single tibial assembly may be used for each bearing surface of the tibia thereby improving the overall customizability of the orthopaedic implant compared to typical total knee arthroplasty implants. Additionally, the tibial assemblies described herein may be used by the surgeon or other healthcare provider during the performance of an orthopaedic surgical procedure using either conventional or minimally invasive surgical methods. Further, although the features of the tibial assemblies are described in reference to an orthopaedic knee implant, it should be appreciated that such features are applicable to other types of orthopaedic implants including, but not limited to, hip implants, shoulder implants, elbow implants, spine implants, finger implants, toe implants, wrist implants, and ankle implants.

Referring now to FIGS. 1-6, in one embodiment, a tibial assembly 10 includes a tibial tray 12 and a bearing, herein referred to as tibial insert 14. The tibial insert 14 is illustratively formed from a polymer material, but may be formed from other materials, such as a ceramic material, a metallic material, a bio-engineered material, or the like, in other embodiments. Similarly, the tibial tray 12 is illustratively formed from a metallic material, but may be formed from other materials, such as a ceramic material, a polymer material, a bio-engineered material, or the like, in other embodiments.

Figure 2:
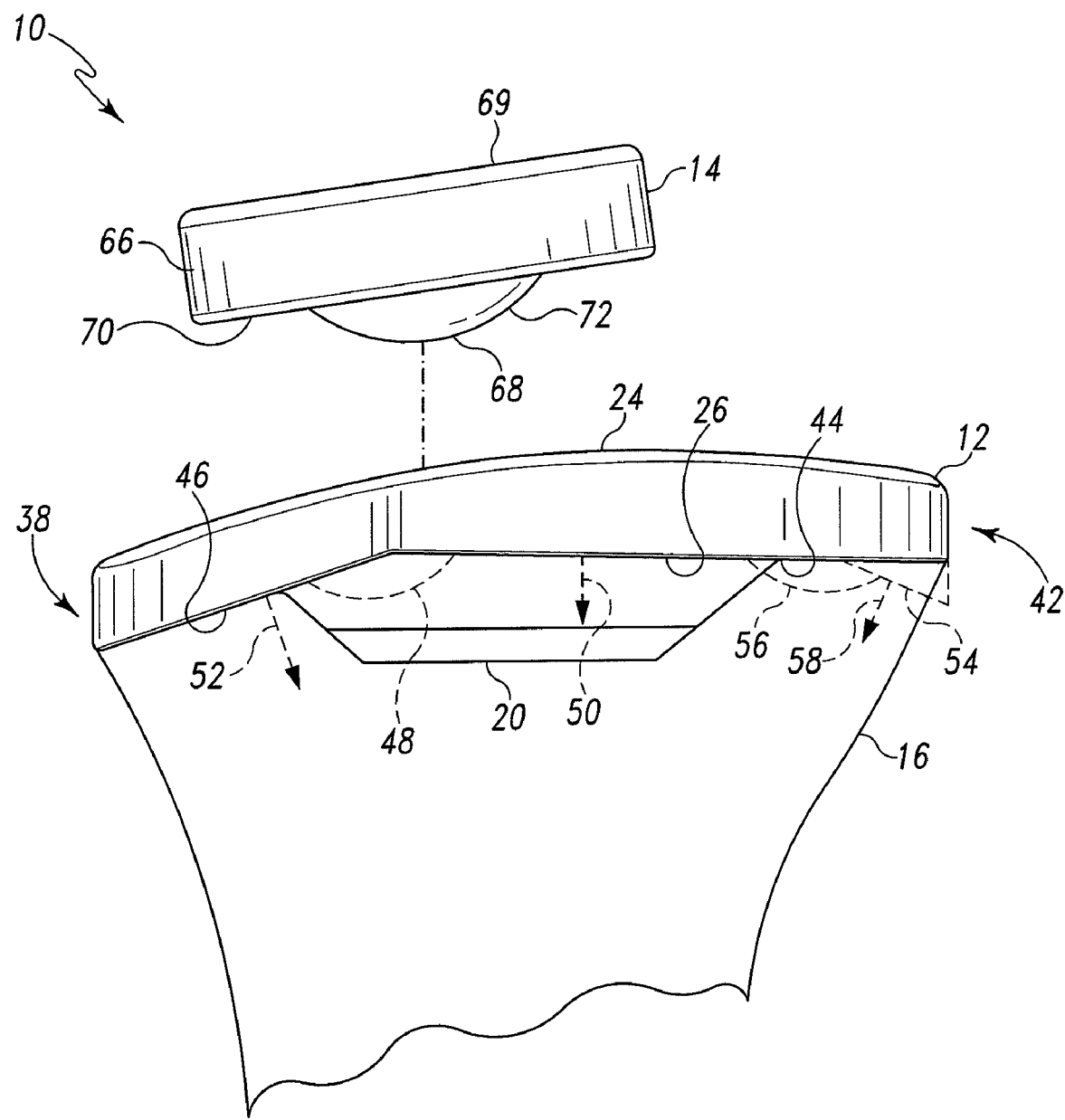
FIG. 2 is an exploded side elevation view of the unicompartmental tibial assembly of FIG. 1.

The tibial tray 12 is configured to be coupled to a surgically-prepared surface of the proximal end of a patient's tibia 16 as illustrated in FIG. 2. The tibial tray 12 includes a base 22 and a number of anchoring devices 20, commonly referred to as stems or keels, extending downwardly therefrom. When the tibial tray 12 is coupled to the patient's tibia 16, the anchoring devices 20 are embedded in the patient's tibia 16 to thereby secure the tibial tray 12 to the patient's bone.

The base 22 has a generally "D"-shaped top profile and includes an upper surface 24 and a bottom surface 26 from which the anchoring devices 20 extend. The base 22 has a generally straight outer surface 28 defining an inboard side 30 of the tibial tray 12, a generally curved outer surface 32 defining an outboard side 34 of the tibial tray 12, an end surface 36 defining an anterior side 42 of the tibial tray 12, and an end surface 40 defining a posterior side 38 of the tibial tray 12. It should be appreciated that the illustrative tibial assembly 10 is but one embodiment of a tibial assembly and that the features and components of the tibial assembly 10 may be used with a tibial assembly configured to replace the medial and/or lateral condyle of a patient's right tibia, as well as, the medial and/or lateral condyle of the patient's left tibia.

In the illustrative embodiment, the upper surface 24 of the tibial tray 12 is non-planar. That is, the upper surface 24 has a convex shape or is otherwise curved. The upper surface 24 may be curved in a generally anterior-posterior direction, in a generally medial-lateral direction, or in both a generally anterior-posterior direction and a generally medial-lateral direction as is illustrated in the illustrative embodiment. As discussed below, the upper surface 24 of the tibial tray 12 is configured to contact or otherwise be positioned adjacent to a bottom surface 70 of the tibial insert 14.

As shown in FIG. 2, the tibial tray 12 is configured to be coupled to a surgically-prepared surface of the proximal end of the tibia 16. To facilitate the coupling of the tibial tray 12 to the tibia 16, the bottom surface 26 of the tibial tray 12 is non-planar. For example, as illustrated in FIG. 2, the bottom surface 26 may be defined by an anterior planar surface 44 positioned toward the anterior side 42 of the tibial tray 12 and a posterior planar surface 46 positioned toward the posterior side 38 of the tibial tray 12. The posterior planar surface 46 is oblique to the anterior planar surface 44 so as to form an angle 48 therebetween. The size of the angle 48 established between the surfaces 44, 46 is selected such that the downward force generated during patient use is transferred by each surface 44, 46 toward the center of the tibia 16. For example, as shown in FIG. 2, the anterior planar surface 44 transfers force generated during patient use downwardly toward the center of the tibia 16 as indicated via the force vector arrow 50. Similarly, the posterior surface 46 transfers the force generated during patient use downwardly toward the center of the tibia 16 as indicated by force vector arrow 52. In this way, the downward force of the tibial insert 14 generated during patient use is directed toward the center of the tibia 16 across substantially the entire bottom surface 26.

In some embodiments, the bottom surface 26 may be defined by more than two oblique planar surfaces. That is, the bottom surface 26 may be defined by any number of oblique planar surfaces. For example, in some embodiments, the bottom surface 26 may include an additional planar surface 54 located near the anterior edge of the tibial tray 12 as shown in phantom in FIG. 2. As with the planar surfaces 44, 46 described above, the planar surface 54 and the planar surface 44 define an angle 56 therebetween. Similar to the angle 48, the size of the angle 56 is selected such that the downward force generated during patient use is transferred by each surface 44, 56 toward the center of the tibia 16. For example, the surface 54 transfers the force generated during patient use downwardly toward the center of the tibia 16 as indicated by force vector arrow 58.

Either one or both of the angles 48, 56 may be tapered in some embodiments. That is, the line defined by the intersection of the planar surface 44 and planar surface 46 may not be straight in the medial-lateral direction. Similarly, the line defined by the intersection between the planar surface 44 and the planar surface 54 may not be straight in the medial-lateral direction. Rather any one or both of the defined intersection lines may be curved or otherwise angled in the medial-lateral direction. For example, one end of the line defined by the intersection of the planar surface 44 and planar surface 46 may be positioned more anteriorly than the opposite end or may be positioned more posteriorly than the opposite end. As such, the non-planar profile of the bottom surface 26 of the tibial tray 12 may be varied between the inboard side 30 and the outboard side 34.

Figure 3:
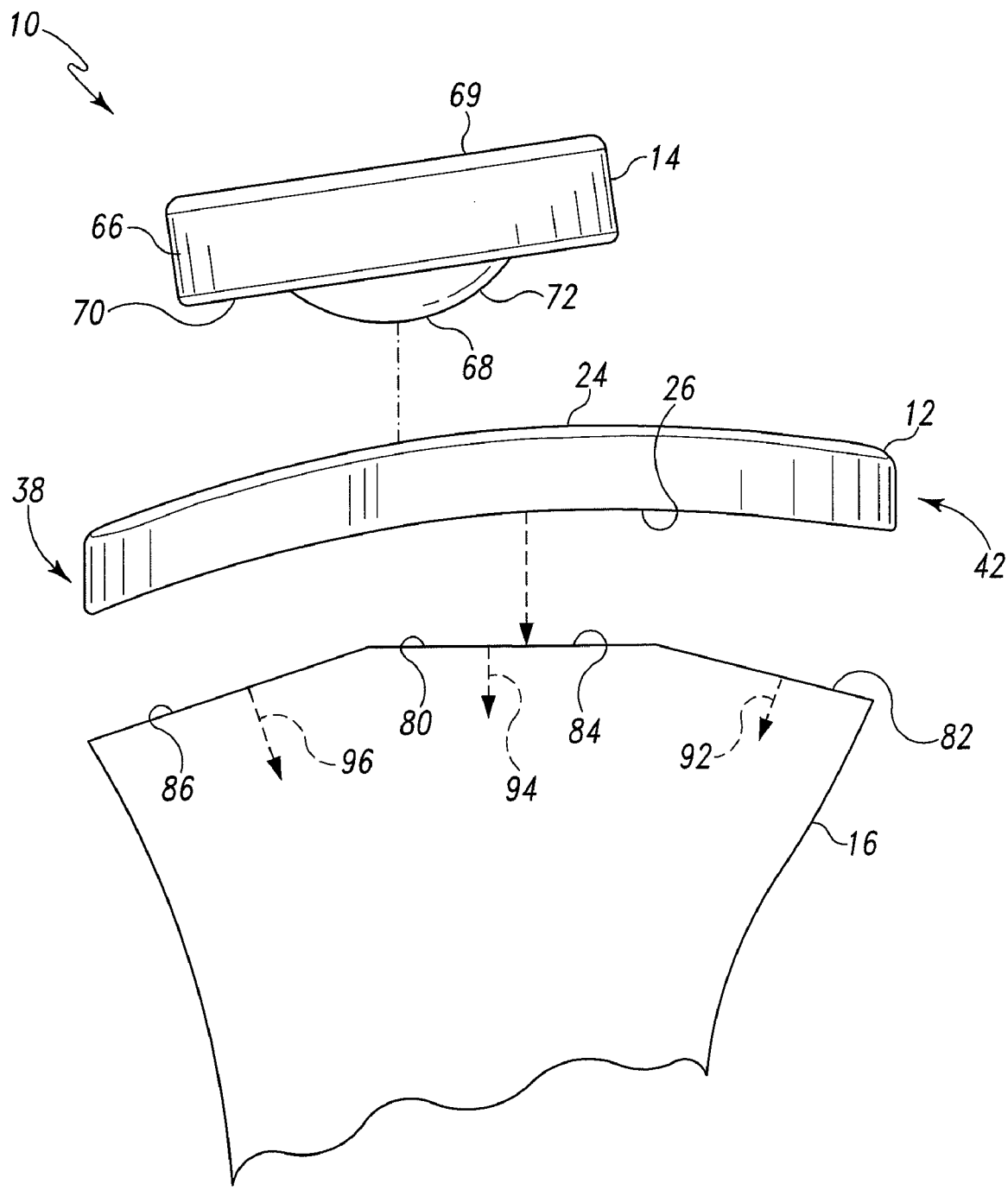
FIG. 3 is an exploded side elevation view of another embodiment of the unicompartmental tibial assembly of FIG. 1.

In other embodiments, the bottom surface 26 of the tibial tray 12 may be concavely curved or planar. In such embodiments, the patient's tibia 16 may be resected using a single planar cut or, as illustrated in FIG. 3, using a number of planar cuts, each cut being oblique to another. That is, the tibia 16 may be resected to have a top surface 80 configured to be coupled to the bottom surface 26 of the tibia tray 12 that is defined by a number of planar surfaces 82, 84, 86. Each of the planar surfaces 82, 84, 86 is oblique relative to each other. During the performance of the orthopaedic surgical procedure, the tibial tray 12 is coupled to the resected tibia 16 using a suitable adhesive such as bone cement. Because the adhesive is "form fitting" to the tibial tray 12 and the tibia 16, any space formed between the bottom surface 26 of the tibial tray 12 and the top surface 82 of the tibia 16 is substantially filled by the adhesive. Additionally, because the resected surface 80 of the tibia 16 is defined by a number of oblique, planar surfaces 82, 84, 86, the downward force exerted on each surface 82, 84, 86 via the tibial tray 12 is transferred toward the center of the tibia 16 as indicated in FIG. 3 via the force vector arrows 92, 94, 96. As such, it should be appreciated that any one of a number of embodiments may be used to direct the downward force exerted by the tibial tray 12 during use toward the center of the tibia 16. For example, in some embodiments, the bottom surface 26 of the tibial tray 12 may be non-planar or otherwise curved and the resected surface 80 of the tibia 16 may be substantially planar. Alternatively, the bottom surface 26 of the tibial tray 12 may be substantially planar and the resected surface 80 of the tibia 16 may be non-planar or otherwise curved. Further, the bottom surface 26 of the tibial tray 12 may be non-planar or otherwise curved and the resected surface 80 of the tibia 16 may also be non-planar or otherwise curved.

Referring back to FIG. 1, the tibial tray 12 includes a track 60 defined longitudinally in the base 22 in a generally anterior-posterior direction. As described below, the track 60 is configured to receive a stem 68 of the tibial insert. The illustrative track 60 is defined by a non-planar or otherwise curved bottom surface 62. The bottom surface 62 may be curved in the generally anterior-posterior direction, the generally medial-lateral direction, or in both the generally anterior-posterior direction and the generally medial-lateral direction. The illustrative track 60 is convex in the generally anterior-posterior direction and concave in the generally medial-lateral direction. Although the illustrative track 60 is concave or curved, tracks having other shapes and configurations may be used in other embodiments as discussed below.

Figure 4:
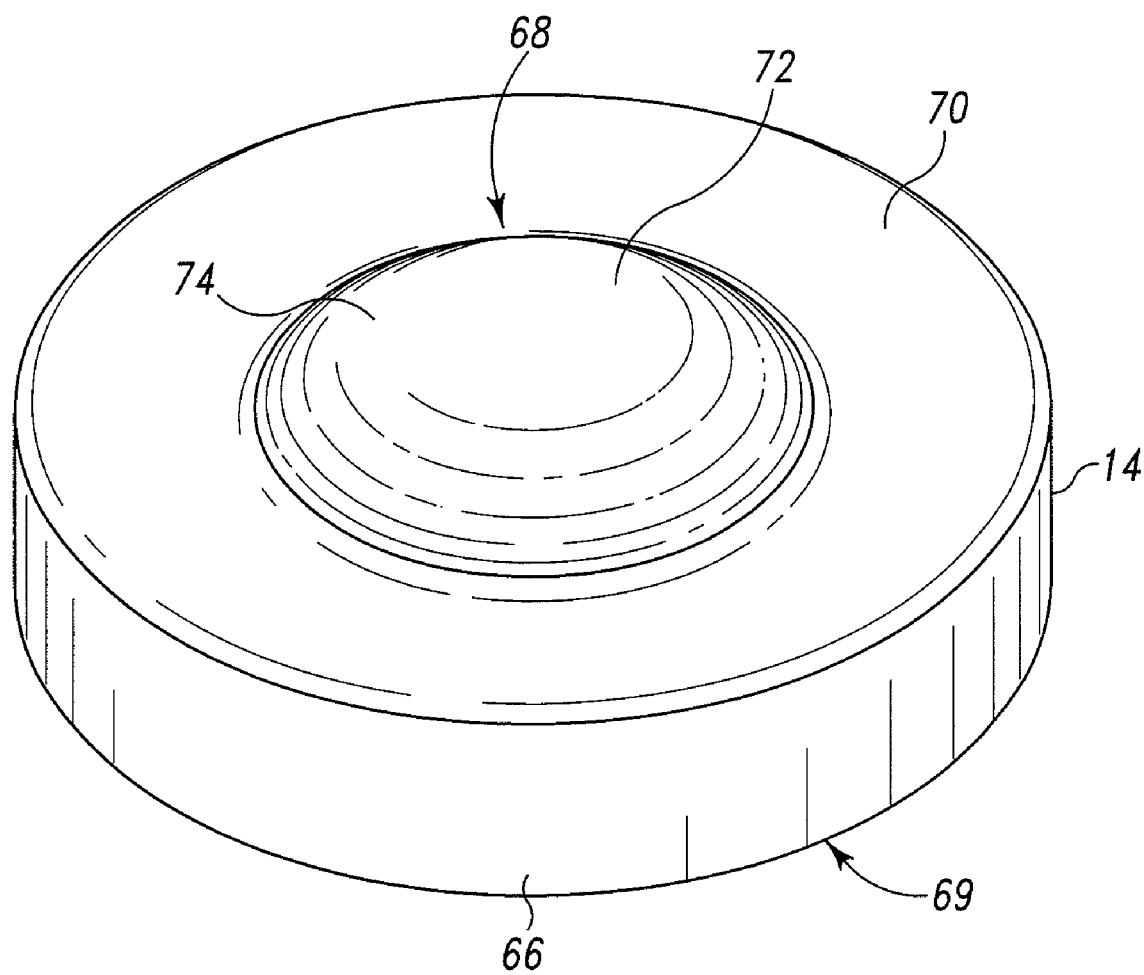
FIG. 4 is a bottom perspective view of one embodiment of a tibial insert of the unicompartmental tibial assembly of FIG. 1.
Figure 5:
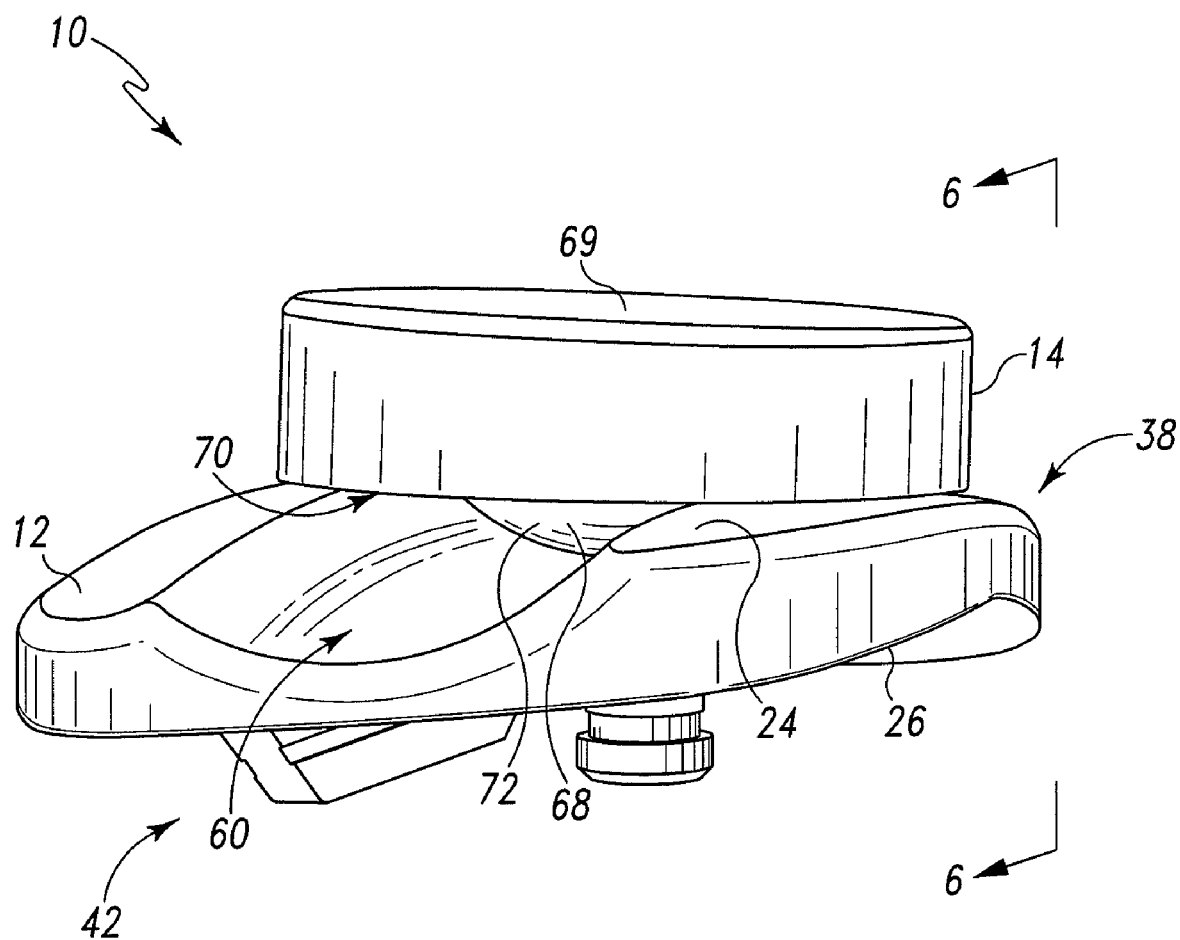
FIG. 5 is a perspective view of the unicompartmental tibial assembly of FIG. 1 in an assembled configuration.

The tibial insert 14 includes a base 66 and a stem 68 extending downwardly therefrom. The base 66 has an upper bearing surface 69 and a bottom surface 70. The upper bearing surface 69 of the tibial insert 14 is configured to engage a natural or prosthetic femoral condyle of a patient's femur. During use, the patient's femur or femoral component articulates on the upper bearing surface 69. The bottom surface 70 is configured to contact or otherwise be positioned adjacent to the upper surface 24 of the tibial tray 12 when coupled together as illustrated in FIG. 5. As such, the bottom surface 70 may be planar or non-planar (e.g., convex or concave) based upon the curvature of the upper surface 24 such that the bottom surface 70 is able to mate with the upper surface 24 during use. In the illustrative embodiment of FIGS. 1-6, the bottom surface 70 of the tibial insert 14 is concave as illustrated in FIG. 4 and is configured to contact or otherwise mate with the convex upper surface 24 of the tibial insert 14.

In the illustrative embodiment, the stem 68 is embodied as a bearing 72 extending downwardly from the curved bottom surface 70. The bearing 72 is configured to be received in the track 60 of the tibial tray and, as such, may have any configuration such that bearing 72 may be received therein. In the illustrative embodiment of FIGS. 1-6, the bearing 72 has a substantially convex shape. That is, the bearing 72 has a substantially hemi-spherical or otherwise spherical cap shape. As such, the bearing 72 has a curved outer surface 74 that is configured to contact or otherwise be positioned adjacent to the track's curved bottom surface 62 when the tibial insert 14 and the tibial tray 12 are coupled together.

Figure 6:
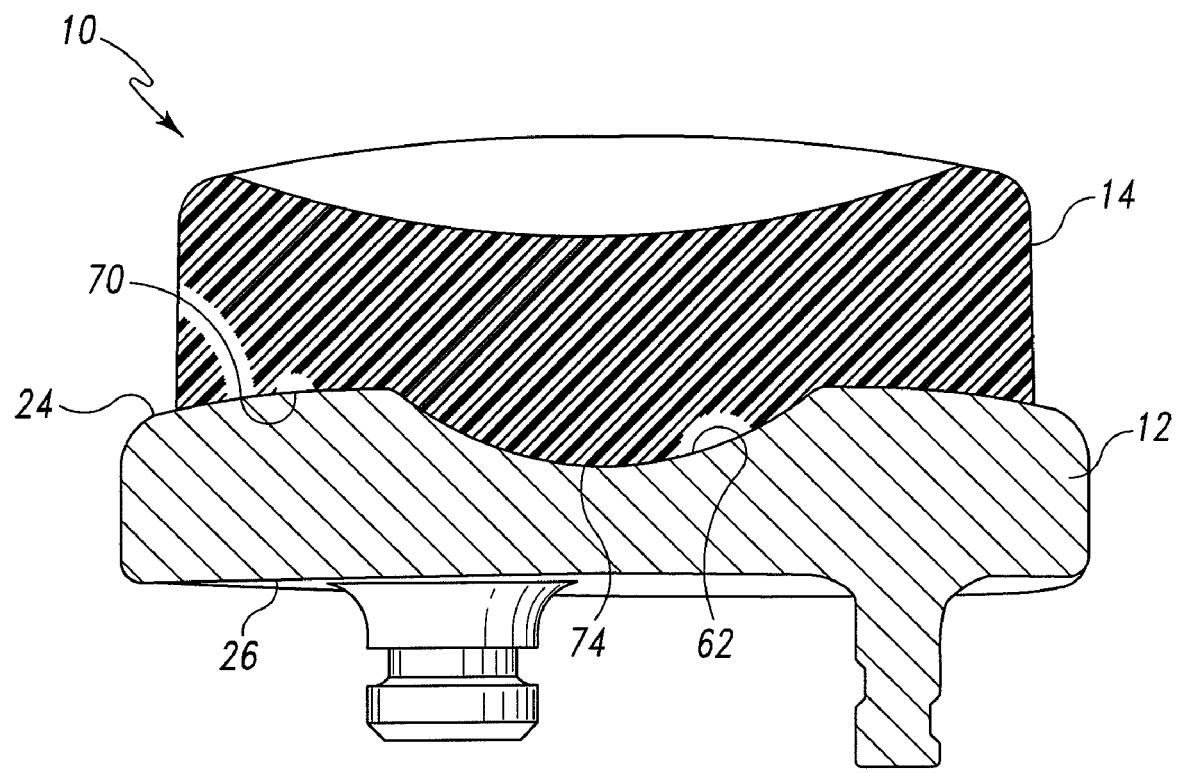
FIG. 6 is a cross-sectional view of the unicompartmental tibial assembly of FIG. 4 taken generally along the section lines 6-6.
Figure 7:
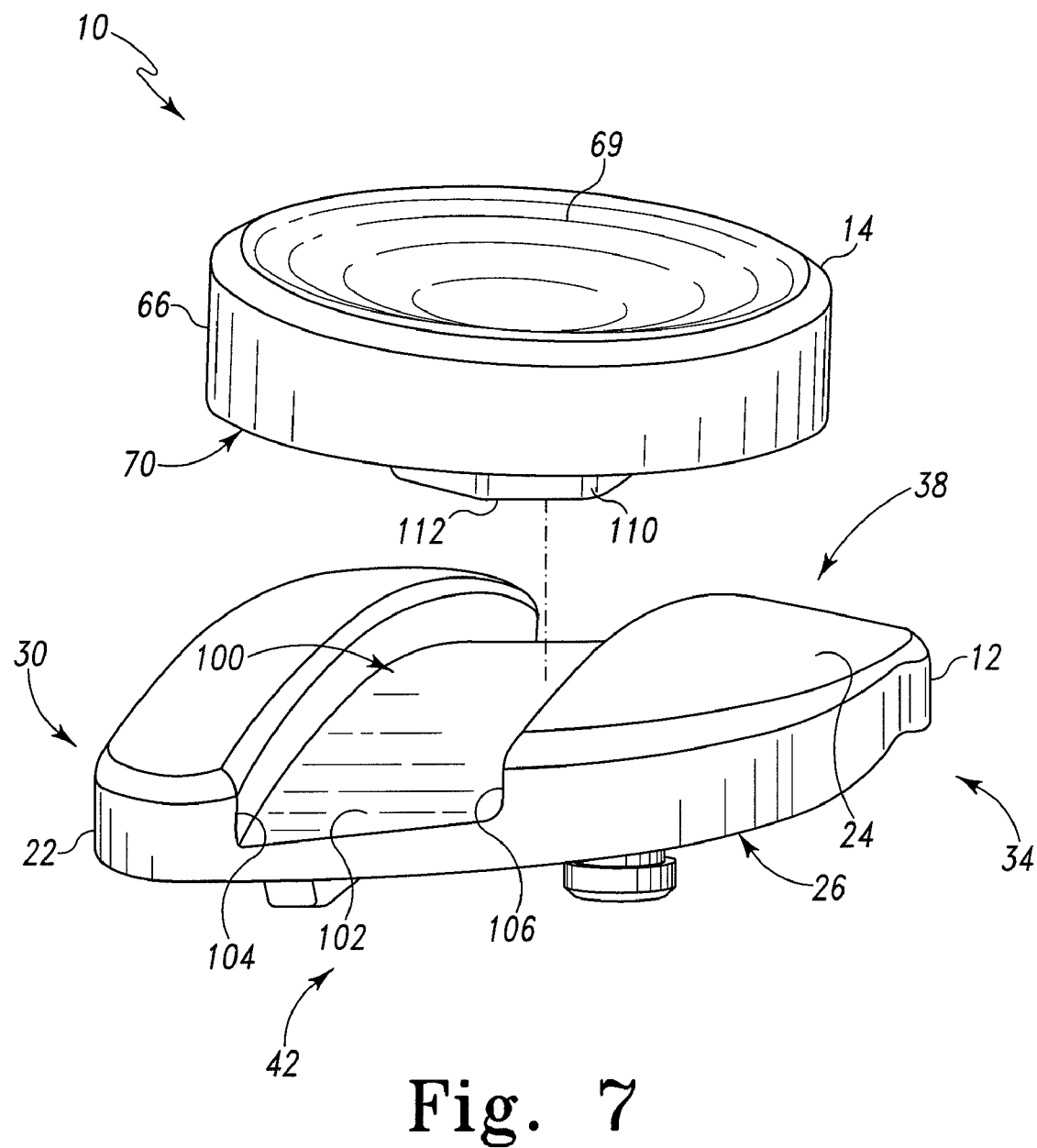
FIG. 7 is an exploded perspective view of another embodiment of a unicompartmental tibial assembly.
Figure 8:
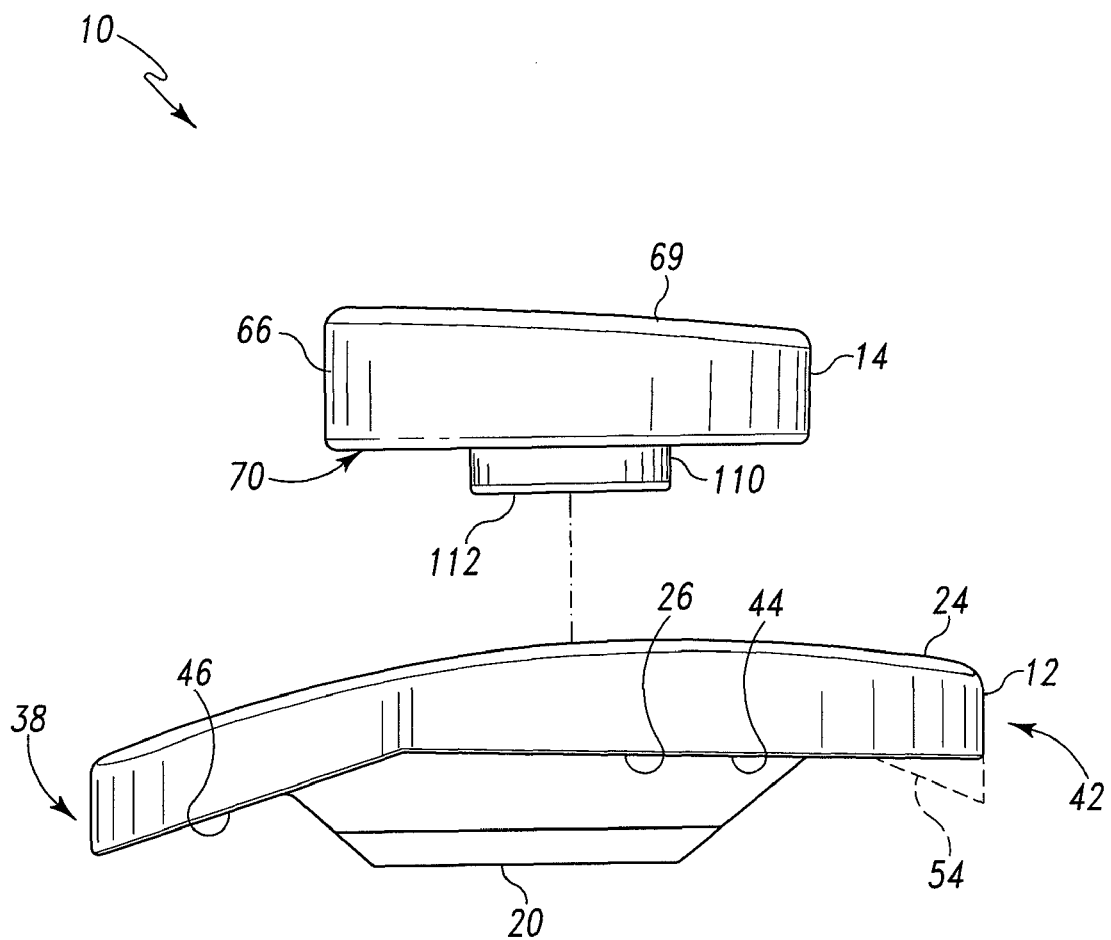
FIG. 8 is an exploded side elevation view of the unicompartmental tibial assembly of FIG. 7.

During the performance of the orthopaedic surgical procedure (e.g., a UKA or TKA procedure), the tibial insert 14 may be coupled to the tibial tray 12 by positioning the tibial insert 14 on the tibial tray 12 such that the bearing 72 of the insert 14 is received in the track 60 of the tray 12 as shown in FIGS. 5 and 6. When the tibial insert 14 is coupled to the tibial tray 12, the bottom surface 70 of the tibial insert 14 contacts or is otherwise adjacent to the upper surface 24 of the tibial tray 12. Because the bottom surface 70 of the tibial 12 is concave and the upper surface 24 of the tibial tray 12 is convex, the surfaces 24, 70 mate and thereby allow the tibial insert 14 to be moved relative to the tibial tray 12. In addition, the outer surface 74 of the bearing 72 contacts or is otherwise positioned adjacent the track's bottom surface 62 when the tibial insert 14 is coupled to the tibial tray 12. Again, because the outer surface 74 is convex and the bottom surface 62 is concave, the surfaces 62, 74 mate and thereby allow the tibial insert 14 to be moved relative to the tibial tray 12.

During patient use, the tibial insert 14 moves back and forth along the track 60 of the tibial tray 12 in a generally anterior-posterior direction. In embodiments wherein the bottom surface 26 of the tibial tray 12 is non-planar, the force exerted on the tibial tray is directed toward the center of the patient's tibia as discussed above. In addition, because the top surface 24 of the tibial tray 12 is non-planar, the force exerted on the tibial tray is further directed toward the center of the patient's tibia as tibial insert 14 moves across the top surface 24. Yet further, because the posterior side 38 of the tibial tray 12 is in a more inferior position than the anterior side 42 of the tibial tray 12 when coupled to the patient's tibia 16, the patient's tibia 16 moves in a downwardly direction when the patient's knee is in flexion relative to the extension position of the tibia. As such, the laxity of the knee joint is increased, which may increase the range of motion of the patient's knee. Further, because the bearing 72 is hemi-spherical or spherical cap in shape, the tibial insert 14 may be configured to rotate about a center axis defined by the bearing 72. As such, in use, the tibial insert 14 is configured to rotate while, or in addition to, moving anteriorly or posteriorly within the track 60.

Referring now to FIGS. 7-12, in another embodiment, the tribal tray 12 may include track 100 in place of the track 60. The track 100 is defined by a bottom wall 102 and side walls 104, 106. The side walls 104, 106 are substantially parallel to each other and extend upwardly from the bottom surface 102 in a substantially orthogonal orientation such that the track 100 defined thereby has a rectangular cross-section. As with the track 60, the bottom wall 102 may be non-planar or otherwise curved. In the illustrative embodiment, the bottom wall 102 is convex in the generally anterior-posterior direction and substantially planar or flat in the generally medial-lateral direction.

Figure 9:
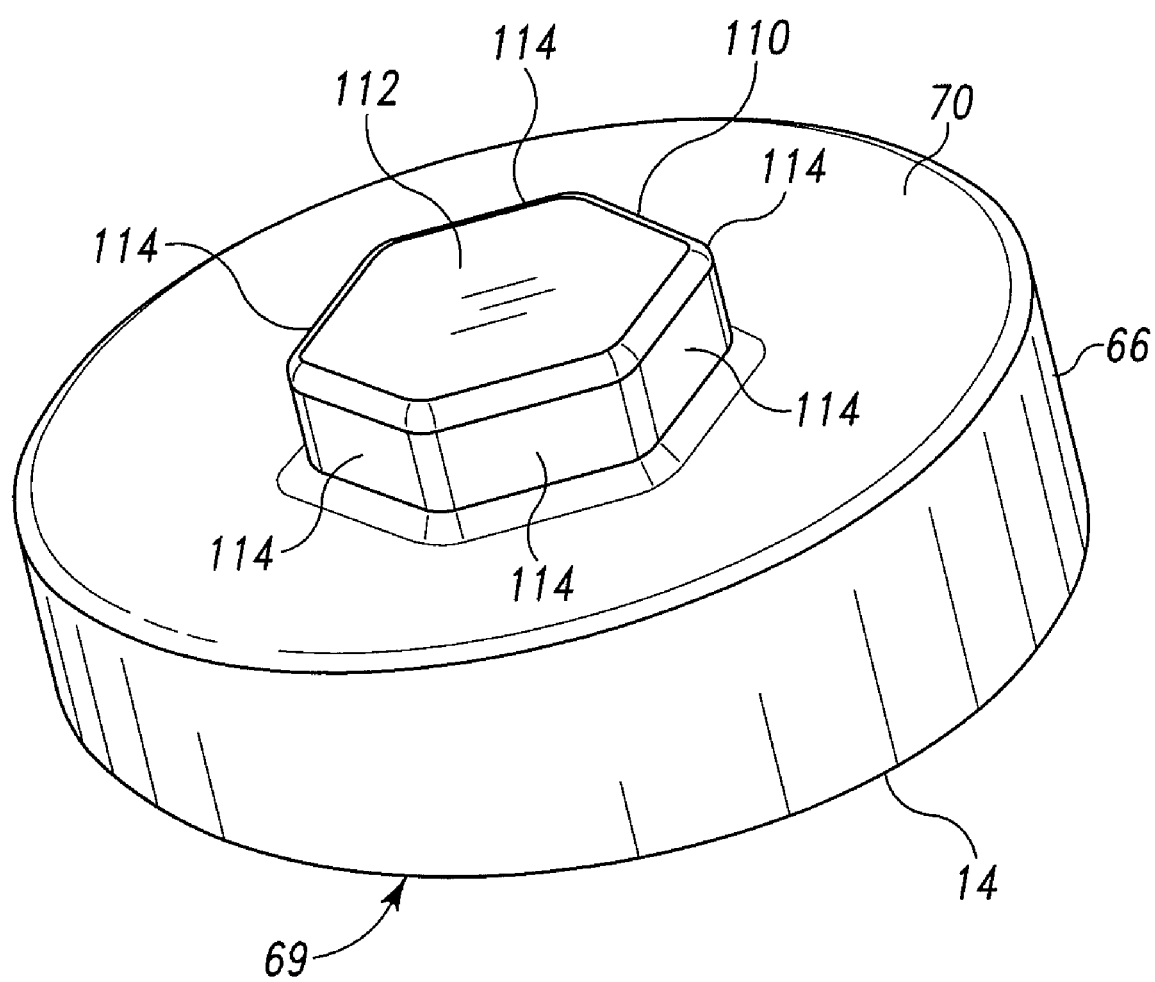
FIG. 9 is a bottom perspective view of one embodiment of a tibial insert of the unicompartmental tibial assembly of FIG. 7.
Figure 10:
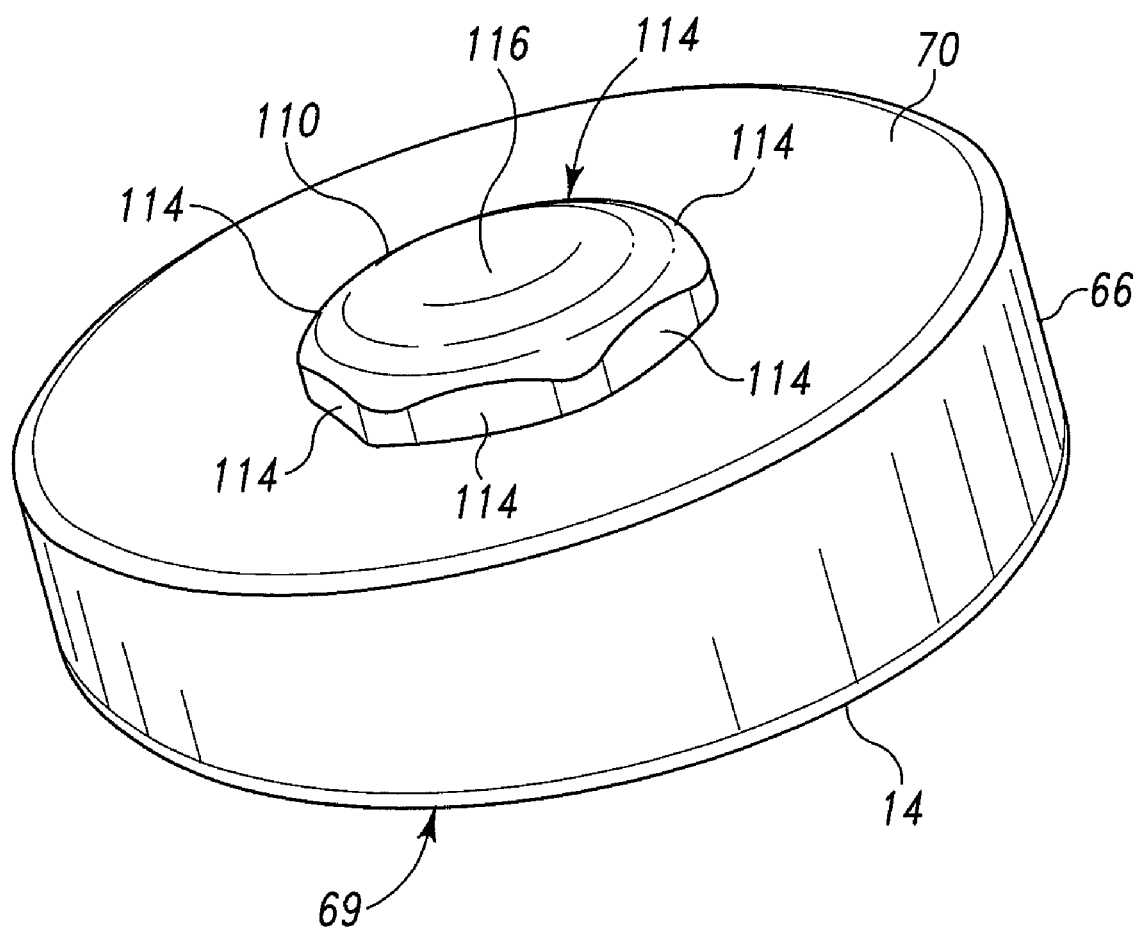
FIG. 10 is a bottom perspective view of another embodiment of the tibial insert of the unicompartmental tibial assembly of FIG. 7.

In embodiments in which the tibial tray 12 includes the track 100, the tibial insert 14 includes a stem 110 in place of the stem 68. The stem 110 has a hexagonal shape when viewed in the bottom plan view. The stem 110 includes a bottom surface 112 and six side surfaces 114 that cooperate to define the hexagonal shape as shown in FIG. 9. Although the illustrative stem 110 is hexagonal in shape, it should be appreciated that stems having other shapes may be used in other embodiments. The stem 110 is configured to be received by the track 100. As such, the bottom surface 112 of the stem 110 is substantially planar such that the bottom surface 112 is configured to contact or otherwise mate with the track's medially-laterally planar bottom wall 102. However, as illustrated in FIG. 10, in embodiments in which the track's bottom wall 102 is curved or otherwise non-planar, the stem 110 may include a bottom surface 116 that is also non-planar. For example, in embodiments wherein the track's bottom wall 102 is concave in the generally medial-lateral direction similar to the track 60 illustrated in and discussed above in regard to FIGS. 1-6, the bottom surface 116 may be convex such that the bottom surface 116 is able to contact or mate with the bottom wall 102.

Figure 11:
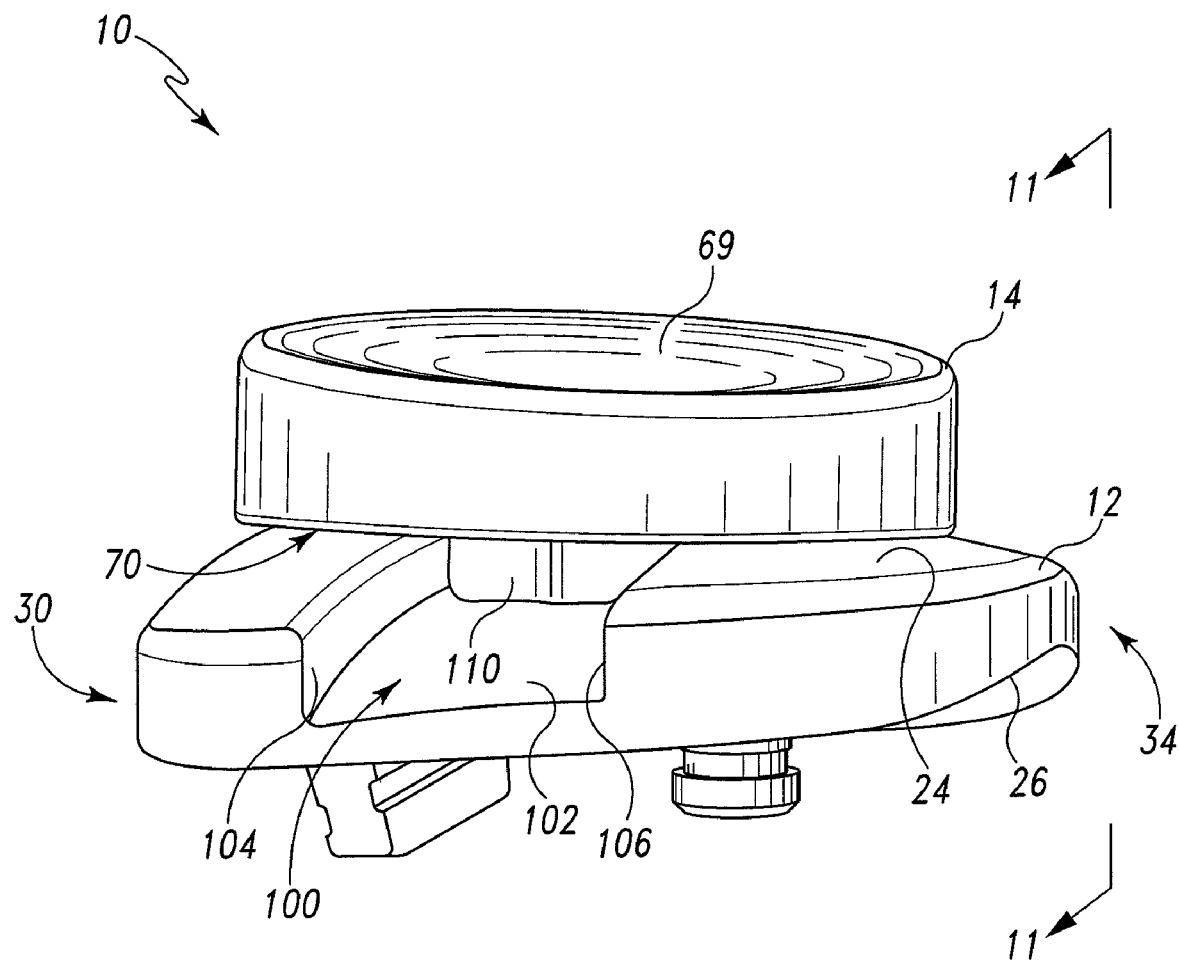
FIG. 11 is a perspective view of the unicompartmental tibial assembly of FIG. 7 in an assembled configuration.
Figure 12:
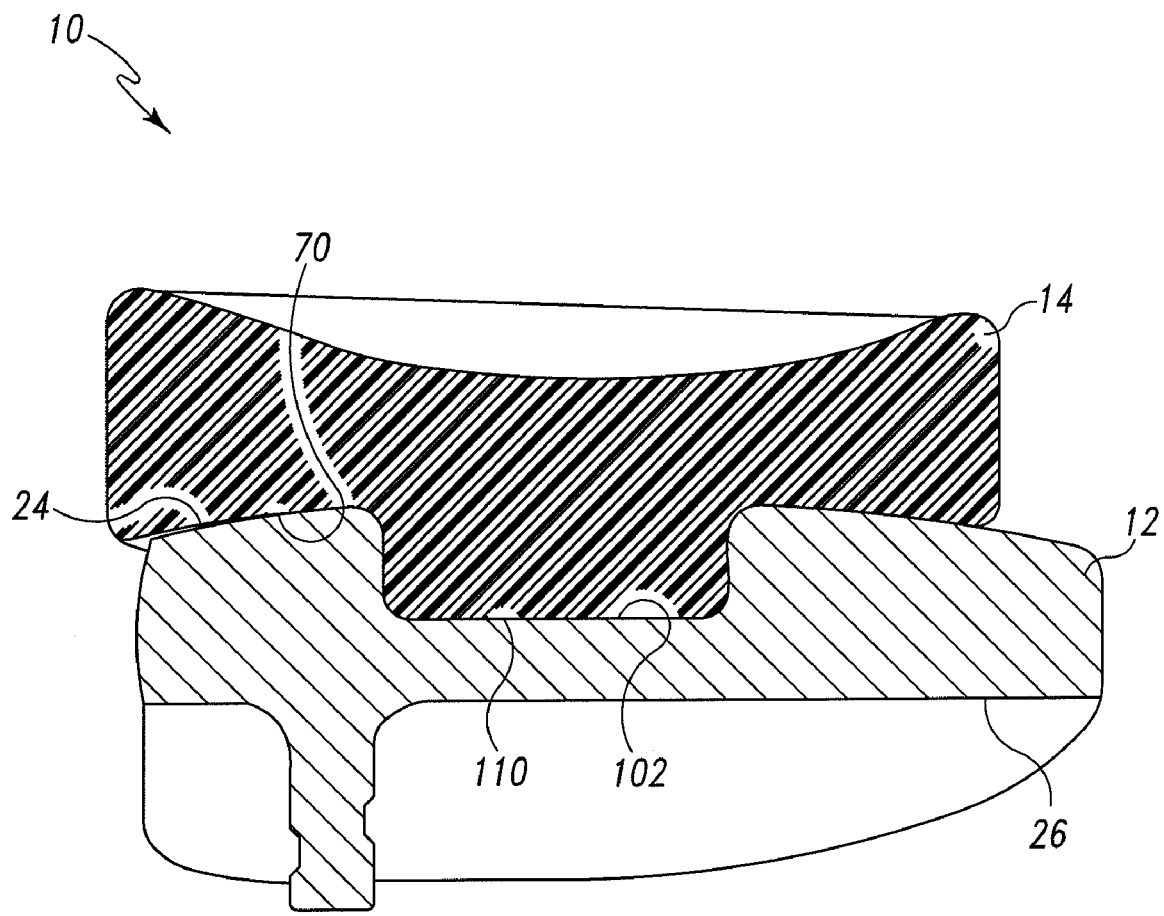
FIG. 12 is a cross-sectional view of the unicompartmental tibial assembly of FIG. 11 taken generally along the section lines 12-12.

During the performance of the orthopaedic surgical procedure (e.g., a UKA or TKA procedure), the tibial insert 14 may be coupled to the tibial tray 12 by positioning the tibial insert 14 on the tibial tray 12 such that the stem 110 of the insert 14 is received in the track 100 of the tray 12 as shown in FIGS. 11 and 12. As described above in regard to the embodiment of FIGS. 1-6, when the tibial insert 14 is coupled to the tibial tray 12, the bottom surface 70 of the tibial insert 14 contacts or is otherwise adjacent to the upper surface 24 of the tibial tray 12. Again, because the bottom surface 70 of the tibial insert 14 is concave and the upper surface 24 of the tibial tray 12 is convex, the surfaces 24, 70 mate and thereby allow the tibial insert 14 to be moved relative to the tibial tray. In addition, the bottom surface 112, 116 of the stem 110 contacts or is otherwise positioned adjacent the track's bottom wall 102 when the tibial insert 14 is coupled to the tibial tray 12. Because the bottom surface 112 is substantially planar and the track's bottom wall 102 is also substantially planar, the surface 112 and the wall 102 mate and thereby allow the tibial insert 14 to be moved relative to the tibial tray 12. Further, when the tibial insert 14 is coupled to the tibial tray 12, a parallel pair of the side walls 114 contact or are otherwise positioned adjacent the side walls 104, 106 of the track. Because the side walls 104, 106 and the sidewalls 114 are straight, the tibial tray 12 is prevented from rotating about the stem 112. However, because the stem 110 is hexagonal in shape, the tibial insert 14 may be coupled to the tray in one of six different configurations.

During patient use, the tibial insert 14 moves back and forth along the track 100 of the tibial tray 12 in a generally anterior-posterior direction. In addition, although the tibial insert is restricted from rotating about the stem 110 by the track's side walls 104, 106 and the stem's sidewalls 114, the tibial insert 14 may be positioned in any one of six different configurations relative to the tibial tray such that the positioning of any asymmetrical features of the tibial insert 14 may be customized to the particular patient.

Referring now to FIGS. 13-17, in another embodiment, the tribal tray 12 may include a track 200 in place of the track 60. The track 200 is defined by a bottom wall 202 and side walls 104, 106. An inboard lip 208 extends from the side wall 204 over a portion of the bottom wall 202. Similarly, an outboard lip 210 extends from the side wall 206 over a portion of the bottom wall 202. The lips 208, 210 define an elongated opening 212 in the upper surface 24 of the tibial tray 12. In the illustrative embodiment, the lips 208, 210 extend from the side walls 204, 206 respectively, an equal distance. However, in other embodiments, the lips 208, 210 may extend from the side walls 204, 206 different distances. The inboard lip 208 includes a bottom surface 214 and the outboard lip 210 includes a bottom surface 216. In the illustrative embodiment, the bottom surfaces 214, 216 are oblique or otherwise non-parallel to the track's bottom wall 202. However, in other embodiments, the bottom surfaces 214, 216 may be substantially parallel to the track's bottom wall 202.

As with the track 60, the bottom wall 202 of the track 200 may be planar or non-planar. In the illustrative embodiment, the bottom wall 202 of the track is substantially planar or flat in the generally medial-lateral direction, but convex in the generally anterior-posterior direction similar to the bottom wall 102 of the track 100 illustrated in and described above in regard to FIGS. 7-12.

Figure 13:
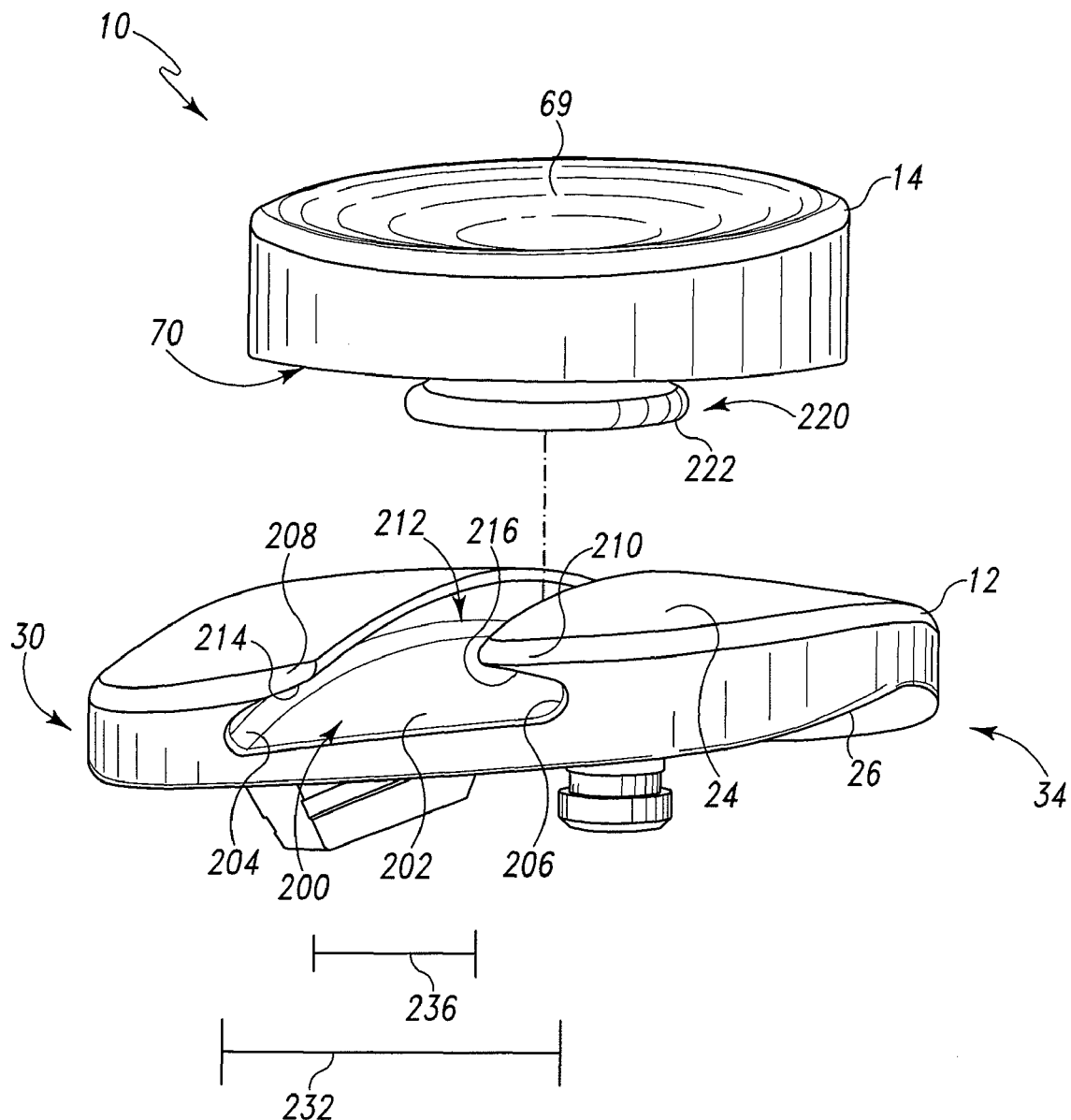
FIG. 13 is an exploded perspective view of another embodiment of a unicompartmental tibial assembly.
Figure 14:
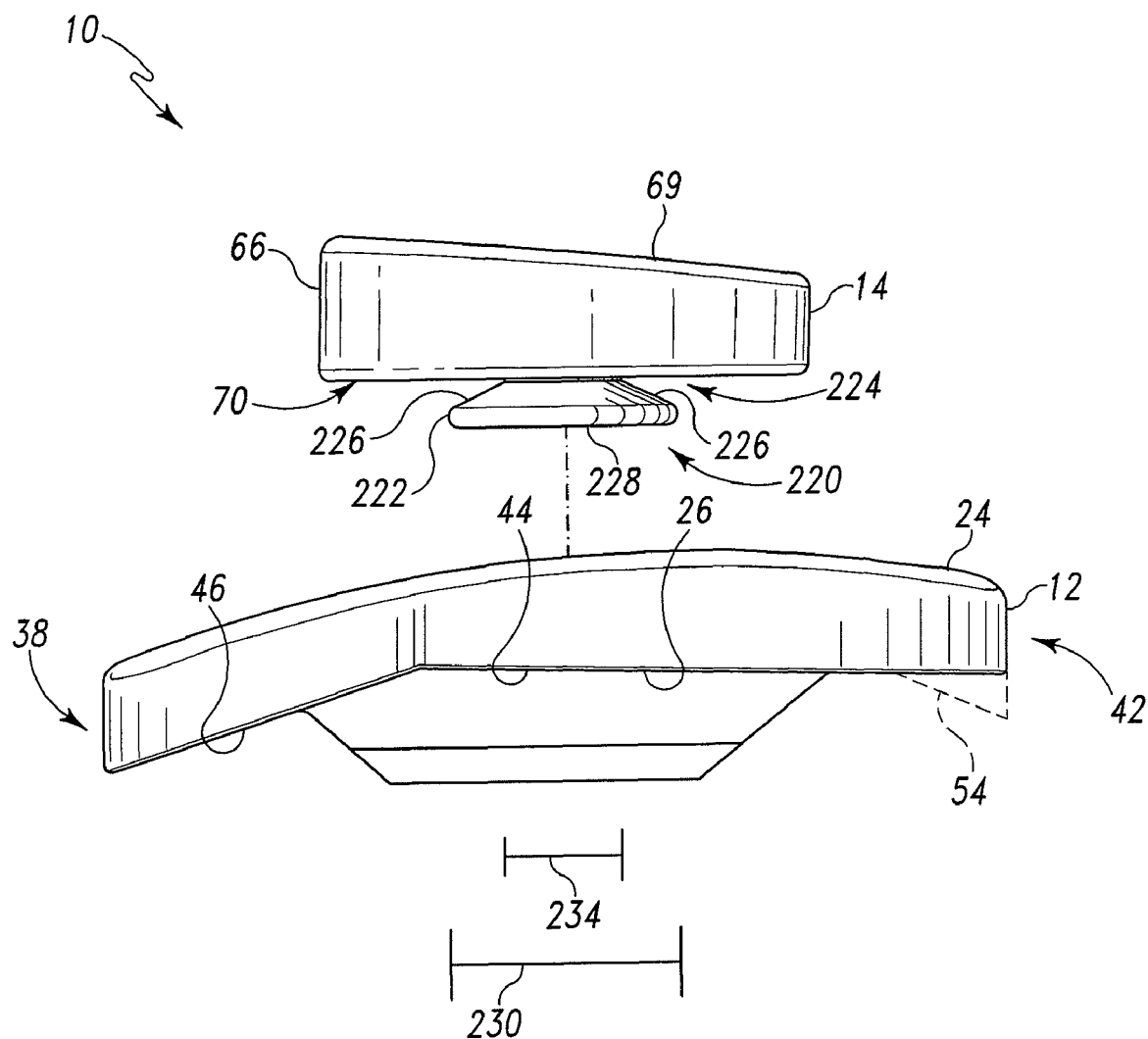
FIG. 14 is an exploded side elevation view of the unicompartmental tibial assembly of FIG. 13.

In embodiments in which the tibial tray 12 includes the track 200, the tibial insert 14 includes a stem 220 in place of the stem 68. The stem 220 includes a flange 222 and a neck 224 connecting the flange 222 to the bottom surface 70 of the base 66 of the tibial insert 14. As shown in FIGS. 13 and 14, the flange 222 has a width or diameter 230 that is slightly less than width 232 of the track's bottom wall 202. Similarly, the neck 224 has a width 234 that is slightly less than the width 236 of the elongated opening 212 defined between the lips 208, 210. As such, when the stem 220 is received by the track 200, the tibial insert 14 may be moved along the track 200. However, because the width 230 of the flange 222 is greater than the width 236 of the elongated opening 212, the tibial insert 14 is retained in the track 200 via the lips 208, 210 thereby preventing the tibial insert 14 from lifting off the tibial tray 12.

Figure 15:
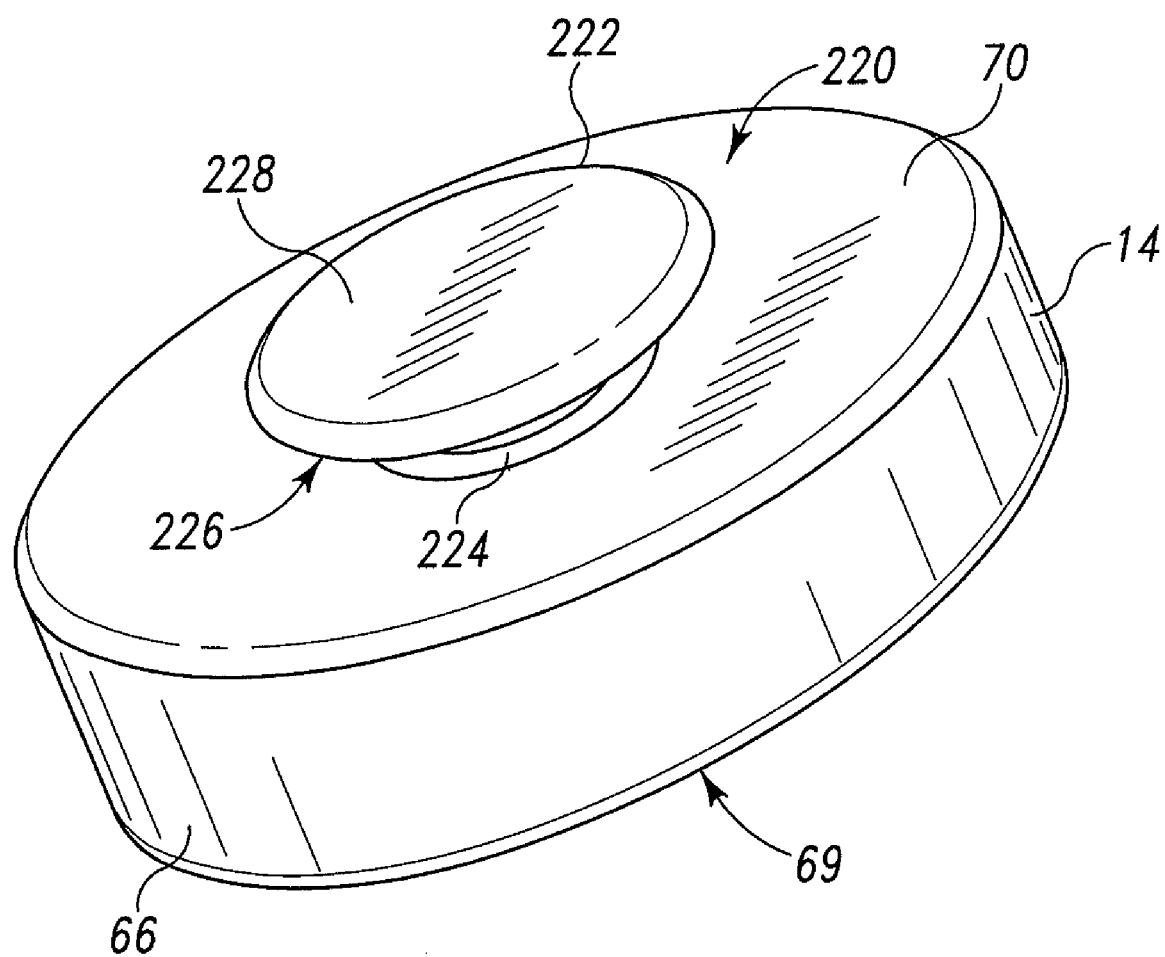
FIG. 15 is a bottom perspective view of one embodiment of a tibial insert of the unicompartmental tibial assembly of FIG. 13.

As shown in FIG. 15, the flange 222 has a generally elliptical or circular bottom profile, but may have other configurations in other embodiments. The flange 220 includes a top surface 226 and a bottom surface 228. In the embodiment illustrated in FIGS. 14-17, the top surface 226 is oblique or otherwise non-parallel to the bottom surface 228 such that the flange 220 may be received in the track 200. Additionally, the top surface 226 is oblique or otherwise not parallel to the track's bottom surface 202 when tibial insert 14 is received therein. However, in embodiments wherein the lips 208, 210 have bottom surfaces substantially parallel to the track's bottom surface 202, the top surface 226 of the flange 222 may be parallel to the bottom surface 228 of the flange 222 and/or to the track's bottom surface 202 such that the flange 222 may be received in the track 200.

Figure 16:
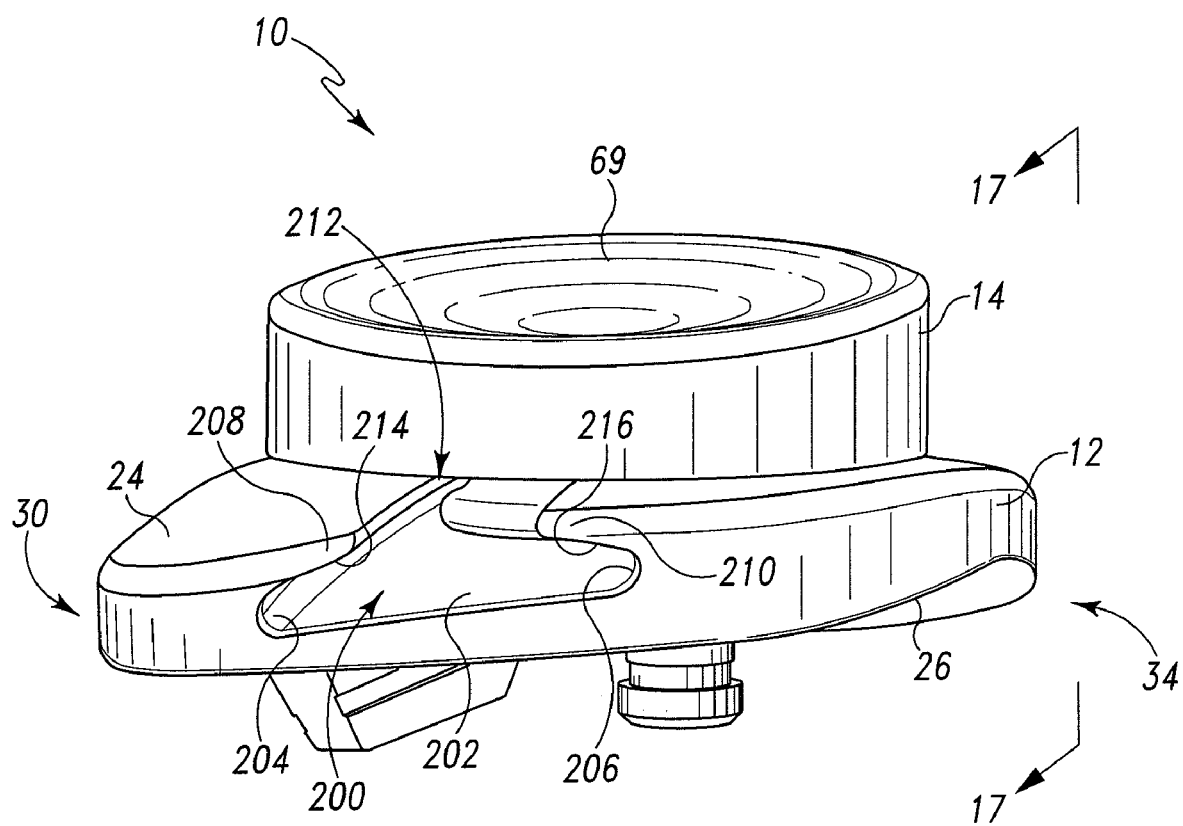
FIG. 16 is a perspective view of the unicompartmental tibial assembly of FIG. 13 in an assembled configuration.
Figure 17:
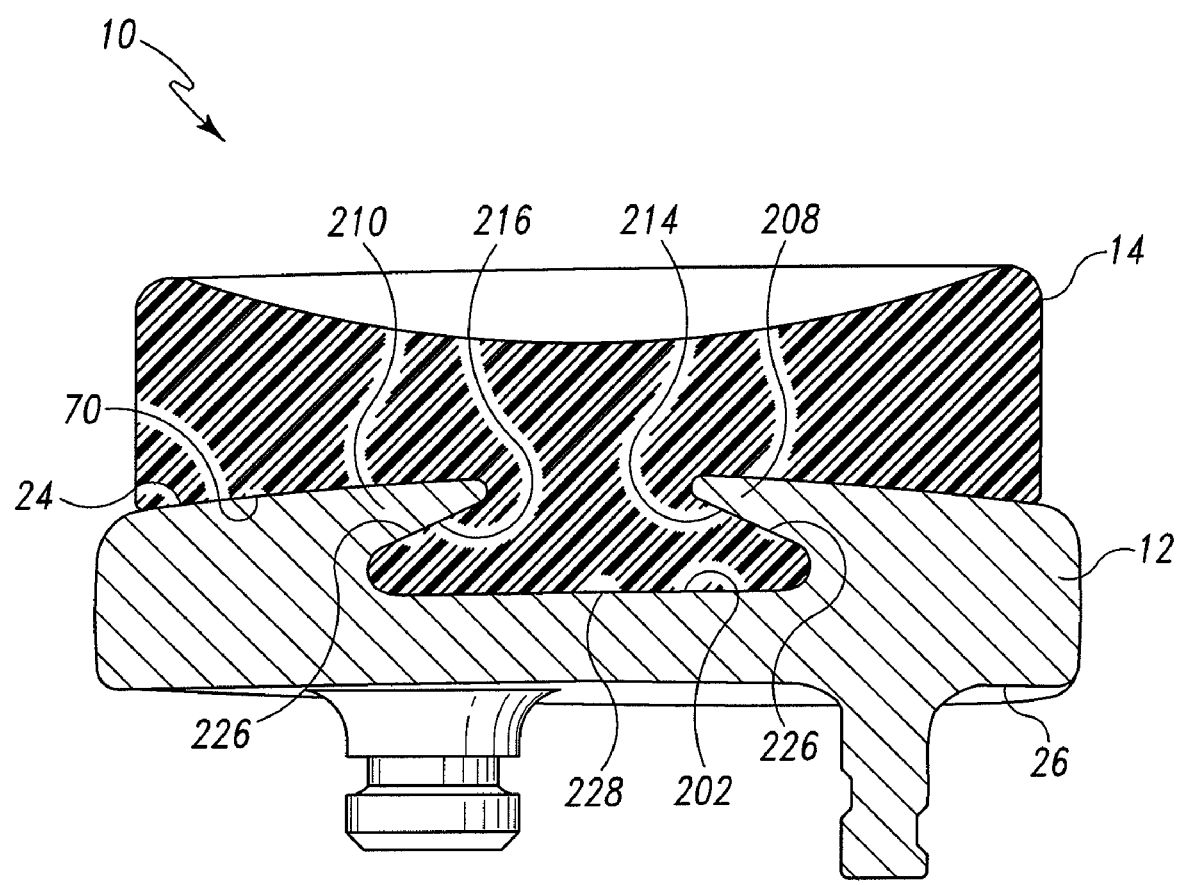
FIG. 17 is a cross-sectional view of the unicompartmental tibial assembly of FIG. 16 taken generally along the section lines 17-17.

During the performance of the orthopaedic surgical procedure (e.g., a UKA or TKA procedure), the tibial insert 14 may be coupled to the tibial tray 12 by positioning the tibial insert 14 on the tibial tray 12 such that the stem 220 of the insert 14 is received in the track 200 of the tray 12 as shown in FIGS. 16 and 17. As described above in regard to the embodiment of FIGS. 1-6, when the tibial insert 14 is coupled to the tibial tray 12, the bottom surface 70 of the tibial insert 14 contacts or is otherwise adjacent to the upper surface 24 of the tibial tray 12. Again, because the bottom surface 70 of the tibial insert 14 is concave and the upper surface 24 of the tibial tray 12 is convex, the surfaces 24, 70 mate and thereby allow the tibial insert 14 to be moved relative to the tibial tray 12. In addition, the bottom surface 228 of the flange 222 contacts or is otherwise positioned adjacent the track's bottom wall 202 when the tibial insert 14 is coupled to the tibial tray 12. Because the bottom surface 228 is substantially planar and the track's bottom wall 202 is also substantially planar, the surface 228 and the wall 202 mate and thereby allow the tibial insert 14 to be moved relative to the tibial tray 12. Additionally, when the tibial insert 14 is coupled to the tibial tray 12, the top surface 226 of the flange 222 contacts or is otherwise positioned adjacent the bottom surfaces 214, 216 of the lips 208, 210, respectively. Once the stem 220 is received by the track 200, the tibial insert 14 is movable relative to the tibial tray 12 along the track 200, but is retained therein by the lips 208, 210.

During patient use, the tibial insert 14 moves along the track 200 of the tibial tray 12 in the generally anterior-posterior direction. In addition, because the flange 222 has a substantially circular shape, the tibial insert 14 may be rotated about a central axis defined by the stem 220. As such, in use, the tibial insert 14 is configured to move in generally anteriorly-posteriorly and/or rotationally with respect to the tibial tray 12.

Referring now to FIGS. 18-22, in another embodiment, the tribal tray 12 may include track 300 in place of the track 60. The track 300 has a substantially circular cross-section profile defined by a side wall 302. That is, the side wall 302 is curved or concave in the generally medial-lateral direction. As such, the side wall 302 curves inwardly toward the upper surface 24 of the tibial tray 12 so as to define an elongated opening 304 on the upper surface 24. In addition, the side wall 302 may be curved or otherwise non-planar in the generally anterior-posterior direction. For example, in the illustrative embodiment of FIGS. 18-22, the side wall 302 has a convex shape in the generally anterior-posterior direction.

Figure 18:
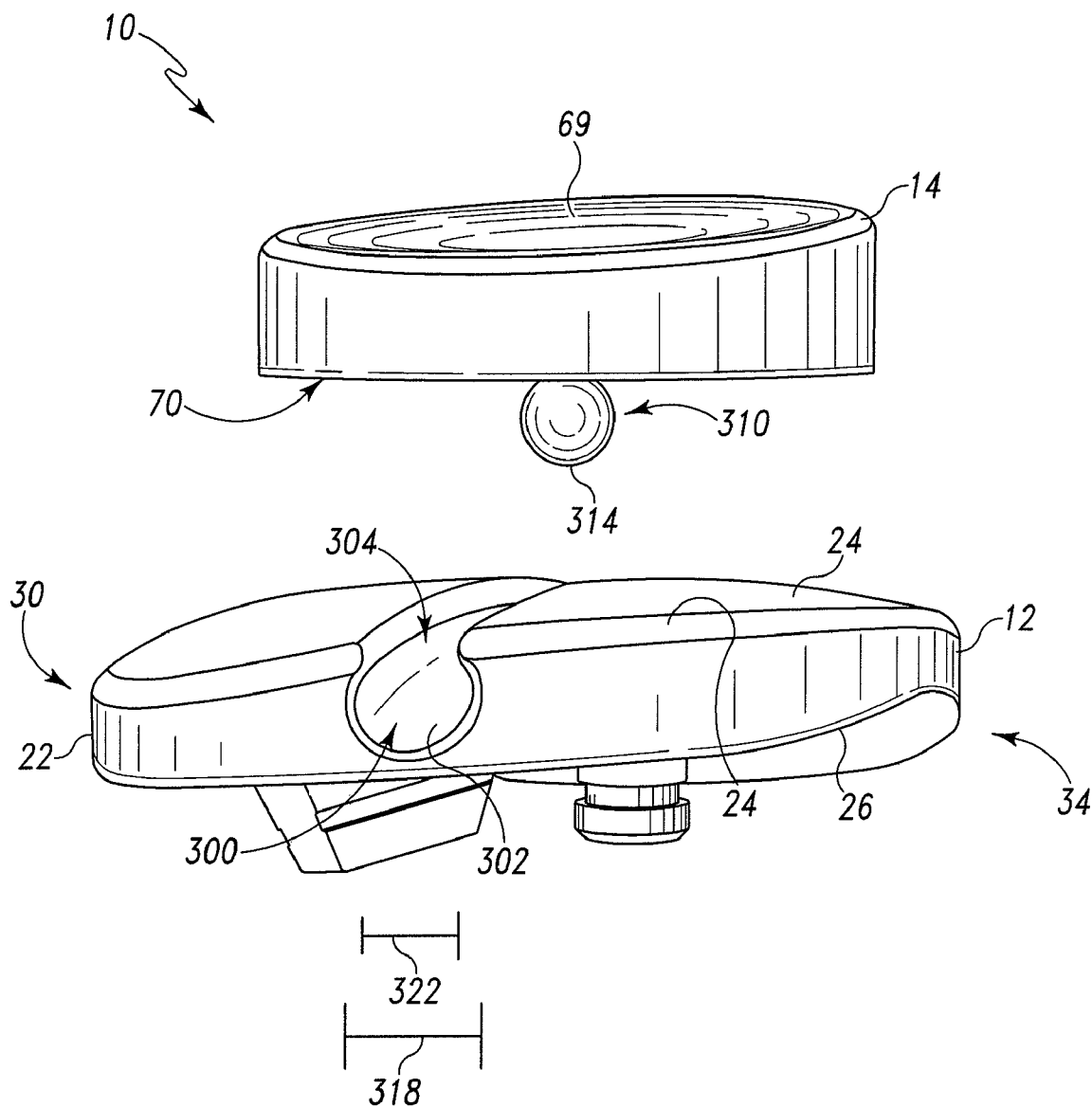
FIG. 18 is an exploded perspective view of another embodiment of the unicompartmental tibial assembly.
Figure 19:
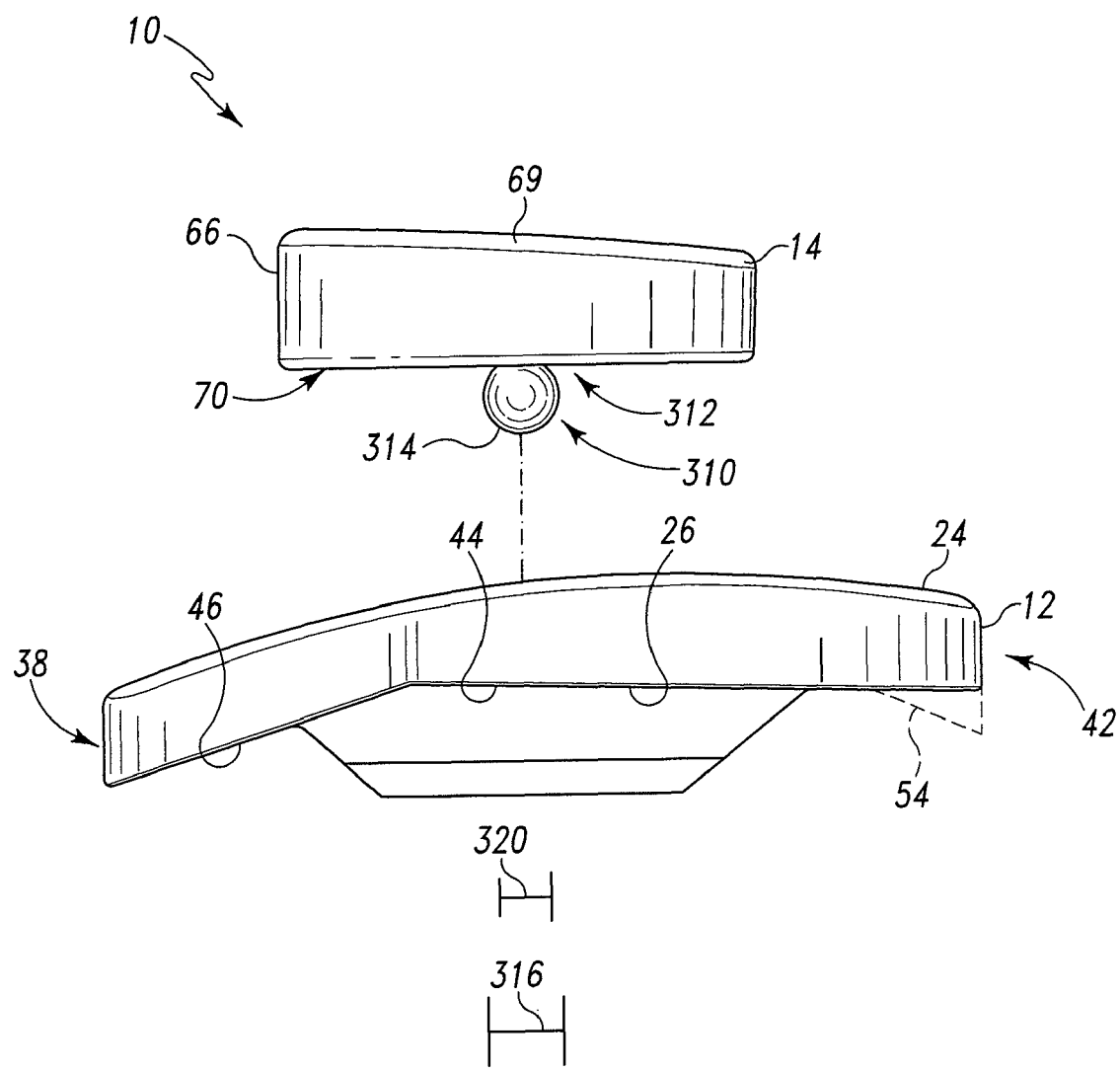
FIG. 19 is an exploded side elevation view of the unicompartmental tibial assembly of FIG. 18.
Figure 20:
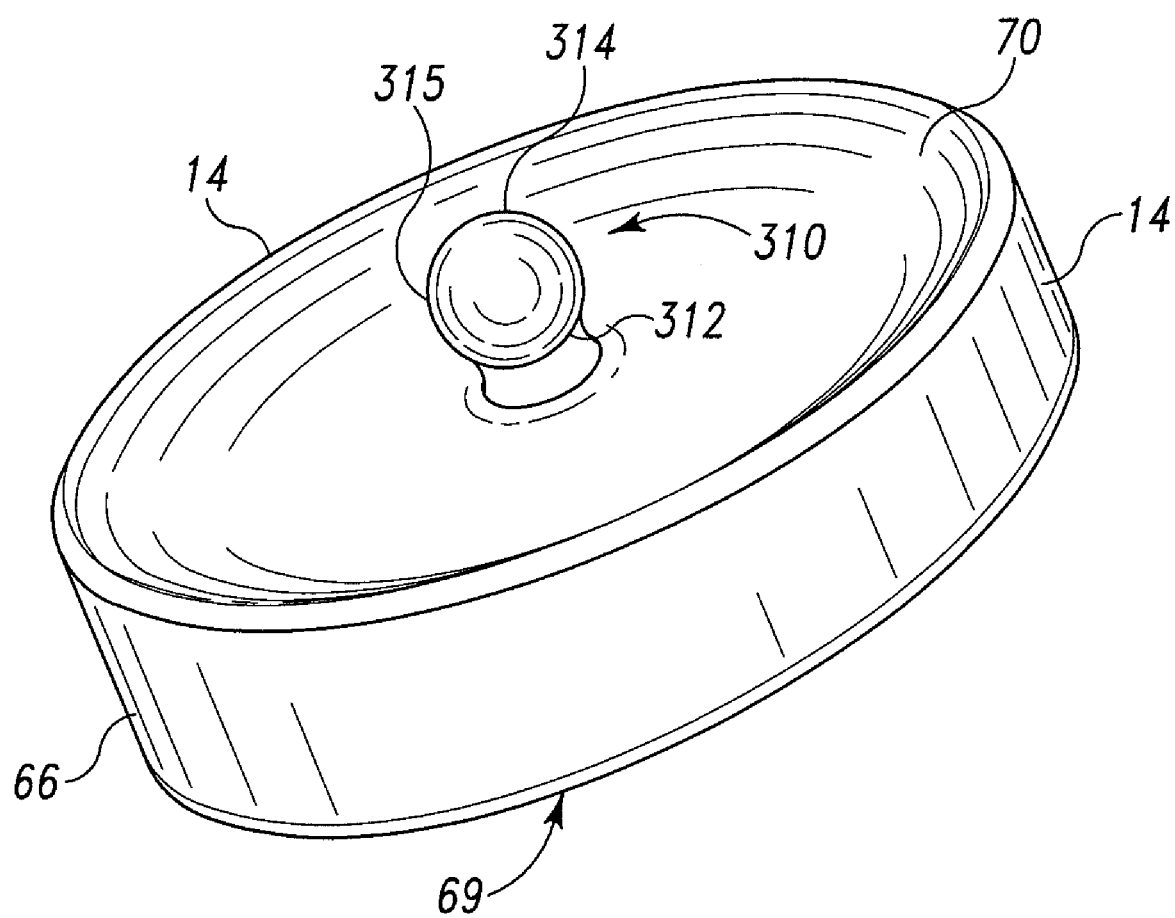
FIG. 20 is a bottom perspective view of one embodiment of the tibial insert of the unicompartmental tibial assembly of FIG. 18.

In embodiments in which the tibial tray 12 includes the track 300, the tibial insert 14 includes a stem 310 in place of the stem 68. The stem 310 includes a flange 314 and a neck 312 connecting the flange 314 to the bottom surface 70 of the base 66 of the tibial insert 14. As shown in FIG. 20, the flange 314 has a generally spherical shape defined by a curved outer surface 315. Additionally, as shown in FIGS. 18 and 19, the flange 222 has a width or diameter 316 that is slightly less than the diameter 318 of the tack 300 as defined by the side wall 302. Similarly, the neck 312 has a width 320 that is slightly less than the width 322 of the elongated opening 304 defined in the upper surface 24. As such, when the stem 310 is received by the track 300, the tibial insert 14 may be moved along the track 300. However, because the diameter 316 of the flange 314 is greater than the width 322 of the elongated opening 304, the tibial insert 14 is retained in the track 300 via the ends of the side wall 302 thereby preventing the tibial insert 14 from lifting off the tibial tray 12.

Figure 21:
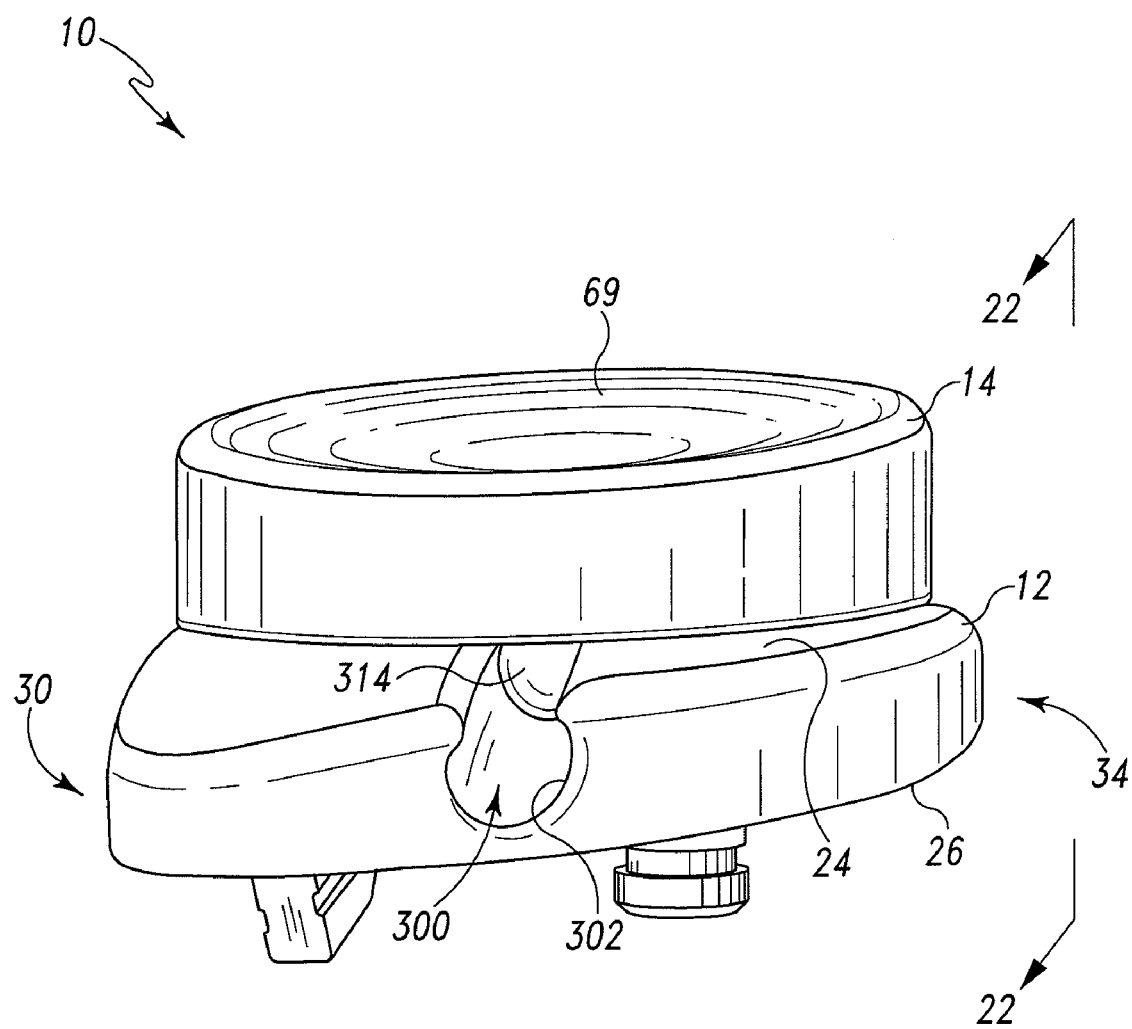
FIG. 21 is a perspective view of the unicompartmental tibial assembly of FIG. 18 in an assembled configuration.
Figure 22:
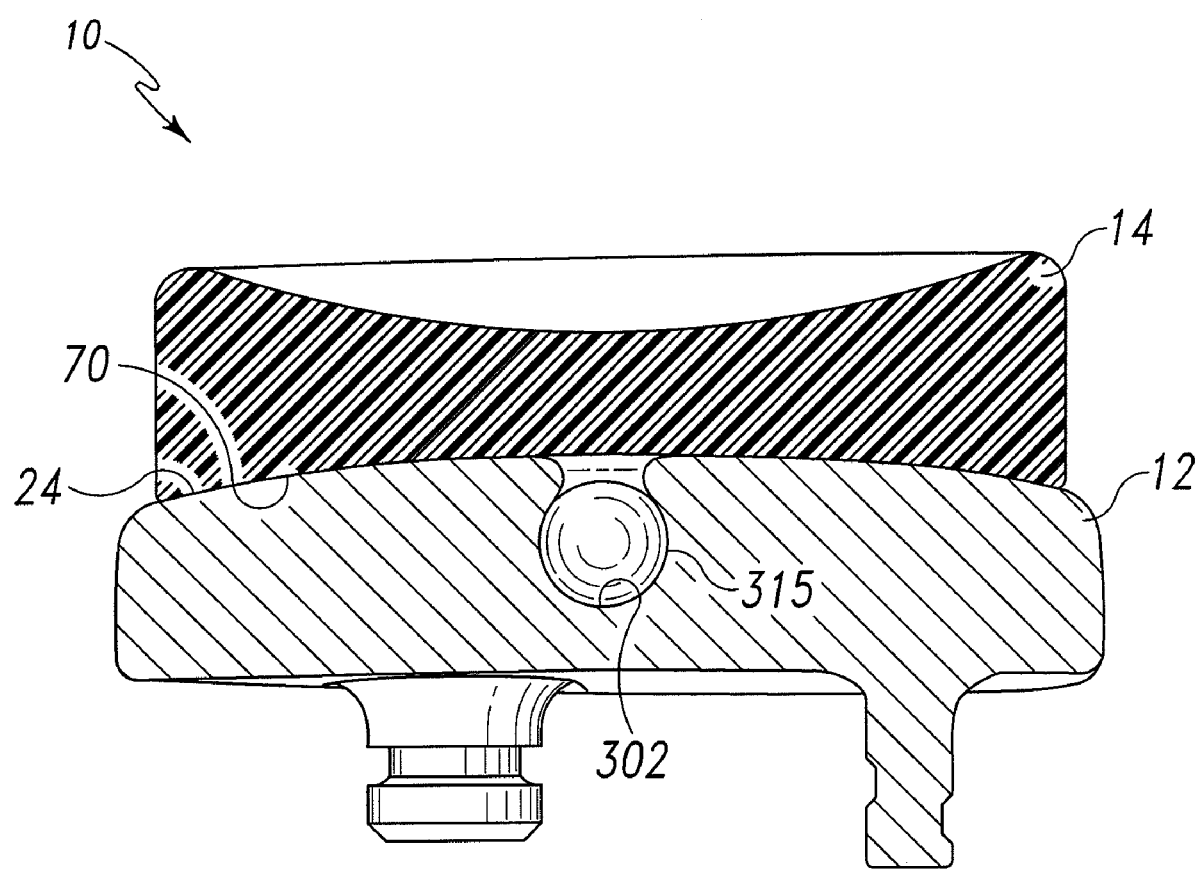
FIG. 22 is a cross-sectional view of the unicompartmental tibial assembly of FIG. 21 taken generally along the section lines 22-22.

During the performance of the orthopaedic surgical procedure (e.g., a UKA or TKA procedure), the tibial insert 14 may be coupled to the tibial tray 12 by positioning the tibial insert 14 on the tibial tray 12 such that the stem 310 of the insert 14 is received in the track 300 of the tray 12 as shown in FIGS. 21 and 22. As described above in regard to the embodiment of FIGS. 1-6, when the tibial insert 14 is coupled to the tibial tray 12, the bottom surface 70 of the tibial insert 14 contacts or is otherwise adjacent to the upper surface 24 of the tibial tray 12. Again, because the bottom surface 70 of the tibial insert 14 is concave and the upper surface 24 of the tibial tray 12 is convex, the surfaces 24, 70 mate and thereby allow the tibial insert 14 to be moved relative to the tibial tray 12. In addition, the curved outer surface 315 of the flange 314 contacts or is otherwise positioned adjacent to the track's curved side wall 302. Once the stem 310 is received by the track 300, the tibial insert 14 is movable relative to the tibial tray 12 along the track 14, but is retained therein by the inwardly curving ends of the sidewall 302.

During patient use, the tibial insert 14 moves along the track 300 of the tibial tray 12 in the generally anterior-posterior direction. In addition, because the flange 314 has a substantially spherical shape, the tibial insert 14 may be rotated about a central axis defined by the stem 310. As such, in use, the tibial insert 14 is configured to move anteriorly-posteriorly and/or rotationally with respect to the tibial tray 12.

Referring now to FIGS. 23-28, in another embodiment, the tribal tray 12 may include track 400 in place of the track 60. The track 400 is defined by a bottom wall 402 and side walls 404, 406. An inboard lip 408 extends from the side wall 404 over a portion of the bottom wall 402. Similarly, an outboard lip 410 extends from the side wall 406 over a portion of the bottom wall 402. The lips 408, 410 define an elongated opening 412 in the upper surface 24 of the tibial tray 12. In the illustrative embodiment, the outboard lip 410 extends from the side wall 406 a distance greater than the inboard lip 408. However, in other embodiments, the lips 408, 410 may extend from the side walls 404, 406 the same or similar distances. The inboard lip 408 includes a bottom surface 413 and the outboard lip 410 includes a bottom surface 415. In the illustrative embodiment, the bottom surfaces 413, 415 are oblique or otherwise non-parallel to the track's bottom wall 402. However, in other embodiments, the bottom surfaces 413, 415 may be substantially parallel to the track's bottom wall 402.

As with the track 60, the bottom wall 402 of the track 400 may be planar or non-planar. In the illustrative embodiment, the bottom wall 402 of the track is substantially planar or flat in the generally medial-lateral direction, but convex in the generally anterior-posterior direction similar to the bottom wall 102 of the track 100 illustrated in and described above in regard to FIGS. 7-12.

Figure 23:
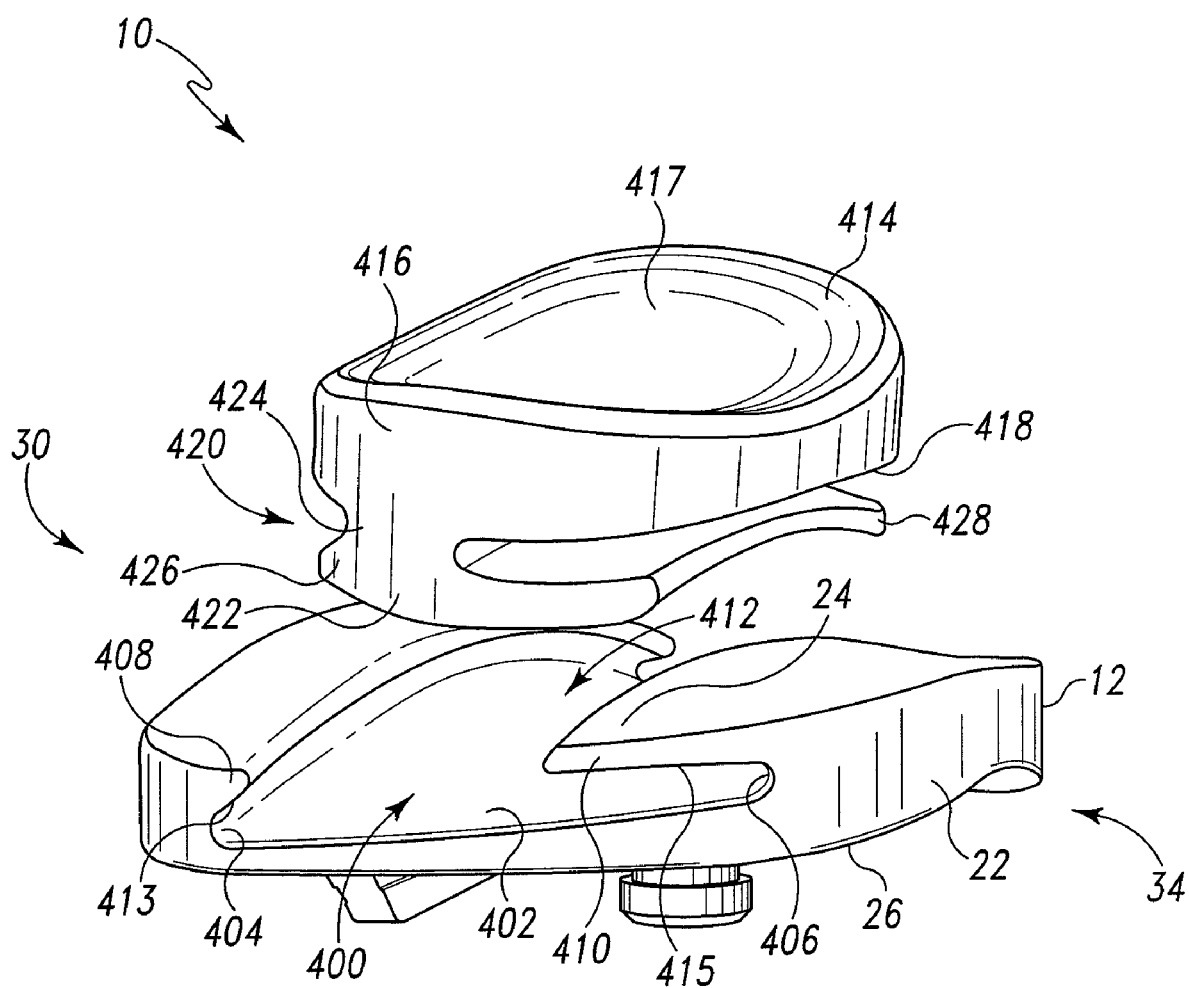
FIG. 23 is an exploded perspective view of another embodiment of a unicompartmental tibial assembly.
Figure 24:
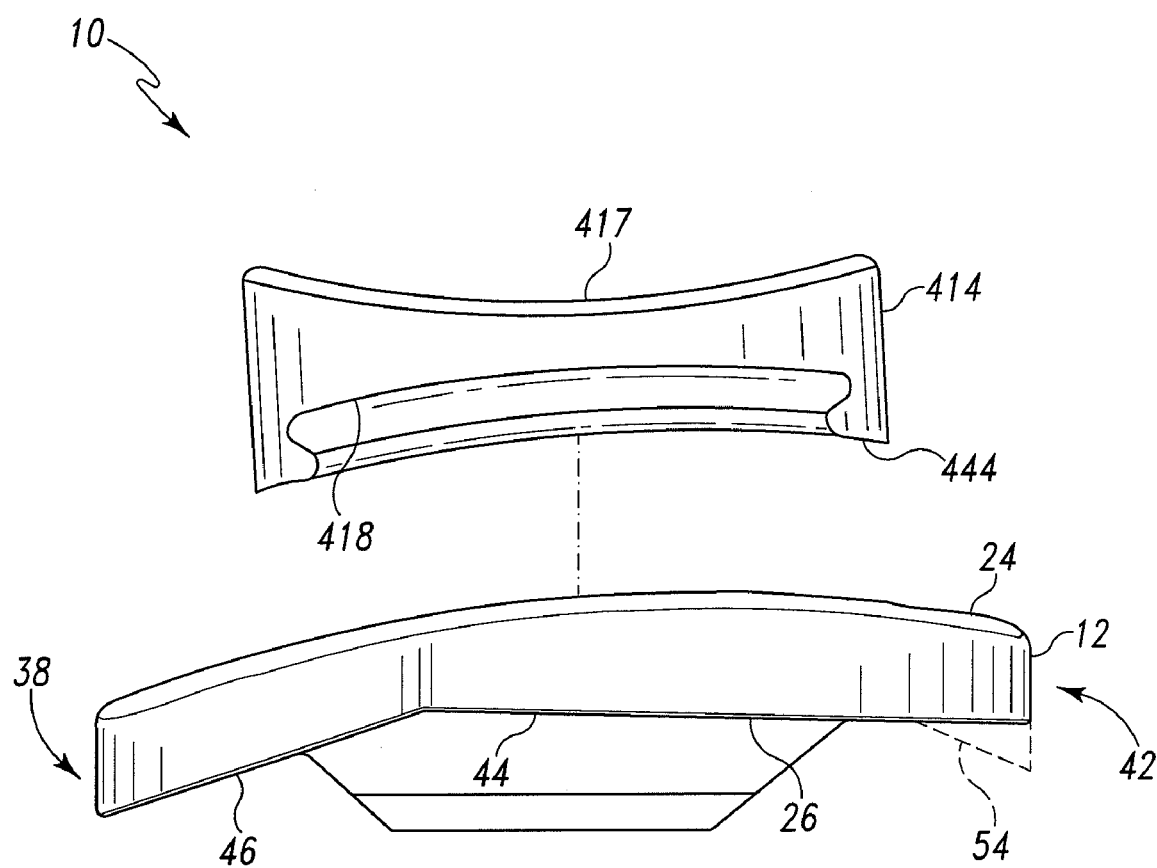
FIG. 24 is an exploded side elevation view of the unicompartmental tibial assembly of FIG. 23.
Figure 25:
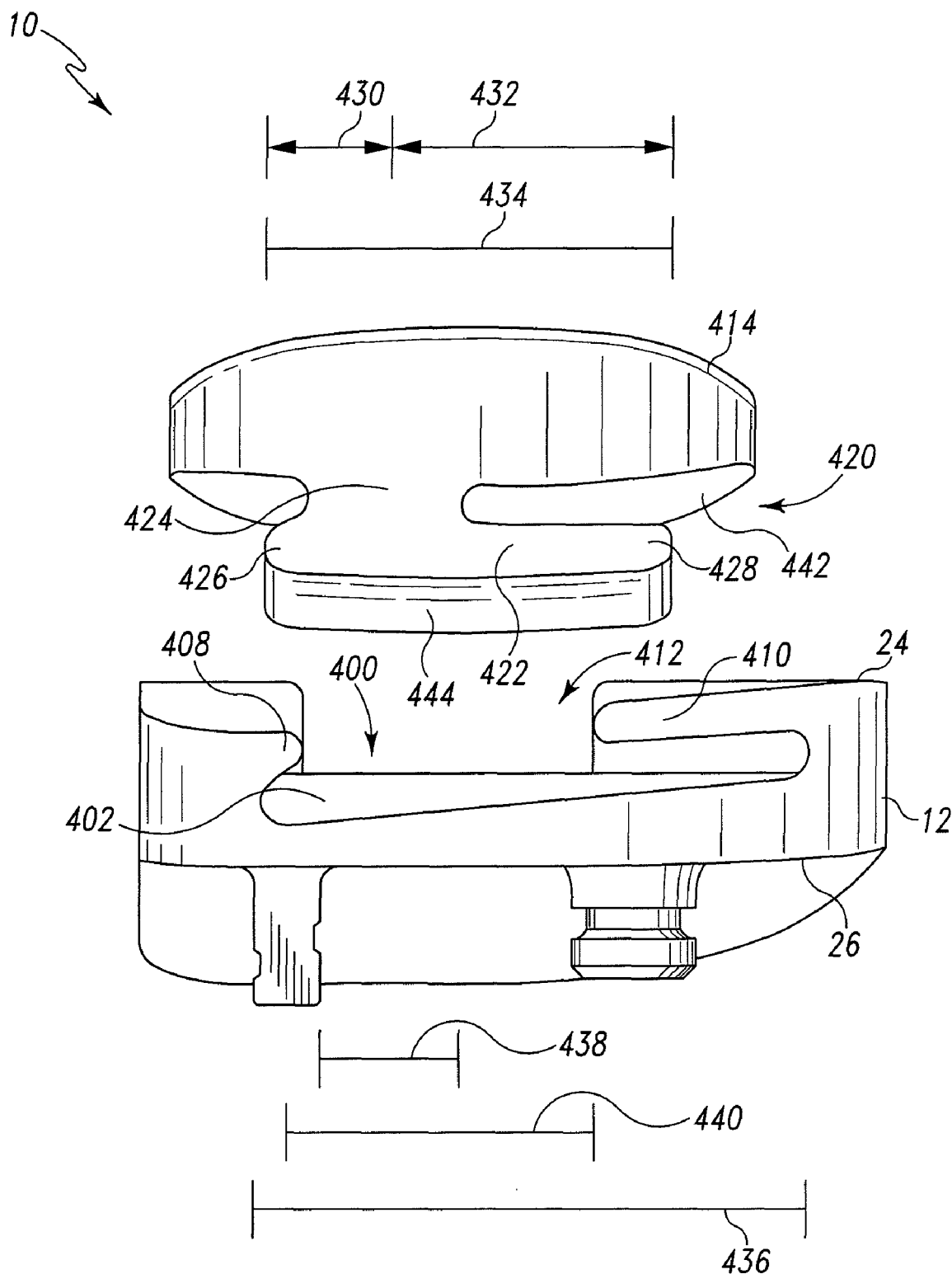
FIG. 25 is an exploded end elevation view of the unicompartmental tibial assembly of FIG. 23.
Figure 26:
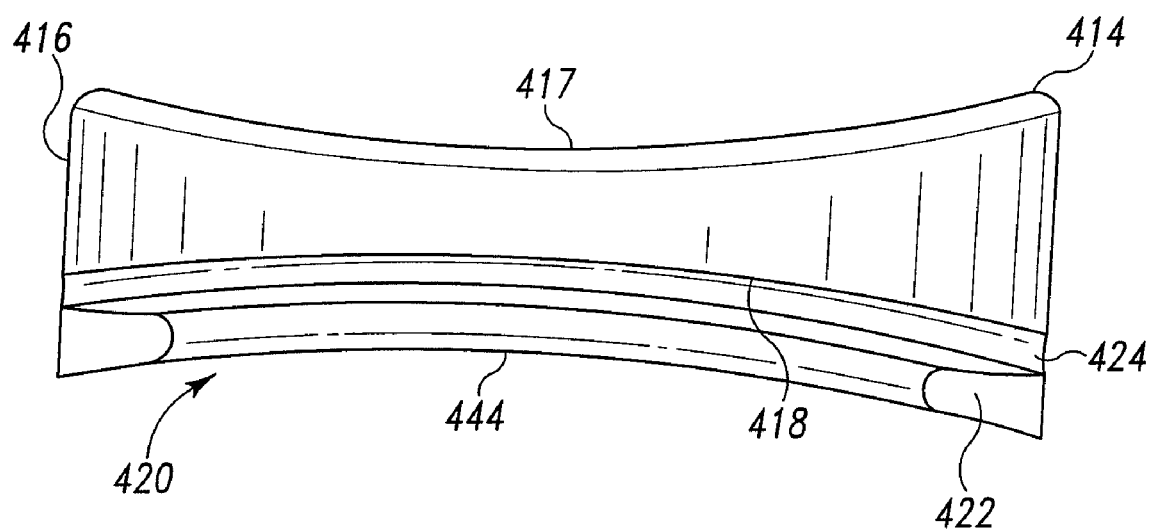
FIG. 26 is a side elevation view of a tibial insert of the unicompartmental tibial assembly of FIG. 23.

In embodiments in which the tibial tray 12 includes the track 400, the tibial insert 14 may be embodied as an elongated tibial insert 414 as shown in FIG. 23. The tibia insert 414 includes an elongated base 416 and an elongated stem 420 extending downwardly therefrom. The base 416 has an elongated upper bearing surface 417 and an elongated bottom surface 418. Similar to the bearing surface 69 of the tibial insert 14 described above, the upper bearing surface 417 of the tibial insert 414 is configured to engage a natural or prosthetic femoral condyle of a patient's femur. During use, the patient's femur or femoral component articulates on the upper bearing surface 417. Similar to the bottom surface 70 described above, the bottom surface 418 is configured to contact or otherwise be positioned adjacent to the upper surface 24 of the tibial tray 12 when coupled together as illustrated in FIG. 26. As such, the bottom surface 418 may be planar or non-planar (e.g., convex or concave) based upon the curvature of the upper surface 24 such that the bottom surface 418 is able to mate with the upper surface 24 during use. In the illustrative embodiment of FIGS. 23-28, the bottom surface 418 of the tibial insert 414 is concave as illustrated in FIG. 26 and is configured to contact or otherwise mate with the convex upper surface 24 of the tibial insert 414.

The stem 420 is configured to be received in the track 400 of the tibial tray 12. The stem 420 includes a flange 422 and a neck 424 connecting the flange 422 to the bottom surface 418 of the base 416 of the insert 414. The flange 422 has a generally rectangular bottom profile and includes an inboard end 426 and an outboard end 428. As shown in FIG. 25, the outboard end 428 extends from the end of the neck 324 farther than the inboard end 426. That is, the shorter inboard end 426 of the flange 422 extends from a center of the neck 424 a distance 430 and the outboard end 428 extends from the center of the neck 424 a distance 432, which is greater than the distance 430. However, in other embodiments, the inboard end 426 may extend from the neck 424 farther than the outboard end 428 or, alternatively, the ends 426, 428 may extend from the neck 424 the same or similar distance depending upon the configuration of the track 400.

As shown in FIG. 25, the flange 422 has a width or diameter 434 that is slightly less than width 436 of the track's bottom wall 402. Similarly, the neck 424 has a width 438 that is slightly less than the width 440 of the elongated opening 412 defined between the lips 408, 410. As such, when the stem 420 is received by the track 400, the tibial insert 414 may be moved along the track 400. However, because the width 434 of the flange 422 is greater than the width 440 of the elongated opening 412, the tibial insert 414 is retained in the track 400 via the lips 408, 410 thereby preventing the tibial insert 414 from lifting off the tibial tray 12.

The flange 422 includes an top surface 442 and a bottom surface 444. In the embodiment illustrated in FIGS. 23-28, the top surface 442 is oblique or otherwise not parallel to the bottom surface 444 such that the flange 422 may be received in the track 400. Additionally, the top surface 442 is oblique or otherwise not parallel to the track's bottom wall 402 when tibial insert 414 is received therein. However, in embodiments wherein the lips 408, 410 have bottom surfaces substantially parallel to the track's bottom surface 402, the top surface 442 of the flange 422 may be parallel to the bottom surface 444 of the flange 422 and/or to the track's bottom wall 402 such that the flange 422 may be received in the track 400.

Figure 27:
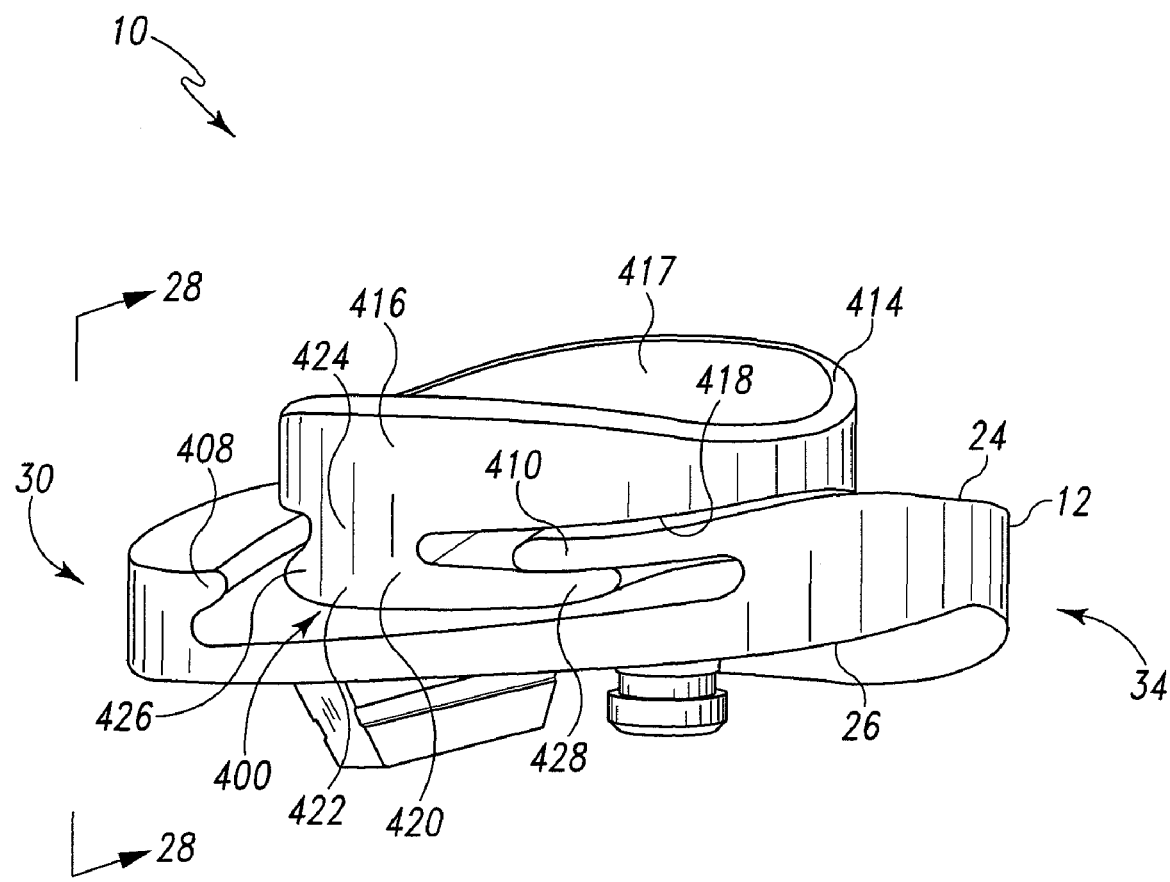
FIG. 27 is a perspective view of the unicompartmental tibial assembly of FIG. 23 in an assembled configuration.
Figure 28:
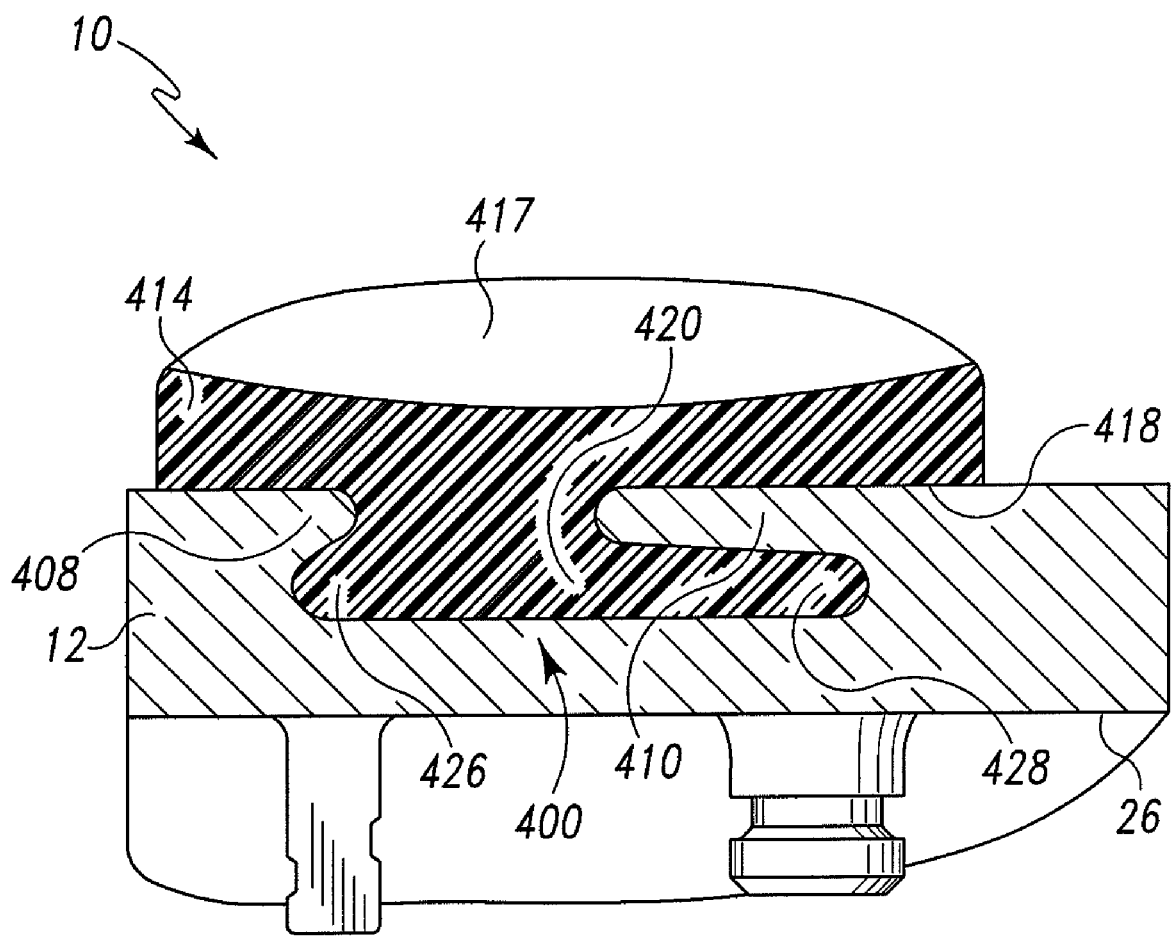
FIG. 28 is a cross-sectional view of the unicompartmental tibial assembly of FIG. 27 taken generally along the section lines 28-28.
Figure 29:
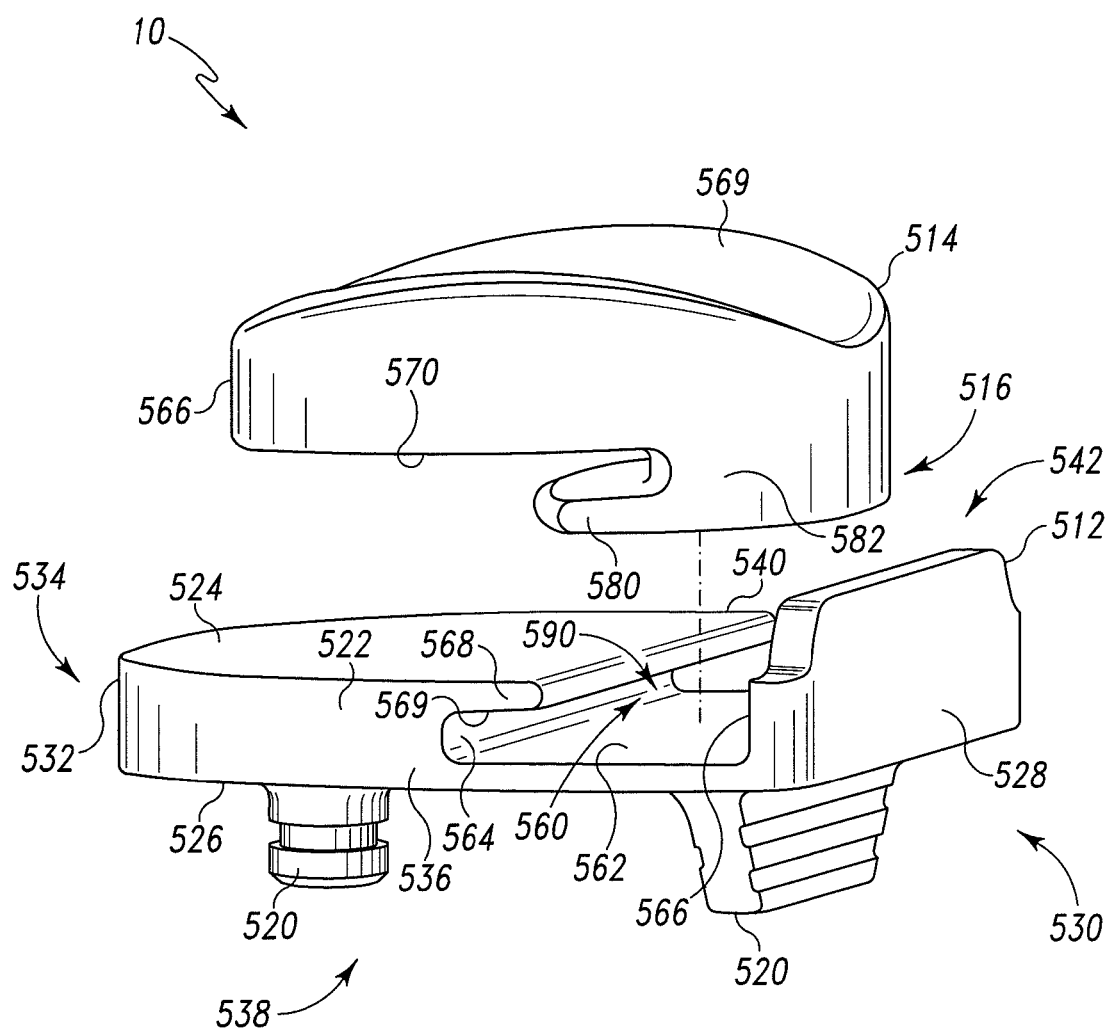
FIG. 29 is an exploded perspective view of another embodiment of a unicompartmental tibial assembly.

During the performance of the orthopaedic surgical procedure (e.g., a UKA or TKA procedure), the tibial insert 414 may be coupled to the tibial tray 12 by positioning the tibial insert 414 on the tibial tray 12 such that the stem 420 of the insert 414 is received in the track 400 of the tray 12 as shown in FIGS. 27 and 28. When the tibial insert 414 is coupled to the tibial tray 12, the bottom surface 418 of the tibial insert 414 contacts or is otherwise adjacent to the upper surface 24 of the tibial tray 12. Because the bottom surface 418 of the tibial insert 414 is concave and the upper surface 24 of the tibial tray 12 is convex, the surfaces 24, 418 mate and thereby allow the tibial insert 414 to be moved relative to the tibial tray. In addition, the bottom surface 444 of the flange 422 contacts or is otherwise positioned adjacent the track's bottom wall 402 when the tibial insert 414 is coupled to the tibial tray 12. Because the bottom surface 444 and the track's bottom wall 402 are substantially planar in the generally medial-lateral direction and curved in the generally anterior-posterior direction, the wall 402 and the surface 444 mate and thereby allow the tibial insert 414 to be moved relative to the tibial tray 12. Additionally, when the tibial insert 414 is coupled to the tibial tray 12, the shorter inboard end 426 of the flange 422 is received in the region defined under the inboard lip 408 and the longer lateral end 428 is received in the region defined under the outboard lip 410. Once the stem 420 is received by the track 400, the tibial insert 414 is movable in the generally anterior-posterior direction relative to the tibial tray 12 along the track 400, but is retained therein by the lips 408, 410.

Referring now to FIGS. 29-35, in another embodiment, the tibial assembly 10 includes a tibial tray 512 and a tibial insert 514. As described above in regard to the embodiment of FIGS. 1-7, the tibial insert 514 is illustratively formed from a polymer material, but may be formed from other materials, such as a ceramic material, a metallic material, a bio-engineered material, or the like, in other embodiments. Similarly, the tibial tray 512 is illustratively formed from a metallic material, but may be formed from other materials, such as a ceramic material, a polymer material, a bio-engineered material, or the like, in other embodiments.

Similar to the tibial tray 12, the tibial tray 512 is configured to be coupled to a surgically-prepared surface of the proximal end of a patient's tibia. The tibial tray 512 includes a base 522 and a number of anchoring devices 520, commonly referred to as stems or keels, extending downwardly therefrom. When the tibial tray 512 is coupled to the patient's tibia, the anchoring devices 520 are embedded in the patient's tibia to thereby secure the tibial tray 512 to the patient's bone.

The base 522 has a generally "D"-shaped top profile and includes an upper surface 524 and a bottom surface 526 from which the anchoring devices 520 extend. The base 522 has a generally straight outer surface 528 defining an inboard side 530 of the tibial tray 512, a generally curved outer surface 532 defining an outboard side 534 of the tibial tray 512, an end surface 536 defining an anterior side 538 of the tibial tray 512, and an end surface 540 defining a posterior side 542 of the tibial tray 512. It should be appreciated that the illustrative tibial assembly 10 is but one embodiment of a tibial assembly and that the features and components of the tibial assembly 10 may be used with a tibial assembly configured to replace the medial and/or lateral condyle of a patient's right tibia, as well as, the medial and/or lateral condyle of the patient's left tibia.

In the illustrative embodiment, the upper surface 524 and the bottom surface 526 of the tibial tray 512 are substantially planar. However, in other embodiments, any one or both of the surfaces 524, 526 may be non-planar. That is, the surfaces 524, 526 may have a convex shape, a concave shape, or be otherwise curved. In such embodiments, the surfaces 524, 526 may be curved in a generally anterior-posterior direction, in a generally medial-lateral direction, or in both a generally anterior-posterior direction and a generally medial-lateral direction. As discussed below, the upper surface 524 of the tibial tray 512 is configured to contact or otherwise be positioned adjacent to a bottom surface 570 of the tibial insert 514.

The tibial tray 512 includes a track 560 defined longitudinally in the base 522 in a generally anterior-posterior direction. As described below, the track 560 is configured to receive a stem 516 of the tibial insert 514. The illustrative track 560 is defined by a substantially planar bottom surface 562 and side walls 564, 566. The side walls 564, 566 are substantially parallel to each other and extend upwardly from the bottom surface 522 in a substantially orthogonal orientation such that the track 560 defined thereby has a rectangular cross-section. As shown in FIG. 30, the tack 560 is offset toward the inboard side 530 of the base 522 such that the side wall 566 forms a portion of the generally straight outer surface 528.

An outboard lip 568 extends from the side wall 204 over a portion of the bottom wall 564. The outboard lip 568 includes a bottom surface 569. In the illustrative embodiment, the bottom surface 569 of the outboard lip 568 is substantially parallel to the bottom surface 562. However, in other embodiments, the bottom surfaces 570 may be oblique to the bottom surface 562. The outboard lip 568 and the side wall 566 define an elongated opening 590 therebetween.

As with the track 60, the bottom wall 564 of the track 560 may be planar or non-planar. In the illustrative embodiment, the bottom wall 560 is substantially planar or flat. However, in other embodiments, the bottom wall 560 may concavely or convexly curved in the generally medial-lateral direction and/or the anterior posterior direction. As illustrated in FIG. 30, the track 560 is defined in the upper surface 524 of the tibial tray 512 in a generally anterior-posterior direction. However, in other embodiments, the track 560 may be defined in the upper surface 524 of the tibial tray 512 in a generally medial-lateral direction, or some combination of a generally anterior-posterior direction and a generally medial-lateral direction (i.e., a generally diagonal direction). Additionally, although the illustrative track 560 is substantially straight, the tibial tray 512 may include a track having other configurations in other embodiments. For example, a curved track may be used in some embodiments.

The tibial insert 514 includes a base 566 and a stem 516 extending downwardly therefrom. The base 566 has an upper bearing surface 569 and a bottom surface 570. The upper bearing surface 569 of the tibial insert 514 is configured to engage a natural or prosthetic femoral condyle of a patient's femur. During use, the patient's femur or femoral component articulates on the upper bearing surface 569. The bottom surface 570 is configured to contact or otherwise be positioned adjacent to the upper surface 524 of the tibial tray 512 when coupled together. As such, the bottom surface 570 may be planar or non-planar (e.g., convex or concave) based upon the curvature of the upper surface 524 such that the bottom surface 570 is able to mate with the upper surface 524 during use.

The stem 516 includes a flange 580 and a neck 582 connecting the flange 580 to the bottom surface 570 of the base 566 of the tibial insert 514. As shown in FIG. 32, the illustrative flange 580 has a substantially "D"-shaped bottom profile. That is, the center region of the flange 580 extends from the neck 582 farther than the ends of the flange 580. As illustrated in FIGS. 30 and 32, the center region of the flange 580 defines a maximum width 574 of the flange 580, which is slightly less than the width 572 of the track's bottom wall 564. Similarly, the neck 582 has a width has a width 578 that is slightly less than the width 576 of the elongated opening 590 defined between the lip 568 and the side wall 566. As such, when the stem 516 is received by the track 560, the tibial insert 514 may be moved along the track 560. However, because the maximum width 574 of the flange 568 is greater than the width 576 of the elongated opening 590, the tibial insert 514 is retained in the track 560 via the lip 568 thereby preventing the tibial insert 514 from lifting off the tibial tray 512.

During the performance of the orthopaedic surgical procedure (e.g., a UKA or TKA procedure), the tibial insert 514 may be coupled to the tibial tray 512 by positioning the tibial insert 514 on the tibial tray 512 such that the stem 516 of the insert 514 is received in the track 560 of the tray 12 as shown in FIGS. 34 and 35. As described above in regard to the embodiment of FIGS. 1-6, when the tibial insert 514 is coupled to the tibial tray 512, the bottom surface 570 of the tibial insert 514 contacts or is otherwise adjacent to the upper surface 524 of the tibial tray 512. Again, because the bottom surface 570 of the tibial insert 514 is concave and the upper surface 524 of the tibial tray 512 is convex, the surfaces 524, 570 mate and thereby allow the tibial insert 514 to be moved relative to the tibial tray 512.

During patient use, the tibial insert 514 moves along the track 560 of the tibial tray 512 in the generally anterior-posterior direction. In addition, because the flange 568 is substantially "D"-shaped (i.e., the ends of the flange 568 extend from the neck a distance shorter than the center region of the flange 568), the tibial insert 514 may rotate within the track 560. That is, the tibial insert 514 may rotate within the track 560 such that a center axis 592 of the tibial inset 514 is displaced from the center axis 594 of the track 560 as indicated in FIG. 35 via arrow 596. Although only one direction of rotation is shown in FIG. 35, it should be appreciated that the tibial insert 514 is configured to rotate in both directions during use. As such, in use, the tibial insert 514 is configured to move in a generally anterior-posterior direction within the track 560 and rotate some amount within the track 560.

Figure 36:
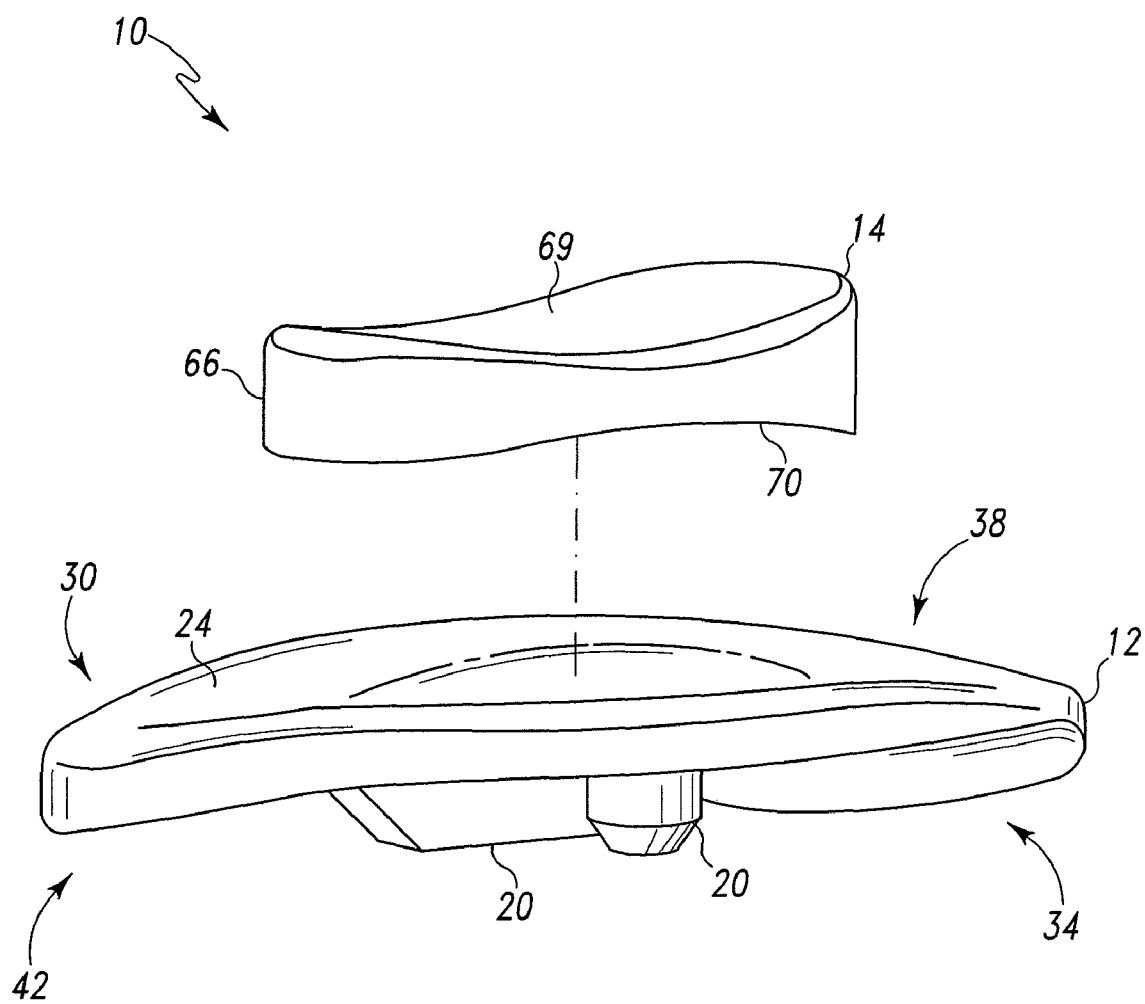
FIG. 36 is an exploded perspective view of another embodiment of a unicompartmental tibial assembly.

Referring now to FIG. 36, in some embodiments, the tribal tray 12 may not include the track 60. Rather, the upper surface 24 of the tibial tray 12 may be substantially solid. However, similar to the embodiment described above in regard to the embodiment of FIGS. 1-7, the upper surface 24 of the tibia tray 12 is non-planar. That is, the upper surface 24 has a convex shape or is otherwise curved. The upper surface 24 may be curved in a generally anterior-posterior direction, in a generally medial-lateral direction, or in both a generally anterior-posterior direction and a generally medial-lateral direction as is illustrated in the illustrative embodiment of FIG. 36.

In embodiments wherein the tibial tray 12 does not include a track, the tibial insert 14 does not include a stem or bearing extending from the bottom surface 70 of the insert 14. However, the bottom surface 70 of the tibial insert 14 is configured to contact or otherwise be positioned adjacent to the top surface 24 of the tibial tray 12 when coupled. As such, similar to the embodiment described above in regard to the embodiment of FIGS. 1-7, the bottom surface 70 is also non-planar. That is the bottom surface 70 of the tibial insert 14 is concave such that the bottom surface 70 is configured to mate with the upper surface 24 of the tibial tray 12.

During the performance of the orthopaedic surgical procedure (e.g., a UKA or TKA procedure), the tibial insert 14 may be coupled to the tibial tray 12 by positioning the tibial insert 14 on the tibial tray 12 such that the bottom surface 70 of the tibial insert 14 contacts or is otherwise adjacent to the top surface 24 of the tray 12. Because the bottom surface 70 is concave and the upper surface 24 of the tibial tray 12 is convex, the surfaces 24, 70 mate and thereby allow the tibial insert 14 to be moved relative to the tibial tray 12. Because the insert 14 does not include a stem, the tibial insert 14 is free to move in the anterior-posterior direction, the medial-lateral direction, as well as, rotationally.

Figure 37:
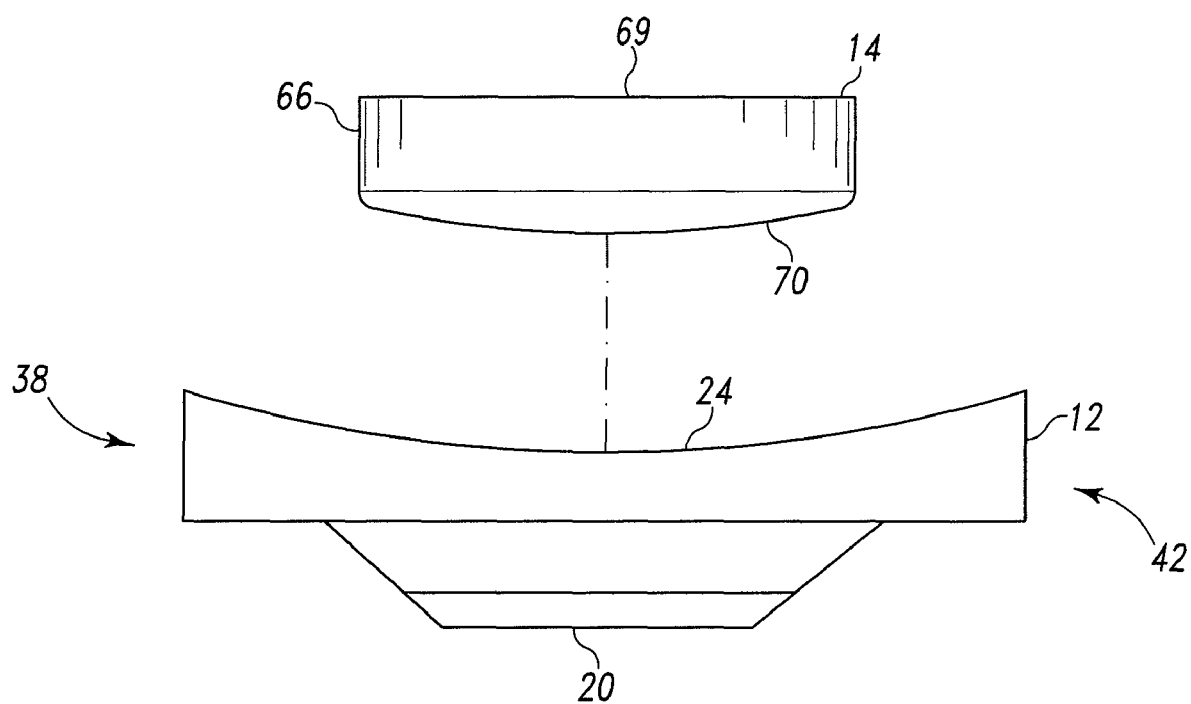
FIG. 37 is an exploded perspective view of another embodiment of a unicompartmental tibial assembly.

Referring now to FIG. 37, in other embodiments, the upper surface 24 of the tibial tray 12 may be concave rather than convex as shown in FIG. 36. The convex upper surface 24 is substantially solid and devoid of the track 60. In such embodiments, the upper surface 24 is configured to receive the bottom surface 70 of the tibial insert 14. The upper surface 24 may be concavely curved in a generally anterior-posterior direction, in a generally medial-lateral direction, or in both a generally anterior-posterior direction and a generally medial-lateral direction as is illustrated in the illustrative embodiment of FIG. 37.

As described above, in embodiments wherein the tibial tray 12 doe not include a track, the tibial insert 14 does not include a stem or bearing extending from the bottom surface 70 of the insert 14. However, the bottom surface 70 of the tibial insert 14 is configured to contact or otherwise be positioned adjacent to the top surface 24 of the tibial tray 12 when coupled. Again, similar to the embodiment described above in regard to the embodiment of FIGS. 1-7, the bottom surface 70 is also non-planar. In the illustrative embodiment of FIG. 37, the bottom surface 70 of the tibial insert 14 is convex such that the bottom surface 70 is configured to mate with the concave upper surface 24 of the tibial tray 12.

During the performance of the orthopaedic surgical procedure (e.g., a UKA or TKA procedure), the tibial insert 14 may be coupled to the tibial tray 12 by positioning the tibial insert 14 on the tibial tray 12 such that the bottom surface 70 of the tibial insert 14 contacts or is otherwise adjacent to the top surface 24 of the tray 12. Because the bottom surface 70 is convex and the upper surface 24 of the tibial tray 12 is concave, the surfaces 24, 70 mate and thereby allow the tibial insert 14 to be moved relative to the tibial tray 12. As discussed above in regard to FIG. 36, the tibial insert 14 is free to move in the anterior-posterior direction, the medial-lateral direction, as well as, rotationally.

Referring now to FIGS. 38-41 in another embodiment, the tibial assembly 10 includes a tibial tray 512 and a polymer bearing, herein referred to as tibial insert 514. Similar to the tibial tray 12, the tibial tray 512 is configured to be coupled to a surgically-prepared surface of the proximal end of a patient's tibia (not shown). The tibial tray 512 includes a base 518 and an anchoring stem or keel 520 extending downwardly therefrom. When the tibial tray 512 is coupled to the patient's bone, the keel 520 is embedded in the patient's tibia to thereby secure the tibial tray 512 to the patient's bone.

The base 518 has a generally "D"-shaped top profile and includes an upper surface 524 and a bottom surface 526 from which the anchoring keel 520 extends. The base 518 has a generally straight outer surface 528 defining an inboard side 530 of the tibial tray 512, a generally curved outer surface 532 defining an outboard side 534 of the tibial tray 512, an end surface 536 defining an anterior side 538 of the tibial tray 12, and an end surface 540 defining a posterior side 542 of the tibial tray 512. It should be appreciated that the illustrative tibial assembly 10 is but one embodiment of a tibial assembly and that the features and components of the tibial assembly 10 may be used with a tibial assembly configured to replace the medial and/or lateral condyle of a patient's right tibia, as well as, the medial and/or lateral condyle of the patient's left tibia.

Figure 38:
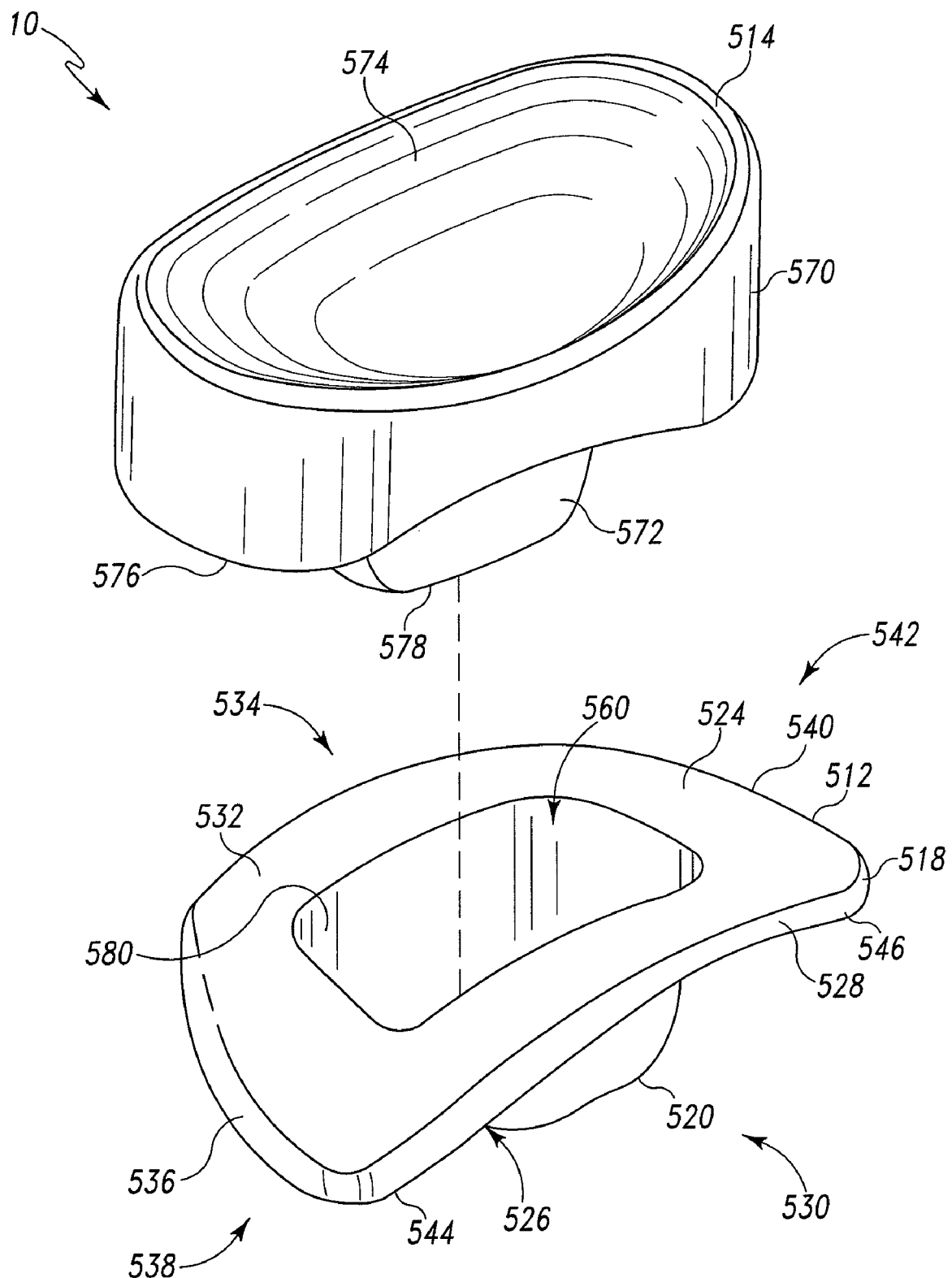
FIG. 38 is an exploded perspective view of another embodiment of the unicompartmental tibial assembly.
Figure 39:
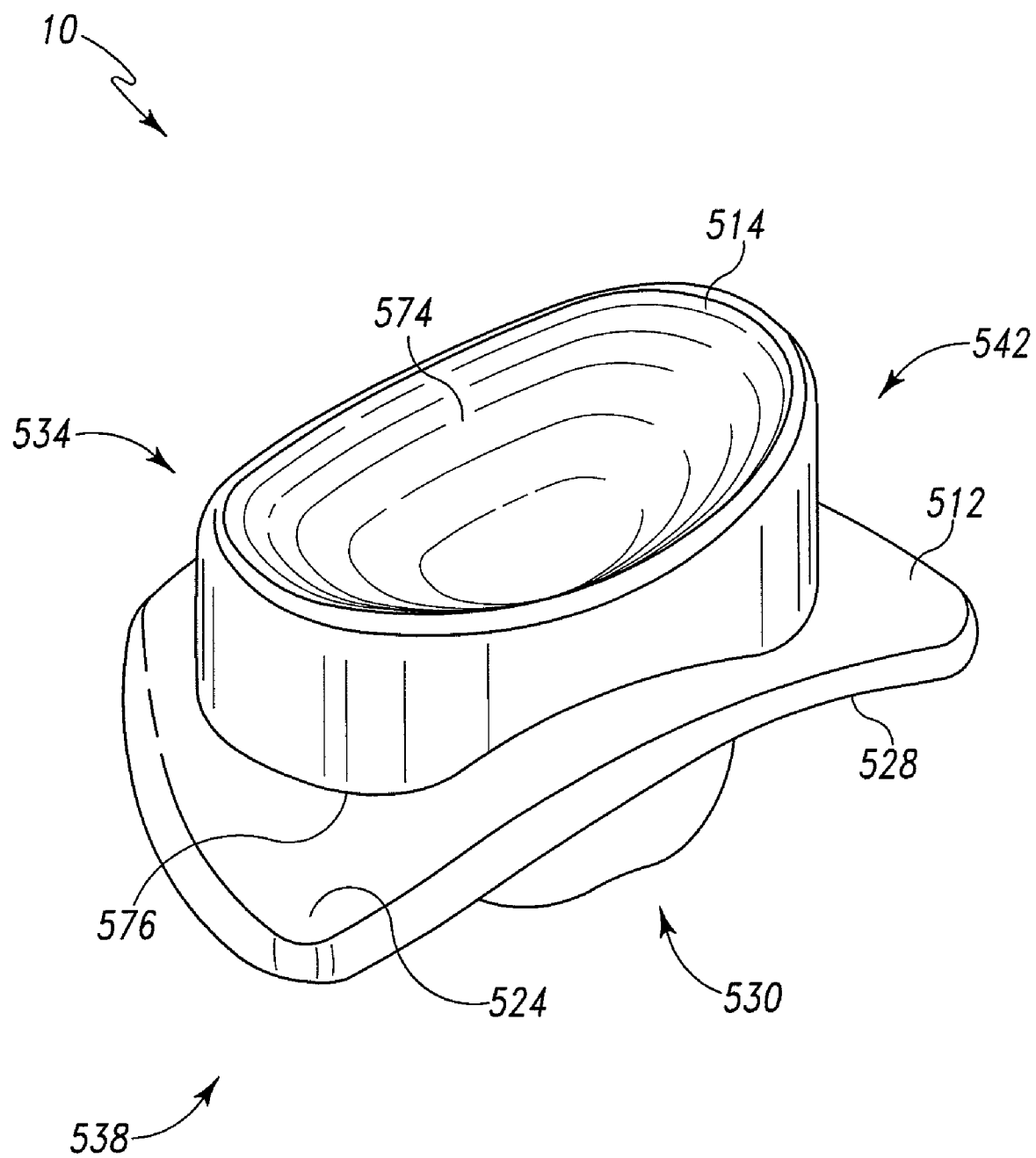
FIG. 39 is a perspective view of the unicompartmental tibial assembly of FIG. 38 in an assembled configuration.
Figure 40:
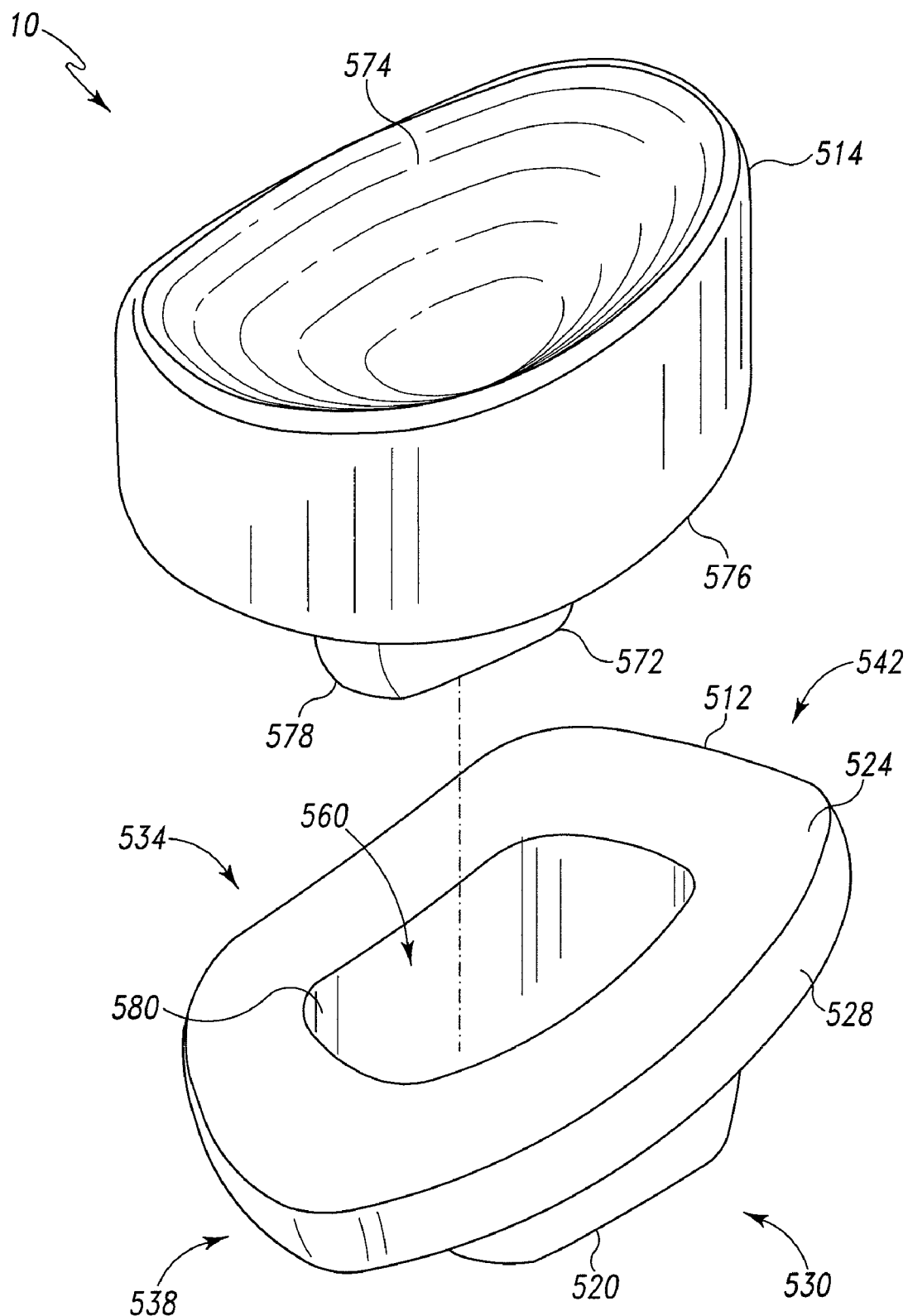
FIG. 40 is an exploded perspective view of another embodiment of the unicompartmental tibial assembly.
Figure 41:
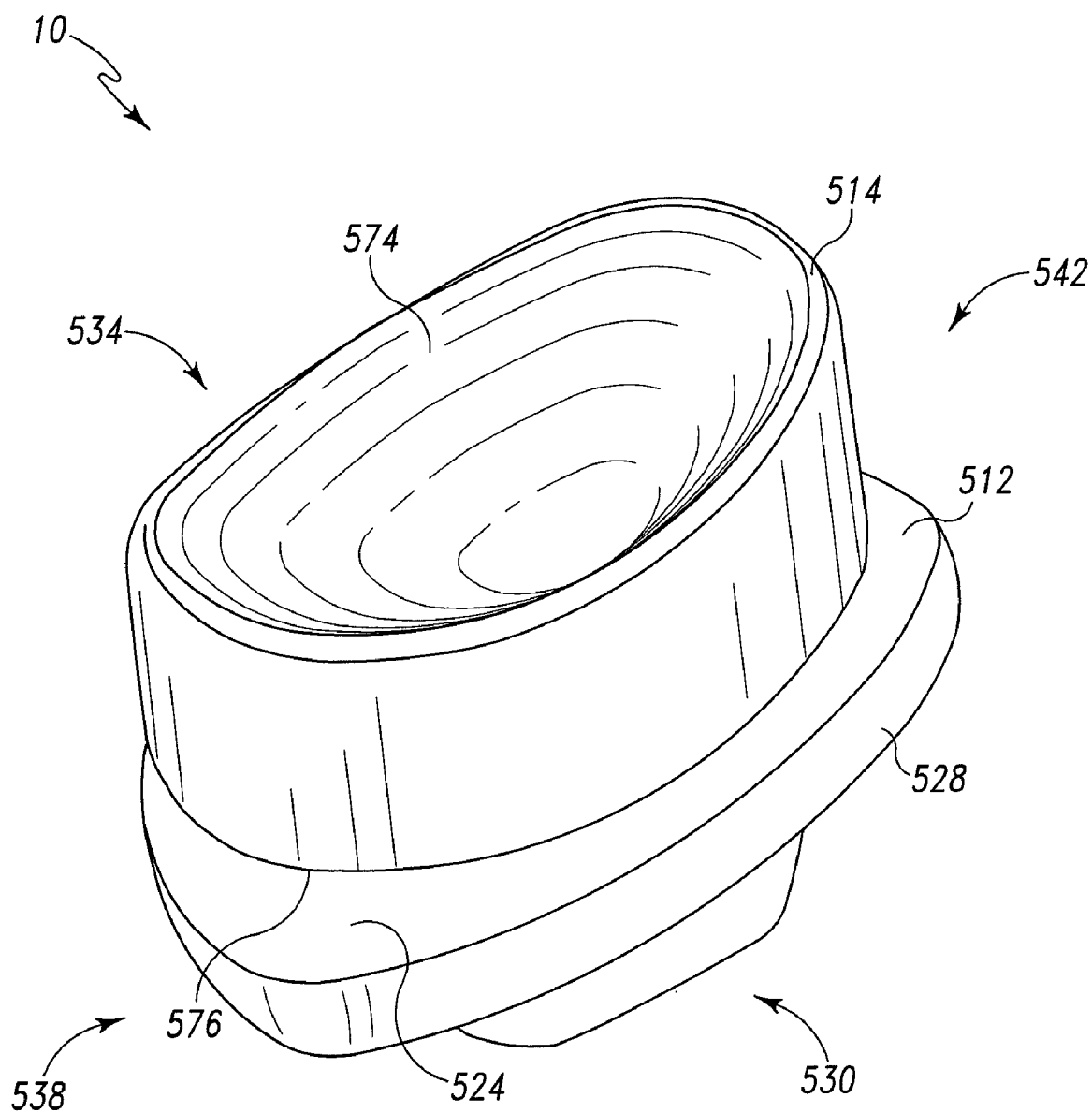
FIG. 41 is a perspective view of the unicompartmental tibial assembly of FIG. 40 in an assembled configuration.

In the illustrative embodiment, the top surface 524 of the tibial tray 512 is non-planar. That is, as shown in FIGS. 38 and 39, the top surface 524 may have a convex shape or otherwise be curved in an outward direction. Alternatively, as shown in FIGS. 40 and 41, the top surface 524 may have a concave shape or otherwise be curved in an inward direction. The top surface 524 may be so curved in the generally anterior-posterior direction, in the generally medial-lateral direction, or in both the generally anterior-posterior direction and the generally medial-lateral direction. As discussed below, the top surface 524 of the tibial tray 512 is configured to contact or otherwise be positioned adjacent to a bottom surface 576 of the tibial insert 514.

Similar to the bottom surface 26 of the tibial tray 12 discussed above in regard to FIGS. 1-6, the bottom surface 526 of the base 518 of the tibial tray 512 is non-planar. That is, as with the bottom surface 26, the bottom surface 526 may be defined by an anterior planar surface 544 positioned toward the anterior side 538 of the tibial tray 512 and a posterior planar surface 546 positioned toward the posterior side 40 of the tibial tray 12. The posterior surface 546 is oblique to the anterior planar surface 544 so as to form an oblique angle therebetween similar to the surfaces 44, 48 described above in regard to FIG. 2. Additionally, in some embodiments, the bottom surface 526 may be defined by more than two oblique planar surfaces. That is, the bottom surface 526 may be defined by any number of oblique planar surfaces. For example, in some embodiments, the bottom surface 526 may include an additional planar surface (not shown) extending from the anterior end of the planar surface 544 so as to define an oblique angle therebetween.

The tibial tray 512 includes an elongated recess 560 defined longitudinally in the base 518 in a generally anterior-posterior direction. As described below, the recess 560 is configured to receive a stem 572 of the tibial insert 514. The illustrative recess 560 has an oblong shape, but recesses having other configurations may be used in other embodiments.

The tibial insert 514 includes a base 570 and a stem 572 extending downwardly therefrom. The base 570 has an upper bearing surface 574 and a bottom surface 576. The upper bearing surface 574 of the tibial insert 514 is configured to engage a natural or prosthetic femoral condyle of a patient's femur. During use, the patient's femur or femoral component articulates on the upper bearing surface 574. The bottom surface 576 is configured to contact or otherwise be positioned adjacent to the top surface 524 of the tibial tray 512 when coupled together as illustrated in FIGS. 39 and 41. As such, the bottom surface 576 may be planar or non-planar (e.g., convex or concave) based upon the curvature of the top surface 524 such that the bottom surface 576 is configured to mate with the top surface 524 during use. For example, in the illustrative embodiment of FIGS. 38 and 39, the bottom surface 576 of the tibial insert 514 is concave and is configured to contact or otherwise mate with the convex top surface 524 of the tibial insert 14 as shown in FIG. 39. Alternatively, in embodiments in which the top surface 524 of the tibial tray 514 is concave as shown in FIG. 40, the bottom surface 576 of the tibial insert 514 is convex is configured to contact or otherwise mate with the concave top surface 524 of the tibial insert 514 as shown in FIG. 41.

The stem 572 is configured to be received in the recess 560 of the tibial tray 415 and, as such, may have any configuration such that stem 572 may be received therein. In the illustrative embodiment of FIGS. 38-41, the stem 572 has an extended dome shape formed by an outer surface 578. The outer surface 578 is configured to contact or otherwise be positioned adjacent to an inner wall 580 that defines the recess 60 when the tibial insert 514 and the tibial tray 512 are coupled together.

During the performance of the orthopaedic surgical procedure (e.g., a UKA or TKA procedure), the tibial insert 514 may be coupled to the tibial tray 512 by positioning the tibial insert 514 on the tibial tray 512 such that the stem 572 of the insert 514 is received in the recess 560 of the tray 512 as shown in FIGS. 39 and 41. When the tibial insert 514 is coupled to the tibial tray 512, the bottom surface 576 of the stem 572 contacts or is otherwise adjacent to the top surface 524 of the tibial tray 512. In the embodiment of FIGS. 38 and 39 in which the bottom surface 576 of the tibial insert 514 is concave and the top surface 524 of the tibial tray 512 is convex, the surfaces 524, 576 mate and thereby allow the tibial insert 514 to be moved relative to the tibial tray 512. Similarly, in the embodiment of FIGS. 40 and 41 in which the bottom surface 576 of the tibial insert 514 is convex and the top surface 524 of the tibial tray 512 is concave, the surfaces 524, 576 mate and thereby allow the tibial insert 514 to be moved relative to the tibial tray 512. In addition, the outer surface 578 of the stem 572 contacts or is otherwise positioned adjacent the recess's inner wall 580 when the tibial insert 514 is coupled to the tibial tray 512. In embodiments in which the size of the stem 572 is slightly less than the size of the recess 560, the stem 572 may be configured to move within the recess 560 in one or more directions. As such, in use, the tibial insert 514 may be configured to move some amount relative to the tibial tray 512 in the generally anterior-posterior direction, the generally medial-lateral direction, or a combination of both directions.

Multiple embodiments of mobile bearing assemblies have been illustrated and described herein. However, the features and configurations of the tibial assemblies illustrated in and described above in regard to FIGS. 1-41 are not limited to mobile bearings assemblies. Rather, such features and configurations may be used with a fixed bearing unicompartmental tibial assembly and/or as part of a fixed total tibial assembly. For example, a fixed tibial assembly may include a tibial insert having a non-planar or otherwise curved bottom surface configured to contact a non-planar or curved upper surface of the tibial tray when coupled thereto. As such, the bottom surface of the tibial insert may be concave or convex and the upper surface of the tibial tray may be convex or concave, respectively, Additionally or alternatively, the fixed tibial assembly may include a tibial tray having a non-planar or otherwise curved bottom surface.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. A mobile tibial assembly comprising:

a tibial tray configured to be coupled to a surgically-prepared surface of the proximal end of a tibia, the tibial tray having (i) an upper surface, (ii) a bottom surface, the bottom surface being configured to contact a portion of the surgically-prepared surface of the tibia when coupled thereto, and (iii) a track defined in the upper surface having a bottom wall that is flat in the medial-lateral direction and convex in the anterior-posterior direction; and a tibial insert having an (i) upper bearing surface and (ii) a bottom bearing surface configured to contact the upper surface of the tibial tray when the tibial insert is coupled to the tibial tray, the bottom bearing surface having a surface area, and (iii) a stem including a circular neck connected to the bottom bearing surface and a circular flange extending from a distal end of the circular neck, the circular neck having a first diameter and a cross-sectional area that is less than the surface area of the bottom bearing surface, the circular flange having a second diameter greater than the first diameter of the circular neck, the stem being received by the track of the tibial tray, wherein (i) the tibial insert is movable along the track relative to the tibial tray, (ii) the upper surface of the tibial tray is convex and the bottom bearing surface of the tibial insert is concave such that the convex upper surface of the tibial tray contacts the concave bottom bearing surface of the tibial insert as the tibial insert is moved along the track relative to the tibial tray in a generally anterior-posterior direction, and (iii) the tibial insert is freely rotatable about a central axis defined by the stem as the tibial insert is moved along the track relative to the tibial tray in the generally anterior-posterior direction.

2. The mobile tibial assembly of claim 1, wherein the bottom surface of the tibial tray comprises a first planar surface and a second planar surface, wherein the first planar surface is oblique relative to the second planar surface.

3. The mobile tibial assembly of claim 2, wherein the bottom surface of the tibial tray comprises a third planar surface oblique relative to the first and the second planar surfaces.

4. The mobile tibial assembly of claim 1, wherein the track of the tibial tray is defined by a first side wall, a second side wall, a first lip extending from the first side wall a first distance over a portion of the bottom wall, and a second lip extending from the second wall a second distance over a portion of the bottom wall, the second distance being greater than the first distance, and the first and second lips defining an opening therebetween.

5. The mobile tibial assembly of claim 4, wherein the circular flange has:

(i) a bottom surface configured to contact the bottom wall when the stem is received thereby, and (ii) a top surface configured to contact a bottom surface of at least one of the first lip and the second lip of the track of the tibial tray when the stem is received thereby.

6. A tibial assembly comprising:

a tibial tray configured to be coupled to a surgically-prepared surface of the proximal end of a tibia, the tibial tray having (i) an upper surface, (ii) a bottom surface configured to contact a portion of the surgically-prepared surface of the tibia when coupled thereto and comprising an anterior planar surface extending from an anterior side of the tibial tray to a posterior end and a posterior planar surface extending from the posterior end of the anterior planar surface to a posterior side of the tibial tray, the posterior planar surface being angled downward such that the posterior planar surface is oblique to the anterior planar surface and the posterior side of the tibial tray is inferior to the anterior side of the tibial tray, and (iii) a track defined in the upper surface having a bottom wall that is flat in the medial-lateral direction and convex in the anterior-posterior direction; and a tibial insert having an (i) upper bearing surface and (ii) a bottom bearing surface configured to contact the upper surface of the tibial tray when the tibial insert is coupled to the tibial tray, the bottom bearing surface having a surface area, and (iii) a stem including a circular neck connected to the bottom bearing surface and a circular flange extending from a distal end of the circular neck, the circular neck having a first diameter and a cross-sectional area that is less than the surface area of the bottom bearing surface, the circular flange having a second diameter greater than the first diameter of the circular neck, the stem being received by the track of the tibial tray, wherein (i) the tibial insert is movable along the track relative to the tibial tray, (ii) the upper surface of the tibial tray is convex and the bottom bearing surface of the tibial insert is concave such that the convex upper surface of the tibial tray contacts the concave bottom bearing surface of the tibial insert when the tibial insert is moved along the track relative to the tibial tray in a generally anterior-posterior direction, and (iii) the tibial insert is freely rotatable about a central axis defined by the stem when the tibial insert is moved along the track relative to the tibial tray in the generally anterior-posterior direction.

7. A mobile tibial assembly comprising:

a tibial tray configured to be coupled to a surgically-prepared surface of the proximal end of a tibia, the tibial tray including (i) a platform having a convex upper surface, (ii) an anchor extending downwardly from a bottom surface of the platform, and (iii) a channel formed in the convex upper surface of the platform, wherein the channel of the tibial tray is generally parallel to an inboard surface of the platform of the tibial tray, extends from an anterior side of the platform to a posterior side of the platform, and includes a bottom wall that is flat in the generally medial-lateral direction and convex in the anterior-posterior direction, and a tibial insert including a platform having a concave bottom bearing surface having a surface area, and a stem received within the channel of the tibial tray, the stem including a circular neck connected to the bottom bearing surface and a circular flange extending from a distal end of the circular neck, the circular neck having a first diameter and a cross-sectional area that is less than the surface area of the bottom bearing surface, the circular flange having a second diameter greater than the first diameter, wherein (i) the stem of the tibial insert includes a medial surface defining a curved line extending from the anterior side of the tibial insert to the posterior side of the tibial insert when viewed in a plan view, (ii) the stem is movable along the channel relative to the tibial tray, (iii) the convex upper surface of the tibial tray contacts the concave bottom surface of the platform as the stem is moved along the channel relative to the tibial tray in a generally anterior-posterior direction, and (iv) tibial insert is freely rotatable about a central axis defined by the stem as the tibial insert is moved along the track relative to the tibial tray in the generally anterior-posterior direction.

* * * * *